(12) United States Patent
Bonda et al.

(10) Patent No.: US 9,765,051 B2
(45) Date of Patent: *Sep. 19, 2017

(54) COMPOSITIONS, APPARATUS, SYSTEMS, AND METHODS FOR RESOLVING ELECTRONIC EXCITED STATES

(71) Applicant: HALLSTAR INNOVATIONS CORP., Chicago, IL (US)

(72) Inventors: Craig A. Bonda, Winfield, IL (US); Shengkui Hu, Darien, IL (US); Qing Jean Zhang, Hickory Hills, IL (US); Zhihui Zhang, Downers Grove, IL (US)

(73) Assignee: HALLSTAR INNOVATIONS CORP., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/792,431

(22) Filed: Jul. 6, 2015

(65) Prior Publication Data

US 2016/0022555 A1    Jan. 28, 2016

Related U.S. Application Data

(60) Division of application No. 13/963,865, filed on Aug. 9, 2013, now Pat. No. 9,145,383, and a continuation-in-part of application No. 13/588,662, filed on Aug. 17, 2012, now Pat. No. 9,125,829, and a continuation-in-part of application No.
(Continued)

(51) Int. Cl.

| | |
|---|---|
| *C07C 255/41* | (2006.01) |
| *C07C 69/618* | (2006.01) |
| *C07C 335/12* | (2006.01) |
| *C07D 335/12* | (2006.01) |
| *A61K 8/35* | (2006.01) |
| *A61K 8/37* | (2006.01) |
| *A61K 8/40* | (2006.01) |
| *A61K 8/49* | (2006.01) |
| *A61K 41/00* | (2006.01) |
| *A61K 47/14* | (2017.01) |
| *A61K 47/16* | (2006.01) |
| *A61K 47/22* | (2006.01) |
| *A61Q 17/04* | (2006.01) |
| *C07C 255/34* | (2006.01) |
| *C07C 255/40* | (2006.01) |
| *C07C 325/04* | (2006.01) |
| *C07C 327/22* | (2006.01) |
| *C07D 311/82* | (2006.01) |

(52) U.S. Cl.
CPC .............. *C07D 335/12* (2013.01); *A61K 8/35* (2013.01); *A61K 8/37* (2013.01); *A61K 8/40* (2013.01); *A61K 8/494* (2013.01); *A61K 8/498* (2013.01); *A61K 8/4986* (2013.01); *A61K 41/0071* (2013.01); *A61K 47/14* (2013.01); *A61K 47/16* (2013.01); *A61K 47/22* (2013.01); *A61Q 17/04* (2013.01); *C07C 69/618* (2013.01); *C07C 255/34* (2013.01); *C07C 255/40* (2013.01); *C07C 255/41* (2013.01); *C07C 325/04* (2013.01); *C07C 327/22* (2013.01); *C07D 311/82* (2013.01); *A61K 2800/522* (2013.01); *C07C 2603/18* (2017.05); *C07C 2603/24* (2017.05); *Y10T 428/249921* (2015.04)

(58) Field of Classification Search
None
See application file for complete search history.

(56) References Cited

U.S. PATENT DOCUMENTS

| | | | |
|---|---|---|---|
| 3,218,166 | A | 11/1965 | Reitter |
| 3,408,187 | A | 10/1968 | Mammino |

(Continued)

FOREIGN PATENT DOCUMENTS

| | | |
|---|---|---|
| CS | 221362 | 9/1982 |
| CZ | 221362 | 4/1983 |

(Continued)

OTHER PUBLICATIONS

US 8,435,706, 05/2013, Sekido (withdrawn)
Nogami et al., Bull. Chem. Soc. Jpn., 1981, 54(11), pp. 3601-3602.*
International search report and written opinion of the international searching authority for co-pending PCT application No. PCT/US2013/054408 mailed Dec. 2, 2013.
Nogami, et al., "The Synthesis of New Electron Acceptors, 9,10-bis[cyano(ethoxycarbonyl)methylene]-9,10-dihydroanthracene and 10-[cyano(ethoxycarbonyl)methylene]-9-anthrone." Bulletin of the Chemical society of Japan (1981), 54(11), 3601-2.

(Continued)

*Primary Examiner* — Brian Gulledge
(74) *Attorney, Agent, or Firm* — Baker & McKenzie LLP

(57) ABSTRACT

The present disclosure relates, according to some embodiments, to molecules, including conjugated fused polycyclic molecules, that may receive excited state energy from other molecules (e.g., light-absorbing molecules) or directly from the irradiation sources. According to some embodiments, the disclosure relates to molecules, including conjugated fused polycyclic molecules, that may resolve (e.g., quench, dissipate) excited state energy, normally by way of releasing it as heat. (e.g., as heat). Conjugated fused polycyclic molecules of various structures are disclosed including Formula III:

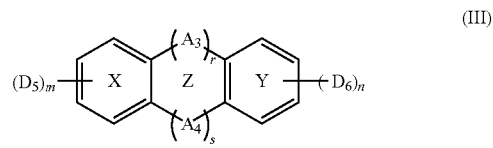

The disclosure further relates to methods of use and/or therapy using molecules of Formulas I, II, and/or III.

4 Claims, 33 Drawing Sheets
(24 of 33 Drawing Sheet(s) Filed in Color)

Related U.S. Application Data

PCT/US2012/067519, filed on Dec. 3, 2012, and a continuation-in-part of application No. 13/805,168, filed on Dec. 18, 2012.

(60) Provisional application No. 61/681,926, filed on Aug. 10, 2012.

(56) References Cited

U.S. PATENT DOCUMENTS

| | | |
|---|---|---|
| 3,408,188 A | 10/1968 | Mammino |
| 3,408,190 A | 10/1968 | Mammino |
| 3,615,412 A | 10/1971 | Hessel |
| 3,674,473 A | 7/1972 | Blanchette |
| 3,752,668 A | 8/1973 | Baltazzi |
| 3,791,824 A | 2/1974 | Bauer et al. |
| 3,841,871 A | 10/1974 | Blanchette |
| 3,864,126 A | 2/1975 | Nishide et al. |
| 3,933,505 A | 1/1976 | Shiba et al. |
| 3,976,485 A | 8/1976 | Groner |
| 3,984,378 A | 10/1976 | Kubota et al. |
| 4,012,251 A | 3/1977 | Turner |
| 4,018,602 A | 4/1977 | Chu |
| 4,032,226 A | 6/1977 | Groner |
| 4,040,735 A | 8/1977 | Winkelmann et al. |
| 4,069,046 A | 1/1978 | Hoegl et al. |
| 4,106,934 A | 8/1978 | Turnblom |
| 4,256,819 A | 3/1981 | Webster et al. |
| 4,350,748 A | 9/1982 | Lind |
| 4,427,753 A | 1/1984 | Fujimura et al. |
| 4,474,865 A | 10/1984 | Ong et al. |
| 4,515,881 A | 5/1985 | Sawada et al. |
| 4,546,059 A | 10/1985 | Ong et al. |
| 4,552,822 A | 11/1985 | Kazmaier et al. |
| 4,559,287 A | 12/1985 | McAneney et al. |
| 4,562,132 A | 12/1985 | Ong et al. |
| 4,567,124 A | 1/1986 | Ohta et al. |
| 4,576,886 A | 3/1986 | Hirose et al. |
| 4,579,800 A | 4/1986 | Hirose et al. |
| 4,599,287 A | 7/1986 | Fujimaki et al. |
| 4,606,861 A | 8/1986 | Ong et al. |
| 4,609,602 A | 9/1986 | Ong et al. |
| 4,810,608 A | 3/1989 | Ueda |
| 4,820,601 A | 4/1989 | Ong et al. |
| 4,822,704 A | 4/1989 | Akasaki et al. |
| 4,833,054 A | 5/1989 | Akasaki et al. |
| 4,835,081 A | 5/1989 | Ong et al. |
| 4,842,971 A | 6/1989 | Sugaiwa et al. |
| 4,845,263 A | 7/1989 | Ong et al. |
| 4,868,080 A | 9/1989 | Umehara et al. |
| 4,895,781 A | 1/1990 | Takai |
| 4,921,769 A | 5/1990 | Yuh et al. |
| 4,925,757 A | 5/1990 | Takenouchi et al. |
| 4,942,106 A | 7/1990 | Takai et al. |
| 4,943,501 A | 7/1990 | Kinoshita et al. |
| 4,948,911 A | 8/1990 | Bugner et al. |
| 4,990,634 A | 2/1991 | Mukai et al. |
| 4,997,737 A | 3/1991 | Bugner et al. |
| 5,011,757 A | 4/1991 | Akasaki et al. |
| 5,011,969 A | 4/1991 | Akasaki et al. |
| 5,017,645 A | 5/1991 | Ong et al. |
| 5,023,356 A | 6/1991 | Mukai et al. |
| 5,028,505 A | 7/1991 | Akasaki et al. |
| 5,034,294 A | 7/1991 | Go et al. |
| 5,053,302 A | 10/1991 | Makino et al. |
| 5,075,189 A | 12/1991 | Ichino et al. |
| 5,075,487 A | 12/1991 | Akasaki et al. |
| 5,077,164 A | 12/1991 | Ueda et al. |
| 5,080,991 A | 1/1992 | Ono et al. |
| 5,102,757 A | 4/1992 | Akasaki et al. |
| 5,132,190 A | 7/1992 | Yamada et al. |
| 5,153,085 A | 10/1992 | Akasaki et al. |
| 5,158,847 A | 10/1992 | Go et al. |
| 5,166,016 A | 11/1992 | Badesha et al. |
| 5,168,024 A | 12/1992 | Yamamoto et al. |
| 5,194,355 A | 3/1993 | Ohmura et al. |
| 5,213,924 A | 5/1993 | Sakamoto |
| 5,235,104 A | 8/1993 | Yamada et al. |
| 5,286,589 A | 2/1994 | Go et al. |
| 5,308,726 A | 5/1994 | Hirano et al. |
| 5,324,604 A | 6/1994 | Bugner et al. |
| 5,336,577 A | 8/1994 | Spiewak et al. |
| 5,356,746 A | 10/1994 | Sugiyama et al. |
| 5,389,481 A | 2/1995 | Saita et al. |
| 5,413,885 A | 5/1995 | Datta et al. |
| 5,435,991 A | 7/1995 | Golman et al. |
| 5,437,950 A | 8/1995 | Yu et al. |
| 5,492,784 A | 2/1996 | Yoshikawa et al. |
| 5,501,927 A | 3/1996 | Imai et al. |
| 5,520,905 A | 5/1996 | Uhlmann et al. |
| 5,578,405 A | 11/1996 | Ikegami et al. |
| 5,658,702 A | 8/1997 | Nukada |
| 5,663,213 A | 9/1997 | Jones et al. |
| 5,677,095 A | 10/1997 | Kikuchi et al. |
| 5,698,141 A | 12/1997 | Kumar |
| 5,698,355 A | 12/1997 | Imai et al. |
| 5,723,072 A | 3/1998 | Kumar |
| 5,744,267 A | 4/1998 | Meerholz et al. |
| 5,780,194 A | 7/1998 | Katsukawa et al. |
| 5,795,690 A | 8/1998 | Takegawa et al. |
| 5,834,144 A | 11/1998 | Kim et al. |
| 5,871,877 A | 2/1999 | Ong et al. |
| 5,874,193 A | 2/1999 | Liu et al. |
| 5,916,719 A | 6/1999 | Kim et al. |
| 5,942,359 A | 8/1999 | Kinoshita et al. |
| 6,004,724 A | 12/1999 | Yamato et al. |
| 6,036,946 A | 3/2000 | Greene |
| 6,187,493 B1 | 2/2001 | Katsukawa et al. |
| 6,194,110 B1 | 2/2001 | Hsiao et al. |
| 6,287,737 B1 | 9/2001 | Ong et al. |
| 6,322,941 B1 | 11/2001 | Hsiao et al. |
| 6,465,648 B1 | 10/2002 | Tadokoro et al. |
| 6,485,886 B1 | 11/2002 | Yamato et al. |
| 6,544,701 B2 | 4/2003 | Tadokoro et al. |
| 6,558,851 B1 | 5/2003 | Fjeldstad et al. |
| 6,586,148 B1 | 7/2003 | Graham et al. |
| 6,656,650 B1 | 12/2003 | Lin et al. |
| 6,756,169 B2 | 6/2004 | Lin et al. |
| 6,770,410 B2 | 8/2004 | Yu et al. |
| 6,800,274 B2 | 10/2004 | Bonda et al. |
| 6,806,024 B1 | 10/2004 | Kura et al. |
| 6,849,367 B2 | 2/2005 | Shoshi et al. |
| 6,858,363 B2 | 2/2005 | Belknap et al. |
| 6,890,693 B2 | 5/2005 | Zhu et al. |
| 6,899,984 B2 | 5/2005 | Tokarski et al. |
| 6,905,804 B2 | 6/2005 | Law et al. |
| 6,919,473 B2 | 7/2005 | Bonda et al. |
| 6,926,887 B2 | 8/2005 | Bonda et al. |
| 6,946,226 B2 | 9/2005 | Wu et al. |
| 6,946,227 B2 | 9/2005 | Lin et al. |
| 6,955,869 B2 | 10/2005 | Jubran et al. |
| 6,962,692 B2 | 11/2005 | Bonda et al. |
| 6,964,833 B2 | 11/2005 | Tokarski et al. |
| 6,991,880 B2 | 1/2006 | Tong et al. |
| 7,011,917 B2 | 3/2006 | Jubran et al. |
| 7,029,812 B2 | 4/2006 | Tokarski et al. |
| 7,037,630 B2 | 5/2006 | Vong et al. |
| 7,037,632 B2 | 5/2006 | Jubran et al. |
| 7,045,263 B2 | 5/2006 | Zhu et al. |
| 7,045,264 B2 | 5/2006 | Yokota et al. |
| 7,056,632 B2 | 6/2006 | Ioannidis |
| 7,063,928 B2 | 6/2006 | Law et al. |
| 7,067,230 B2 | 6/2006 | Cammack et al. |
| 7,070,892 B2 | 7/2006 | Bender et al. |
| 7,070,894 B2 | 7/2006 | Bender et al. |
| 7,078,139 B2 | 7/2006 | Yokota et al. |
| 7,090,953 B2 | 8/2006 | Getautis et al. |
| 7,094,510 B2 | 8/2006 | Jubran et al. |
| 7,115,348 B2 | 10/2006 | Zhu et al. |
| 7,126,013 B2 | 10/2006 | Heeney et al. |
| 7,129,012 B2 | 10/2006 | Sekiya et al. |
| 7,163,771 B2 | 1/2007 | Ioannidis et al. |
| 7,172,843 B2 | 2/2007 | Lee et al. |
| 7,175,958 B2 | 2/2007 | Shoshi et al. |

(56) References Cited

U.S. PATENT DOCUMENTS

| | | | |
|---|---|---|---|
| 7,183,026 B2 | 2/2007 | Zhu et al. |
| 7,205,080 B2 | 4/2007 | Iwasaki et al. |
| 7,223,507 B2 | 5/2007 | Ioannidis et al. |
| 7,232,633 B2 | 6/2007 | Qi et al. |
| 7,235,587 B2 | 6/2007 | Bonda et al. |
| 7,244,541 B2 | 7/2007 | Tokarski et al. |
| 7,291,431 B2 | 11/2007 | Tokarski et al. |
| 7,291,432 B2 | 11/2007 | Lin et al. |
| 7,297,458 B2 | 11/2007 | Belknap et al. |
| 7,312,007 B2 | 12/2007 | Lin et al. |
| 7,326,511 B2 | 2/2008 | Matsumoto et al. |
| 7,354,534 B2 | 4/2008 | Lee et al. |
| 7,357,919 B2 | 4/2008 | Candau |
| 7,357,920 B2 | 4/2008 | Candau |
| 7,390,601 B2 | 6/2008 | Wu et al. |
| 7,396,622 B2 | 7/2008 | Nagasaka et al. |
| 7,431,917 B2 | 10/2008 | Candau |
| 7,491,989 B2 | 2/2009 | Loutfy et al. |
| 7,501,216 B2 | 3/2009 | Jubran et al. |
| 7,544,350 B2 | 6/2009 | Bonda et al. |
| 7,544,453 B2 | 6/2009 | Freeman et al. |
| 7,560,161 B2 | 7/2009 | Qi et al. |
| 7,588,702 B2 | 9/2009 | Bonda et al. |
| 7,592,113 B2 | 9/2009 | Nagasaka et al. |
| 7,597,825 B2 | 10/2009 | Bonda et al. |
| 7,745,083 B2 | 6/2010 | Nagasaka et al. |
| 7,776,614 B2 | 8/2010 | Bonda |
| 7,799,317 B2 | 9/2010 | Bonda et al. |
| 7,893,192 B2 | 2/2011 | Sasaki et al. |
| 7,928,249 B2 | 4/2011 | Marks et al. |
| 7,981,402 B2 | 7/2011 | Bonda et al. |
| 8,119,107 B2 | 2/2012 | Müller et al. |
| 8,236,469 B2 | 8/2012 | Belknap et al. |
| 9,125,829 B2 * | 9/2015 | Bonda ................... A61K 8/40 |
| 9,145,383 B2 * | 9/2015 | Bonda ................. C07D 335/12 |
| 9,611,246 B2 | 4/2017 | Bonda et al. |
| 2002/0102484 A1 | 8/2002 | Miyamoto et al. |
| 2003/0013028 A1 | 1/2003 | Tadokoro et al. |
| 2003/0190540 A1 | 10/2003 | Shoshi et al. |
| 2003/0194626 A1 | 10/2003 | Zhu et al. |
| 2003/0198880 A1 | 10/2003 | Law et al. |
| 2003/0211413 A1 | 11/2003 | Lin et al. |
| 2003/0228534 A1 | 12/2003 | Zhu |
| 2003/0232261 A1 | 12/2003 | Tokarski et al. |
| 2003/0232264 A1 | 12/2003 | Tokarski et al. |
| 2003/0235771 A1 | 12/2003 | Yokota et al. |
| 2004/0013960 A1 | 1/2004 | Lim et al. |
| 2004/0018439 A1 | 1/2004 | Tong et al. |
| 2004/0018440 A1 | 1/2004 | Lin et al. |
| 2004/0043313 A1 | 3/2004 | Zhu et al. |
| 2004/0043314 A1 | 3/2004 | Jubran et al. |
| 2004/0057912 A1 | 3/2004 | Bonda et al. |
| 2004/0057914 A1 | 3/2004 | Bonda et al. |
| 2004/0057916 A1 | 3/2004 | Bonda et al. |
| 2004/0062726 A1 | 4/2004 | Bonda et al. |
| 2004/0063011 A1 | 4/2004 | Lin et al. |
| 2004/0081903 A1 | 4/2004 | Tokarski et al. |
| 2004/0086796 A1 | 5/2004 | Yu et al. |
| 2004/0096761 A1 | 5/2004 | Lin et al. |
| 2004/0101772 A1 | 5/2004 | Zhu et al. |
| 2004/0101773 A1 | 5/2004 | Zhu et al. |
| 2004/0137345 A1 | 7/2004 | Yokota et al. |
| 2004/0142257 A1 | 7/2004 | Ioannidis |
| 2004/0142260 A1 | 7/2004 | Lee et al. |
| 2004/0151996 A1 | 8/2004 | Vong et al. |
| 2004/0161685 A1 | 8/2004 | Getautis et al. |
| 2004/0170909 A1 | 9/2004 | Jubran et al. |
| 2004/0176560 A1 | 9/2004 | Heeney et al. |
| 2004/0197685 A1 | 10/2004 | Ioannidis et al. |
| 2004/0197686 A1 | 10/2004 | Belknap et al. |
| 2004/0200999 A1 | 10/2004 | Cammack et al. |
| 2004/0241562 A1 | 12/2004 | Jubran et al. |
| 2004/0242841 A1 | 12/2004 | Cammack et al. |
| 2005/0042533 A1 | 2/2005 | Wu et al. |
| 2005/0051758 A1 | 3/2005 | Yamamoto et al. |
| 2005/0069793 A1 | 3/2005 | Jubran et al. |
| 2005/0069795 A1 | 3/2005 | Jubran et al. |
| 2005/0069796 A1 | 3/2005 | Iwasaki et al. |
| 2005/0069798 A1 | 3/2005 | Jubran et al. |
| 2005/0089789 A1 | 4/2005 | Zhu |
| 2005/0112487 A1 | 5/2005 | Shoshi et al. |
| 2005/0123849 A1 | 6/2005 | Law et al. |
| 2005/0153244 A1 | 7/2005 | Matsumoto et al. |
| 2005/0164106 A1 | 7/2005 | Bender et al. |
| 2005/0172422 A1 | 8/2005 | Kravtchenko et al. |
| 2005/0175913 A1 | 8/2005 | Bender et al. |
| 2005/0214664 A1 | 9/2005 | Lin et al. |
| 2005/0222307 A1 | 10/2005 | Bonda et al. |
| 2005/0238974 A1 | 10/2005 | Sekiya et al. |
| 2005/0287453 A1 | 12/2005 | Ioannidis et al. |
| 2005/0287454 A1 | 12/2005 | Belknap et al. |
| 2006/0002869 A1 | 1/2006 | Bonda et al. |
| 2006/0029803 A1 | 2/2006 | Qi et al. |
| 2006/0029872 A1 | 2/2006 | Qi et al. |
| 2006/0057480 A1 | 3/2006 | Lin et al. |
| 2006/0083698 A1 | 4/2006 | Candau |
| 2006/0083699 A1 | 4/2006 | Candau |
| 2006/0104924 A1 | 5/2006 | Candau |
| 2006/0127794 A1 | 6/2006 | Tokarski et al. |
| 2006/0142444 A1 | 6/2006 | Lee et al. |
| 2006/0147827 A1 | 7/2006 | Tokarski et al. |
| 2006/0210898 A1 | 9/2006 | Jubran |
| 2006/0257338 A1 | 11/2006 | Bonda et al. |
| 2006/0286470 A1 | 12/2006 | Wu et al. |
| 2006/0292469 A1 | 12/2006 | Nagasaka et al. |
| 2007/0023747 A1 | 2/2007 | Loutfy et al. |
| 2007/0026331 A1 | 2/2007 | Lee et al. |
| 2007/0077505 A1 | 4/2007 | Lin et al. |
| 2007/0082283 A1 | 4/2007 | Freeman et al. |
| 2007/0148571 A1 | 6/2007 | Iwasaki et al. |
| 2007/0213503 A1 | 9/2007 | Sasaki et al. |
| 2008/0075921 A1 | 3/2008 | Tateishi |
| 2008/0193793 A1 | 8/2008 | Johannes et al. |
| 2008/0194821 A1 | 8/2008 | Johannes et al. |
| 2008/0233499 A1 | 9/2008 | Nagasaka et al. |
| 2008/0286693 A1 | 11/2008 | Matsumoto et al. |
| 2008/0305417 A1 | 12/2008 | Sugimura et al. |
| 2009/0036643 A1 | 2/2009 | Marks et al. |
| 2009/0039323 A1 | 2/2009 | Bonda et al. |
| 2009/0297218 A1 | 12/2009 | Nagasaka et al. |
| 2010/0143272 A1 | 6/2010 | Müller et al. |
| 2010/0294368 A1 | 11/2010 | Ushiro et al. |
| 2011/0033396 A1 | 2/2011 | Bonda et al. |
| 2011/0037063 A1 | 2/2011 | Buesing et al. |
| 2011/0143273 A1 | 6/2011 | Sekido et al. |
| 2011/0195353 A1 | 8/2011 | Belknap et al. |
| 2011/0251242 A1 | 10/2011 | Bonda et al. |
| 2011/0268472 A1 | 11/2011 | Sekido et al. |
| 2012/0121524 A1 | 5/2012 | Müller et al. |
| 2014/0044654 A1 | 2/2014 | Bonda et al. |
| 2015/0164852 A1 | 6/2015 | Bonda et al. |
| 2016/0002200 A1 | 1/2016 | Bonda et al. |
| 2016/0022555 A1 | 1/2016 | Bonda et al. |
| 2016/0024046 A1 | 1/2016 | Bonda et al. |

FOREIGN PATENT DOCUMENTS

| | | |
|---|---|---|
| EP | 0351887 | 1/1990 |
| EP | 0761201 | 3/1997 |
| EP | 0761214 | 3/1997 |
| EP | 1661548 | 5/2006 |
| EP | 2070550 | 6/2009 |
| JP | H1048554 | 2/1998 |
| JP | H1048854 | 2/1998 |
| JP | 2000162798 | 6/2000 |
| JP | 2005139263 | 6/2005 |
| JP | 2010127963 | 6/2010 |
| WO | 0061585 | 10/2000 |
| WO | 03045942 | 6/2003 |
| WO | 2004047821 | 6/2004 |
| WO | 2004110394 | 12/2004 |
| WO | WO 2004/110394 | * 12/2004 ............. A61Q 17/04 |
| WO | 2005048944 | 6/2005 |
| WO | 2006034968 | 4/2006 |

(56) References Cited

FOREIGN PATENT DOCUMENTS

| WO | 2009020673 | 2/2009 |
|---|---|---|
| WO | 2009020676 | 2/2009 |
| WO | 2014026151 | 2/2014 |

OTHER PUBLICATIONS

Latif, et al., "Cyano esters and malonoitriles. V. Cyano(fluorenyl)acetic esters, hydroxyl nitriles and benzimidazolylacetonitriles." Australian Journal of Chemistry (1977), 30(10), 2263-9.

Hafez, et al., "Carbonyl and thiocarbonyl compounds. V. Synthesis of Newer Unsaturated Nitriles, Carboxylic Acids, and Esters Derived from Xanthene and Thiaxanthene." Journal of Organic Chemistry (1961), 26, 3988-91.

Latif, et al., "Cleavage of Xanthene Ethers. A New Route to 9-substituted Xanthenes." Canadian Journal of Chemistry (1964), 42(7), 1736-40.

Zeid, et al., "Reactions of 4-chloro-9H-xanthene-9-thione with tetrachloro-o-benzoquinone." Liebigs Annlen der Chemie (1984), 1, 196-8.

P.R. Droupadi et al. "Charge Transfer Complexes of Pheophytin A with Nitroaromatics. Electron Transfer from Excited Singlet of Pheophytin A to Nitroaromatics", Photochemistry and Photobiology, vol. 39, No. 2, Feb. 1, 1984, pp. 161-167, XP055072972.

Erich Schonberg et al, "Uber Aminale des Flourenons and Erivate des 9-Amino-fluorens", Chemische Berichte, vol. 98, No. 3, Mar. 31, 1965 pp. 812-819, XP055240079.

Jing Li et al, "Synthesis of New C2-Symmetric Fluoren-9-ylidene Malonate Derived Bis(oxazoline) Ligands and Their Application in Friedel-Crafts Reactions", Molecules, vol. 15, No. 12, Nov. 26, 2010, pp. 8582-8592, KP055240050.

Naela Assadi et al, "Overcrowded naphthologs of mono-bridged tetraarylethylenes: analogs of bistricyclic aromatic enes", Structural Chemistry, Kluwer Academic Publishers-Plenum Publishers, NE vol. 20, No. 4, May 13, 2009, pp. 541-556, XP019688913.

M.M. Sidky et al, "Action of Triphenylphosphine on some Episulphides; a new Method for the Synthesis of Thermochromic Ethylenes", Journal Fuer Praktische Chemie, vol. 312, No. 1, Jan. 1, 1970, pp. 51-54, XP055240149.

Nishino et al, "Manganese (III)-Mediated Carbon-Carbon Bond Formation in the Reaction of Xanthense With Active Methylene Compounds" The Journal of Organic Chemistry, American Chemical Society, US, vol. 57, Jan. 1, 1992, pp. 3551-3557, XP000984589.

Xiaojie Zhang et al, "Synthesis, Self-Assembly, and Charge Transporting Property of Contorted Tetrabenzocoronenes", The Journal of Organic Chemistry, vol. 75, No. 23, Dec. 3, 2010, pp. 3069-8077, XP055240158.

Ruirui Zhang et al, "Multifuntional Core-Shell Nanoparticles as Highly Efficient Imaging and Photosensitizing Agents", Langmuir, vol. 25, No. 17, Sep. 1, 2009, pp. 10153-10158, XP055240180, New York, NY.

Tapan K. Mukherjee et al "9-Dicyanomethylene-2, 4, 7-Trinitrofluorene, A New Electron Acceptor", The Journal of Organic Chemistry, vol. 30, No. 2, Feb. 1, 1965, pp. 644-646, XP055240094.

Extended European Search Report dated Jan. 21, 2016 in corresponding European Patent Application No. 13827223.2.

Walter et al., Porphyrins and phthalocyanines in solar photovoltaic cells, J. Porphyrins Phthalocyanines, 14:759-92 (Jul. 2010).

Worlikar et al., Palladium-catalyzed synthesis of 9-fluorenylidenes through aryne annulation, Org. Lett., 11 (11):2413-6 (Jun. 4, 2009).

Caira et al., Acta Crys. Sec. C, Oct. 1984, C40(10), pp. 1710-1712.

Jones et al., Tetrahedron, Sep. 1966, 22(9), pp. 3021-3026.

International Preliminary Report on Patentability and Written Opinion from corresponding PCT/US2013/054408 dated Feb. 10, 2015.

International Preliminary Report on Patentability and Written Opinion from corresponding PCT/US2012/067519 dated Feb. 10, 2015.

Examination report from co-pending Australian application No. 2013299403 dated Apr. 18, 2016.

Examination report from co-pending Australian application No. 2013299403 dated Apr. 18, 2017.

Hirakawa et al., J. Org. Chem., Apr. 1986, 51(7), pp. 1083-1087.

First Official Action from Chinese Patent Application No. 201380053282.5. dated Dec. 22, 2015.

Second Official Action from Chinese Patent Application No. 201380053282.5 dated Jul. 1, 2016.

Third Official Action from Chinese Patent Application No. 201380053282.5 dated Jan. 25, 2017.

Extended European search report from co-pending European application No. 13827223.2 dated Jan. 21, 2016.

International Search Report and Written Opinion of the International Searching Authority for co-pending PCT application No. PCT/US2012/067519 dated Nov. 18, 2013.

James Kennedy & Roy Pottier, Endogenous Protoporphyrin IX, a Clinically Useful Photosensitizer for Photodynamic Therapy, 14 J Photochem. Photobiol. B: Biol. 275 (Jan. 1992).

Chemistry of Porphyrins, 7 pages, downloaded from the Internet Jul. 12, 2012: <http://www.org-chem.org/yuuki/ porphyrin/porphyrin.html>.

Lin et al., Inhibition of hepadnavirus reverse transcriptase-epsilon RNA interaction by porphyrin compounds, J. Virol., 82(5):2305-12 (Mar. 2008).

National Cancer Institute, Antioxidants and Cancer Prevention: Fact Sheet (Jul. 28, 2004).

Photodynamic Therapy, downloaded from the Internet <http://en.wikipedia.orq/wiki/photodynamic_therapy> (last modified Mar. 9, 2013).

* cited by examiner

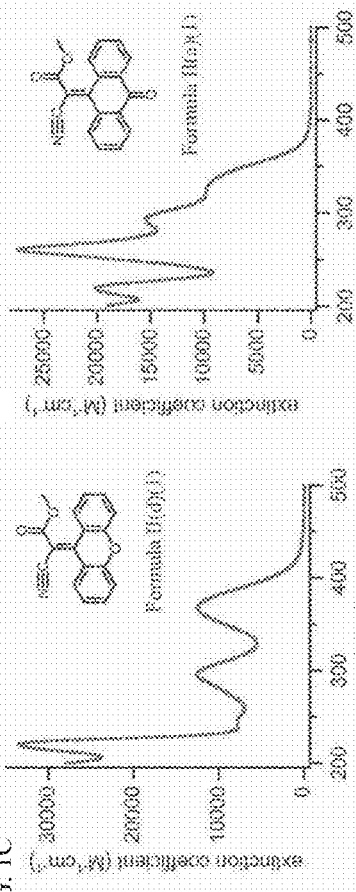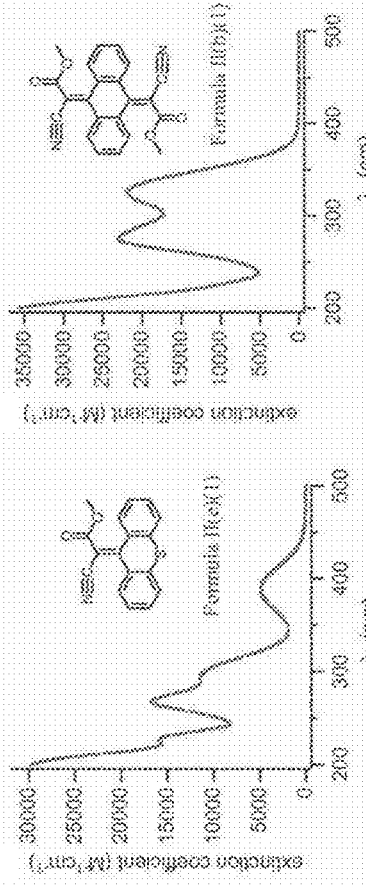
FIG. 1 (cont.)

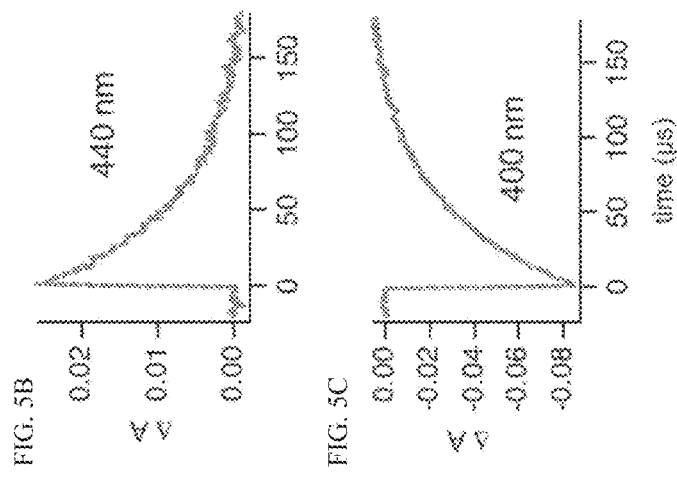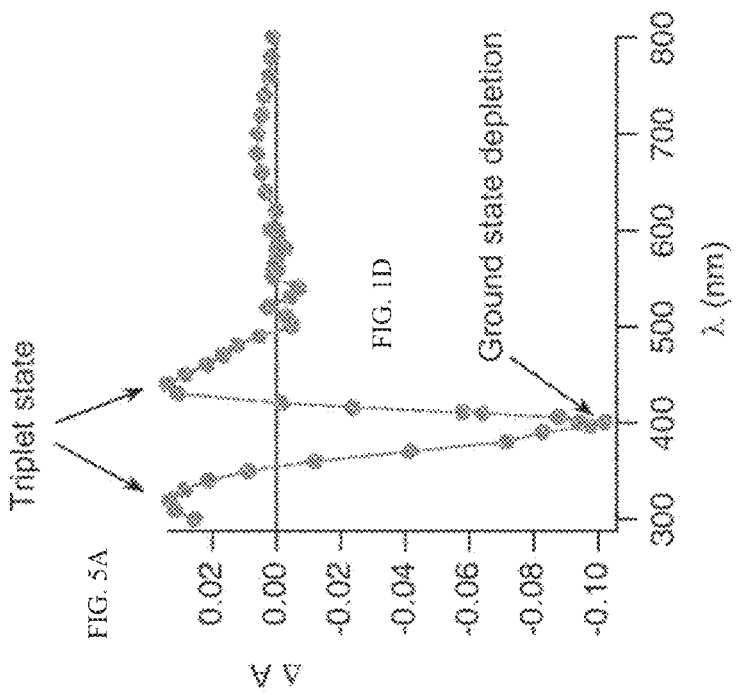

FIG. 18A
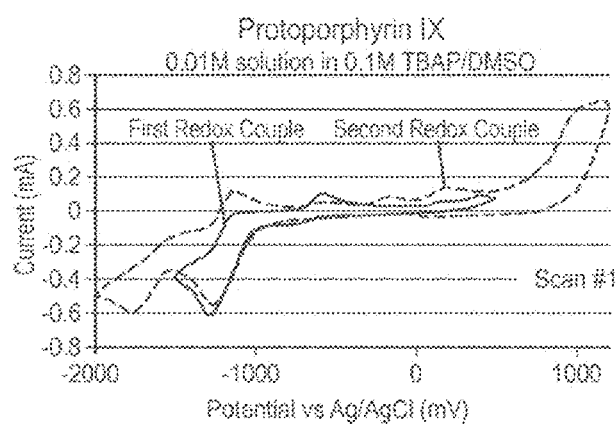
FIG. 18B
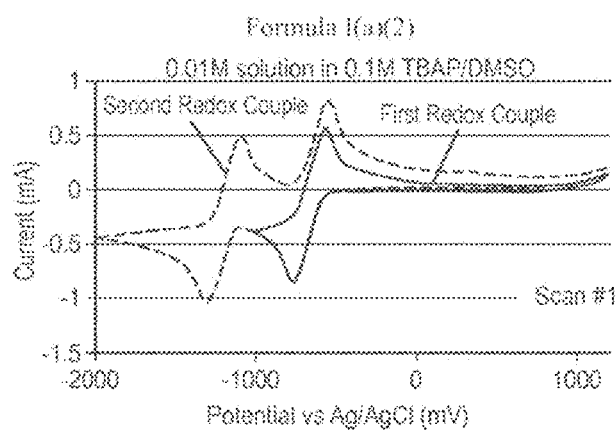
FIG. 18

FIG. 18C
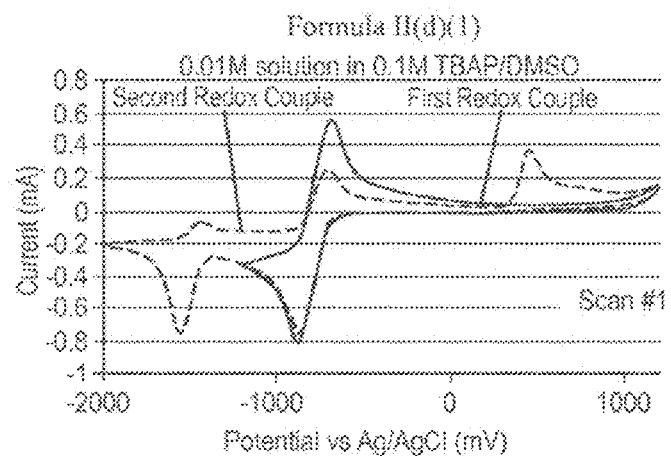
FIG. 18D
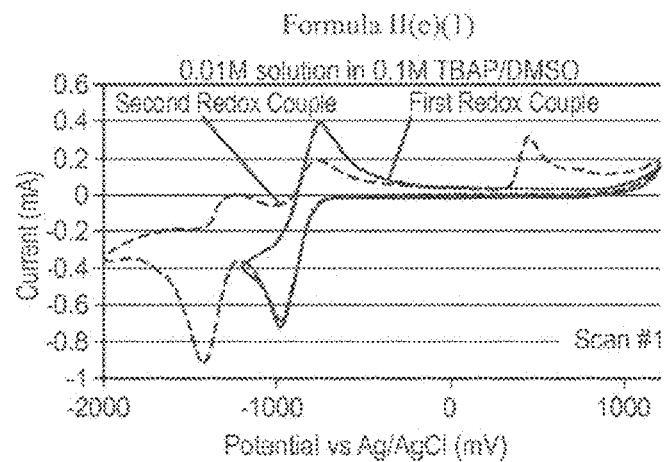
FIG. 18 (cont.)

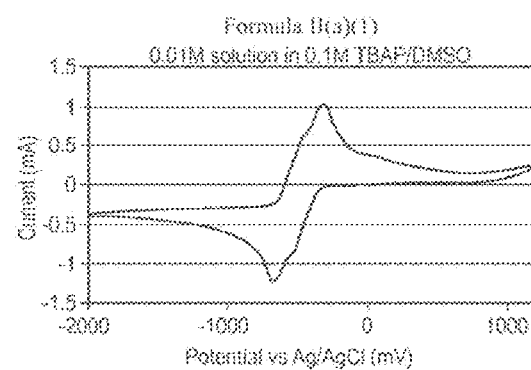
FIG. 18E
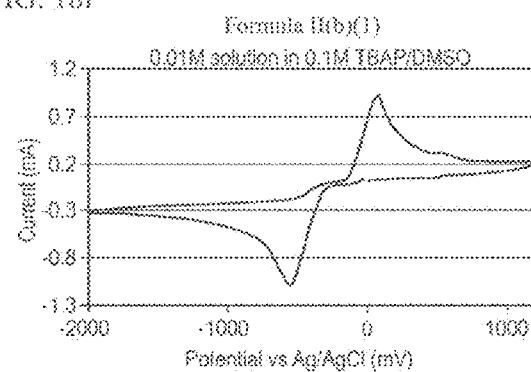
FIG. 18F
FIG. 18 (cont.)

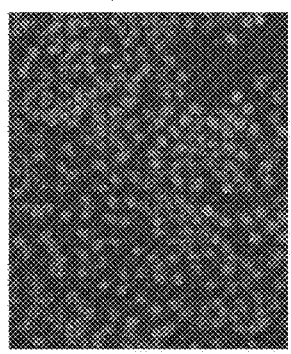 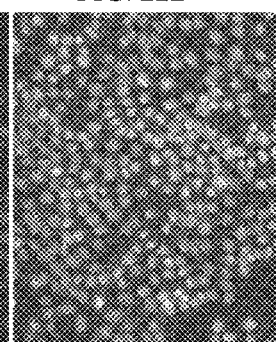 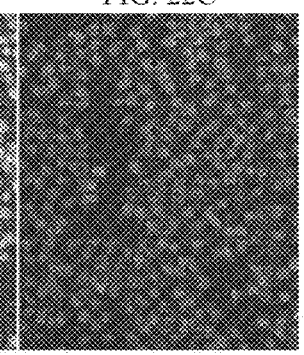
FIG. 22A     FIG. 22B     FIG. 22C
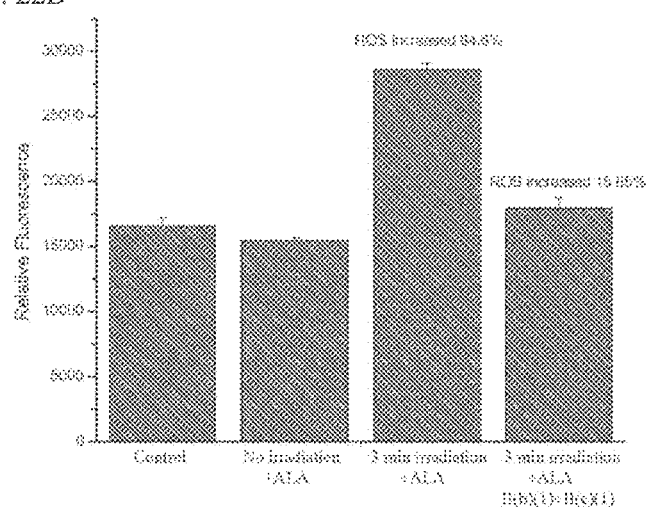
FIG. 22D
FIG. 22

COMPOSITIONS, APPARATUS, SYSTEMS, AND METHODS FOR RESOLVING ELECTRONIC EXCITED STATES

CROSS-REFERENCE TO RELATED APPLICATIONS

This application is a division of U.S. application Ser. No. 13/963,865 filed Aug. 9, 2013. U.S. application Ser. No. 13/963,865 is a continuation-in-part of U.S. application Ser. No. 13/588,662 filed Aug. 17, 2012, a continuation-in-part of International PCT Application No. PCT/US12/67519 filed Dec. 3, 2012 and a continuation-in-part of U.S. application Ser. No. 13/805,168 filed Dec. 18, 2012. U.S. application Ser. No. 13/963,865 also claims priority to U.S. Provisional Patent Application No. 61/681,916, filed on Aug. 10, 2012. The contents of all of the above applications are hereby incorporated in their entirety by reference.

FIELD OF THE DISCLOSURE

The present disclosure relates, in some embodiments, to molecules, including conjugated fused polycyclic molecules, that may receive excited state energy from other molecules (e.g., light-absorbing molecules) or directly from the irradiation sources. According to some embodiments, the present disclosure relates to molecules, including conjugated fused polycyclic molecules, that may quench, dissipate, and/or otherwise resolve excited state energy, normally by way of releasing it as heat. (e.g., as heat).

BACKGROUND OF THE DISCLOSURE

Irradiation energy can have a detrimental impact on exposed substances and organisms. When a molecule absorbs light, the absorbed photon may propel an electron from a lower energy orbital (e.g., ground state) to a higher energy orbital (e.g., excited state). A molecule with an excited electron may be unstable; it may readily react with surrounding molecules to release the excited state energy and return its electron to a lower energy state. The manner in which the excited energy state is resolved may have a substantial impact on the ultimate effect of the absorption event. For example, photosynthetic organisms can harvest the absorbed energy and convert it to usable chemical energy. In many cases, however, excited state energy is resolved in less productive and even detrimental ways. For example, reactive oxygen species and other reactive free radicals may be formed. These highly reactive species often react by oxidizing one or more surrounding molecules. The resulting damage may vary in kind and extent. Other consequences of reactions resulted from excited state molecule include: pigment molecules bleaching, polymers degradation, DNA mutation. plasma membranes damage, and ectopically and/or deleteriously activation of intracellular signaling.

SUMMARY

Accordingly, a need has arisen for improved compositions, apparatus, systems, and methods for resolving electronic excited states. The present disclosure relates, according to some embodiments, to compositions, apparatus, systems, and methods for resolving electronic excited states (e.g., quenching singlet and triplet electronic excited states). For example, a method may comprise resolving an excited state of a chromophore (e.g., a chromophore commonly found in polymeric materials and in organic colorants) by contacting the chromophore and a conjugated fused tricyclic compound (e.g., a conjugated fused tricyclic compound having at least two electron withdrawing group. Upon contact, a tricyclic compound may quench singlet and/or triplet excited states of a chromophore by accepting an electron from the chromophore, thereby returning the chromophore back to the ground state, in some embodiments. A molecule (e.g., photolabile chromophore moiety) may reach an excited state when illuminated by visible and/or UV radiation at a wavelength in the range of about 290 to about 800 nm, commonly found in sunlight. When an excited molecule (e.g., an excited chromophore in polymeric molecule and organic colorant) interacts with a conjugated fused tricyclic compound having at least two electron withdrawing groups, the excited molecule is returned to the ground state and photostabilized. Further, when an excited molecule interacts with a conjugated fused tricyclic compound having at least two electron withdrawing groups, the excited state of the molecule is effectively quenched substantially before it can react interact with oxygen, preventing the generation of reactive oxygen species.

The present disclosure relates, in some embodiments, to conjugated fused polycyclic molecules and compositions for resolving an electronically excited state. A composition may comprise, for example, a photoactive molecule and/or a photosensitizer. A composition may further comprise a conjugated fused polycyclic molecule having a structure according to Formula I:

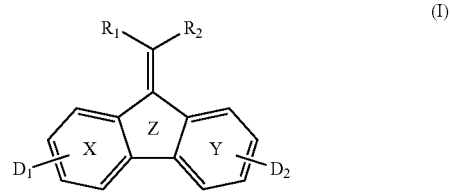

wherein
$R_1$ independently may be nitrile, $C(O)R_3$, $C(O)N(R_4)R_5$, $C(O)$—$S$—$R_6$, or fused aryl,
$R_2$ independently may be nitrile, $C(O)R_7$ $C(O)N(R_8)R_9$, $C(O)$—$S$—$R_{10}$, or fused aryl,
$R_3$, $R_4$, $R_5$, $R_6$, $R_7$, $R_8$, $R_9$, and $R_{10}$ each independently may be H, aryl, substituted aryl, fused aryl, alkyl, substituted alkyl, or branched alkyl,
$D_1$ independently may be H, hydroxyl, or $R_{11}$,
$D_2$ independently may be H, hydroxyl, or $R_{12}$, and
$R_{11}$ and $R_{12}$ each independently may be H, alkyl, heteroalkyl, alkoxyl, heteroalkoxyl, aryl, heteroaryl, or fused aryl,
provided that
  $R_1$ and $R_2$ are not both nitrile,
  $R_1$ and $R_2$ are not fused to each other,
  $R_{11}$ and $R_{12}$ do not comprise azo,
  the fused tricyclic moiety defined by rings X, Y, and Z is the only tricyclic moiety in the molecule, and/or
  $D_1$ and $D_2$ are not fused to each other.
In some embodiments, a conjugated fused polycyclic molecule according to Formula I may be configured (a) to resolve at least one excited state of a photoactive molecule substantially without observable photochemical reactions, (b) to resolve at least one excited state of a photoactive molecule substantially non-radiatively, or (c) to resolve at least one excited state of a photoactive molecule substantially without observable photochemical reactions and substantially non-radiatively. In some embodiments, a conjugated fused polycyclic molecule according to Formula I may be configured (a) to resolve at least one excited state of a photosensitizer molecule substantially without observable photosensitization reactions, (b) to resolve at least one excited state of a photosensitizer molecule substantially non-radiatively, or (c) to resolve at least one excited state of a photosensitizer molecule substantially without observable photosensitization reactions and substantially non-radiatively.

According to some embodiments, $R_1$ and $R_2$ may be different from each other. $D_1$ and $D_2$ may be hydrogen, in some embodiments. $R_3$, $R_4$, $R_5$, $R_6$, $R_7$, $R_8$, $R_9$, and $R_{10}$, in some embodiments, may be each independently an alkyl group having from about 1 to about 30 carbon atoms. In some embodiments, $R_1$ and $R_2$ are both nitrile and, in some embodiments, neither $R_1$ nor $R_2$ is nitrile. A conjugated fused polycyclic molecule of Formula I may comprise no more than 4 rings fused to each other and/or no more than 6 rings total, according to some embodiments.

In some embodiments, a composition may comprise a conjugated fused polycyclic molecule having a structure according to Formula II:

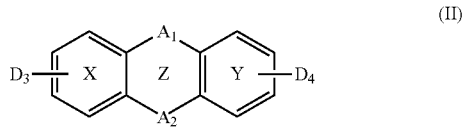

(II)

wherein
  $A_1$ independently may be carbonyl, $C=C(R_{13})R_{14}$, O, S, S=O, S(O)=O, C=S,
  $R_{13}$ independently may be nitrile, $C(O)OR_{15}$, $C(O)R_{16}$, $C(O)N(R_n)R_{18}$, $C(O)$—S—$R_{19}$, aryl, substituted or fused aryl,
  $R_{14}$ independently may be nitrile, $C(O)OR_{20}$, $C(O)R_{21}$, $C(O)N(R_{22})R_{23}$, $C(O)$—S—$R_{24}$, aryl, substituted or fused aryl,
  $R_{15}$, $R_{16}$, $R_{17}$, $R_{18}$, $R_{19}$, $R_{20}$, $R_{21}$, $R_{22}$, $R_{23}$, and $R_{24}$ each independently may be aryl, substituted aryl, fused aryl, alkyl, substituted alkyl, or branched alkyl,
  $A_2$ independently may be carbonyl, $C=C(R_n)R_{14}$, O, S, S=O, S(O)=O, C=S,
  $D_3$ independently may be H, hydroxyl, or $R_{25}$,
  $D_4$ independently may be H, hydroxyl, or $R_{26}$, and
  $R_{25}$ and $R_{26}$ each independently may be alkyl, heteroalkyl, alkoxyl, heteroalkoxyl, aryl, heteroaryl, or fused aryl,
provided that
  at least one of $A_1$ and $A_2$ is $C=C(R_{13})R_{14}$,
  if neither $A_1$ nor $A_2$ is S, for each $C=C(R_{13})R_{14}$, no more than one of $R_{13}$ and $R_{14}$ is nitrile (e.g., if both $A_1$ and $A_2$ are $C=C(R_{13})R_{14}$, no more than one of $R_{13}$ and $R_{14}$ of the $A_1$ group may be nitrile and no more than one of $R_n$ and $R_{14}$ of the $A_2$ group may be nitrile), and
  if either $A_1$ nor $A_2$ is O, for each $C=C(R_{13})R_{14}$, no more than one of $R_{13}$ and $R_{14}$ is $C(O)OR_{15/20}$ (e.g., $R_{14}$ cannot be $C(O)OR_{20}$ if $A_2$ is O and $R_{13}$ is $C(O)OR_{15}$).

In some embodiments, a conjugated fused polycyclic molecule according to Formula II may be configured (a) to resolve at least one excited state of a photoactive molecule substantially without observable photochemical reactions, (b) to resolve at least one excited state of a photoactive molecule substantially non-radiatively, or (c) to resolve at least one excited state of a photoactive molecule substantially without observable photochemical reactions and substantially non-radiatively. In some embodiments, a conjugated fused polycyclic molecule according to Formula II may be configured (a) to resolve at least one excited state of a photosensitizer molecule substantially without observable photosensitization reactions, (b) to resolve at least one excited state of a photosensitizer molecule substantially non-radiatively, or (c) to resolve at least one excited state of a photosensitizer molecule substantially without observable photosensitization reactions and substantially non-radiatively.

According to some embodiments, $R_{13}$ and $R_{14}$ may be different from each other. $D_3$ and $D_4$ may be hydrogen, in some embodiments. $R_{15}$, $R_{16}$, $R_{17}$, $R_{18}$, $R_{19}$, $R_{20}$, $R_{21}$, $R_{22}$, $R_{23}$, and $R_{24}$, in some embodiments, may be each independently an alkyl group having from about 1 to about 30 carbon atoms. In some embodiments, $R_{13}$ and $R_{14}$ are both nitrile and, in some embodiments, neither $R_{13}$ nor $R_{14}$ is nitrile. A conjugated fused polycyclic molecule of Formula II may comprise no more than 4 rings fused to each other and/or no more than 6 rings total, according to some embodiments.

In some embodiments, a composition may comprise a conjugated fused polycyclic molecule having a structure according to Formula III:

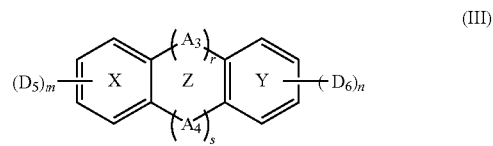

(III)

wherein
  m and n each independently may be 0, 1, 2, 3, or 4,
  r and s each may be 0 or 1,
  $A_3$ and $A_4$ each independently may be carbonyl, $C=C(R_{27})R_{28}$, O, S, S=O, S(O)=O, or C=S,
  $R_{27}$ independently may be nitrile, $C(O)OR_{29}$, $C(O)R_{30}$, $C(O)N(R_{31})R_{32}$, $C(O)$—S—$R_{33}$, $C(O)$—O—S—$R_{34}$, $C=CHR_{35}$, $N(R_{36})_3^+$, F, Cl, Br, I, $CF_3$, $CCl_3$, $NO_2$, aryl, substituted aryl, or fused aryl,
  $R_{28}$ independently may be nitrile, $C(O)OR_{37}$, $C(O)R_{38}$, $C(O)N(R_{39})R_{40}$, $C(O)$—S—$R_{41}$, $C(O)$—O—S—$R_{42}$, $C=CHR_{43}$, $N(R_{44})_3^+$, F, Cl, Br, I, $CF_3$, $CCl_3$, $NO_2$, aryl, substituted aryl, or fused aryl,
  $R_{29}$ and $R_{37}$ each independently may be H, alkyl, cycloalkyl, alkenyl, cycloalkenyl, alkynyl, aryl, substituted aryl, or fused aryl,
  $R_{30}$, $R_{31}$, $R_{32}$, $R_{33}$, $R_{34}$, $R_{35}$, $R_{38}$, $R_{39}$, $R_{40}$, $R_{41}$, $R_{42}$, and $R_{43}$ each independently may be H, alkyl, cycloalkyl, alkenyl, cycloalkenyl, alkynyl, or aryl, substituted aryl, or fused aryl, alkyl, substituted alkyl, or branched alkyl,
  $R_{36}$ and R each independently may be H or $C_1$-$C_6$ alkyl, and
  $D_5$ and $D_6$ may be independently $R_{27}$, $R_{28}$, heteroaryl, hydroxyl, alkyl, or alkoxyl, provided that
  r+s≥1, and
  at least one of $A_3$ and $A_4$ is $C=C(R_{27})R_{28}$.

In some embodiments, a conjugated fused polycyclic molecule according to Formula III may be configured (a) to resolve at least one excited state of a photoactive molecule substantially without observable photochemical reactions, (b) to resolve at least one excited state of a photoactive molecule substantially non-radiatively, or (c) to resolve at least one excited state of a photoactive molecule substantially without observable photochemical reactions and substantially non-radiatively. In some embodiments, a conjugated fused polycyclic molecule according to Formula III may be configured (a) to resolve at least one excited state of a photosensitizer molecule substantially without observable photosensitization reactions, (b) to resolve at least one excited state of a photosensitizer molecule substantially non-radiatively, or (c) to resolve at least one excited state of a photosensitizer molecule substantially without observable photosensitization reactions and substantially non-radiatively.

According to some embodiments, a photoactive molecule may selected from a pigment, a porphyrin, dibenzyolmethane, p-aminobenzoic acid, anthranilate, salicylate, cinnamic acid, dihydroxycinnamic acid, camphor, trihydroxycinnamic acid, dibenzalacetone naptholsulfonate, benzalacetophenone naphtholsulfonate, dihydroxy-naphthoic acid, o-hydroxydiphenyldisulfonate, p-hydroxdydiphenyldisulfonate, coumarin, respective salts thereof, respective derivatives thereof, and combinations thereof. A photoactive molecule may selected, in some embodiments, from coumarin and derivatives thereof; diazole derivatives; quinine derivatives and salts thereof; quinoline derivatives; hydroxyl-substituted benzophenone derivatives; naphthalate derivatives; methoxy-substituted benzophenone derivatives; uric acid derivatives; vilouric acid derivatives; tannic acid and derivatives thereof; hydroquinone; benzophenone derivatives; 1,3,5-triazine derivatives; phenyldibenzimidazole tetrasulfonate and salts and derivatives thereof; terephthalyidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; and combinations thereof.

A composition comprising a conjugated fused polycyclic molecule according to Formula I, II, and/or III may be formulated as a paint, a coating, a cosmetic, a sunscreen, a pharmaceutical preparation, a bituminous preparation, an ink, a toner, a photographic emulsion, a glass, or a fabric. For example, a paint may comprise a donor molecule and a sufficient quantity of acceptor molecules to resolve excited states that may arise in the donor molecules.

The present disclosure relates, in some embodiments, to methods for resolving at least one excited energy state of a photoactive molecule. For example, a method may comprise positioning a donor molecule (e.g., a photoactive molecule and/or a photosensitizer molecule) in electrical communication with a conjugated fused polycyclic molecule prior to, during, or following excitation of the photoactive molecule to the at least one excited energy state. A conjugated fused polycyclic molecule may have a structure according to Formula I, II, or III. In some embodiments, an exicted state of a donor molecule may be resolved substantially without observable photochemical reaction and/or substantially without observable photosensitization reactions. An exicted state of a donor molecule may be resolved substantially non-radiatively, according to some embodiments. A method may comprise, in some embodiments, resolving an excited state of a donor molecule substantially non-radiatively, substantially without observable photochemical reaction, and/or substantially without observable photosensitization reactions.

The present disclosure relates, in some embodiments, to methods for resolving (e.g., quenching) excited state energy from an excited donor (e.g., a porphyrin), for example, a donor that has been excited by absorption of light (e.g., light having a wavelength in the wavelength range of about 290 to about 800 nm). For example, a method may comprise reacting a donor molecule having a porphyrin moiety according to Formula IV:

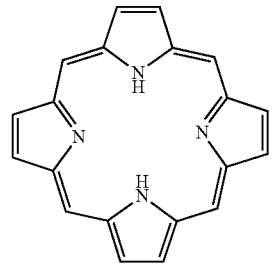

IV with a conjugated, fused polycyclic molecule having a structure according to Formula I, II, III, V, or a salt thereof. According to some embodiments, a conjugated, fused polycyclic molecule may have a structure according to Formula V:

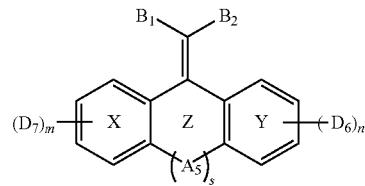

V wherein
  m and n each independently may be 0, 1, 2, 3, or 4,
  s independently may be 0 or 1,
  $A_5$ independently may be O, S, C=O, C=S,

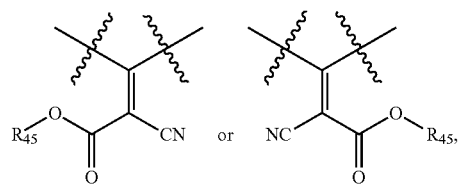

$B_1$, $B_2$, $D_7$, and $D_8$ are each independently F, Cl, Br, I, $CF_3$, $CCl_3$, $N(R_{46})_3^+$, $NO_2$, CN, C(=O)$R_{47}$, C(=O)O$R_{48}$, $SO_2R_{49}$, aryl, and —C=CHR$_{50}$,
  $R_{45}$, $R_{47}$, and $R_{48}$ each independently may be H, alkyl, alkenyl, alkynyl, cycloalkyl, cycloalkenyl, aryl, or amino,
  $R_{46}$ each independently may be H or $C_1$-$C_6$ alkyl,
  $R_{49}$ each independently may be H, O⁻, OH, $NH_2$, or Cl, and
  $R_{50}$ each independently may be alkyl, alkenyl, alkynyl, cycloalkyl, cycloalkenyl, or aryl.

An excited donor molecule may resolve to a lower energy state (e.g., its ground state) upon transferring its excited electron to a conjugated fused polycyclic molecule. In some embodiments, an excited donor molecule and/or a conjugated fused polycyclic molecule may be contained in a paint, a coating, a cosmetic, a sunscreen, a pharmaceutical preparation, a bituminous preparation, an ink, a toner, a photographic emulsion, a glass, and/or a fabric. A donor molecule (e.g., a porphyrin) may be contained in a mammalian cell. In some embodiments, one or more functional groups of Formula V may be as defined for Formulas I, II, or III including one or more exclusions. A molecule according to Formula V may have, in some embodiments, a molecular weight as set forth for Formulas I, II, or III. According to some embodiments, $R_{45}$ may not include cycloalkenyl.

According to some embodiments, the present disclosure relates to methods for suppressing (e.g., arresting) the formation of one or more of singlet oxygen and a reactive oxygen species (e.g., superoxide anion, peroxide, hydroxyl radical, hydroxyl ion) by an excited donor molecule (e.g., an excited pigment). A donor molecule may become an excited donor molecule upon absorption of light (e.g., light having a wavelength in the wavelength range of about 290 to about 800 nm). A method may comprise quenching the excited donor molecule with a conjugated, fused polycyclic molecule having a structure according to Formula I, II, III, V, or a salt thereof.

The present disclosure relates, in some embodiments, to methods for protecting skin from oxidative stress (e.g., caused by generation of free radical oxygen) comprising coating skin with a porphyrin excited state quencher capable of accepting or donating an electron from or to a porphyrin compound in the excited state and returning the excited porphyrin compound to its ground state. A porphyrin excited state quencher may comprise, in some embodiments, a conjugated, fused polycyclic molecule having a structure according to Formula I, II, III, V, or a salt thereof.

The present disclosure relates, according to some embodiments, to methods for protecting healthy cells adjacent to cancerous or pre-cancerous cells (e.g., cancerous or pre-cancerous cells undergoing photodynamic therapy) comprising contacting (e.g., applying) a composition comprising a porphyrin excited state quencher compound to the adjacent healthy cells in sufficient quantity to suppress (e.g., arrest) the formation of one or more of singlet oxygen and a reactive oxygen species in the adjacent healthy cells. A porphyrin excited state quencher may comprise, in some embodiments, a conjugated, fused polycyclic molecule having a structure according to Formula I, II, III, V, or a salt thereof.

Any desired amount of acceptor (e.g., conjugated, fused polycyclic molecule) may be used in a method of the disclosure. In some embodiments, the amount used may be related to (e.g., a function of, proportional to) the likely and/or expected exposure (e.g., duration, intensity, and/or wavelength) of a donor molecule (e.g., photoactive molecule and/or photosensitiser molecule) to potentially exciting radiation. The amount of acceptor used may be related, in some embodiments, to (e.g., a function of, proportional to) the likely and/or expected abundance of donor molecules (e.g., photoactive molecule and/or photosensitiser molecule) in a composition, object, or cell to be exposed to potentially exciting radiation.

Examples of acceptor molecules that may be be included in a composition and/or employed in one or more methods or the disclosure include one or more conjugated, fused polycyclic molecules according to Formula I(a)-I(j) and II(a)-II(bl) and any subset thereof. For example, a method for resolving at least one excited energy state of a donor molecule may comprise positioning a donor molecule in electrical communication with a conjugated, fused polycyclic molecule selected from Formula I(a)-I(j) and II(a)-II(bl) and any subset thereof.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein:

FIG. 1C illustrates an absorption spectra of an acceptor compound according to a specific example embodiment of the disclosure, Formula II(d)(1) in acetonitrile;

FIG. 1D illustrates an absorption spectra of an acceptor compound according to a specific example embodiment of the disclosure, Formula II(a)(1) in acetonitrile;

FIG. 1E illustrates an absorption spectra of an acceptor compound according to a specific example embodiment of the disclosure, Formula II(e)(1) in acetonitrile;

FIG. 1F illustrates an absorption spectra of an acceptor compound according to a specific example embodiment of the disclosure, Formulas II(b)(1) and II(c)(1) in acetonitrile;

FIG. 5A illustrates a transient absorption spectrum of an argon saturated acetonitrile solution of protoporphyrin IX, according to a specific example embodiment of the disclosure, recorded 0.1 to 1.5 μs after pulsed laser excitation (355 nm, 5 ns pulse width);

FIG. 5B illustrates a transient absorption spectrum of an argon saturated acetonitrile solution of protoporphyrin IX, according to a specific example embodiment of the disclosure, recorded 0.1 to 1.5 μs after pulsed laser excitation (440 nm, 5 ns pulse width);

FIG. 5C illustrates a transient absorption spectrum of an argon saturated acetonitrile solution of protoporphyrin IX, according to a specific example embodiment of the disclosure, recorded 0.1 to 1.5 μs after pulsed laser excitation (400 nm, 5 ns pulse width);

FIG. 18 illustrates the redox potential of protoporphyrin IX (FIG. 18A), Formula I(a)(1) (FIG. 18B), Formula I(a)(1) (FIG. 18C), Formula IIbi (FIG. 18D), Formula IIfi (FIG. 18E), and Formula IIci (FIG. 18F), according to a specific example embodiment of the disclosure;

FIG. 22 illustrates a reduction in visible light-induced reactive oxygen species (ROS) in human cells mediated by a conjugated fused tricycle compound according to a specific example embodiment of the disclosure, as shown by fluorescence imaging of untreated cells (FIG. 22A), cells irradiated in the absence of a polycyclic molecule (FIG. 22B), and cells irradiated in the presence of a polycyclic molecule (FIG. 22C), and quantitative fluorescence assessment (FIG. 22D);

DETAILED DESCRIPTION

Figures 1A, 1B:
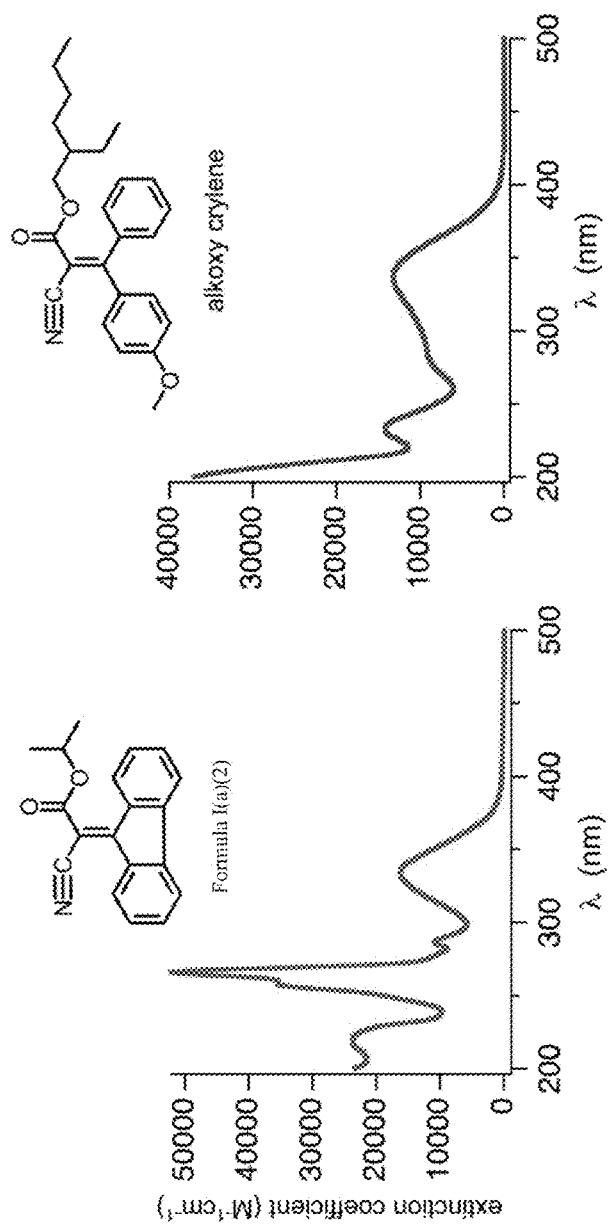
FIG. 1A illustrates an absorption spectra of an acceptor compound according to a specific example embodiment of the disclosure, Formula I(a)(1) in acetonitrile.
FIG. 1B illustrates an absorption spectra of an acceptor compound according to a specific example embodiment of the disclosure, alkoxy crylene in acetonitrile.

The present disclosure relates, in some embodiments, to molecules, including conjugated fused polycyclic molecules, that may receive excited state energy from other molecules (e.g., light-absorbing molecules) or directly from the irradiation sources. According to some embodiments, the present disclosure relates to molecules, including fused polycyclic molecules (e.g., conjugated fused polycyclic molecules), that may quench, dissipate, and/or otherwise resolve excited state energy, normally by way of releasing it as heat. (e.g., as heat).

A light-absorbing molecule (e.g., chromophore) may absorb visible light (e.g., at about 400 to about 800 nm) and/or UV light (e.g., at about 290 to about 400 nm), which causes the excitation of an electron in the molecule from an initially occupied, lower energy orbital to a higher energy, previously unoccupied orbital. The energy of the absorbed photon is used to energize an electron and cause it to enter a higher energy orbital. Two excited electronic states derive from the electronic orbital configuration produced by visible and/or UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

When light-absorbing molecules are in an electronically excited state as a result of photon absorption, they can transfer excited state energy to other species to generate reactive products. For example, excited light-absorbing molecules can transfer excited state energy to oxygen, which may result in the generation of reactive oxygen species (e.g., singlet oxygen, free radical oxygen, superoxide anion, peroxide, hydroxyl radical, and hydroxyl ion). Formation of these species often results in unwanted effects including, for example, physical and chemical damage to nearby molecules. This damage can lead to loss of desired coloration of colored compositions, reduction of structural integrity (e.g., polymeric compounds), and/or irreversible changes to bioactive molecules in living cells.

Colorants may be substances that impact color by reflecting and/or transmitting light as a result of wavelength-selected absorption. Colorants may combined with other molecules and/or included in compositions (e.g., paints, coatings, inks, plastics, fabrics, cosmetics, food) to modify the appearance of the mixture. Organic dyes may be colorants that are either liquids themselves, or they are dissolved in a liquid to produce a solution. Organic pigments may be colorants that may be insoluble in one or more particular vehicles, and result in suspensions. Colorants may include organic dyes and organic pigments. A colorant may be or may comprise a chromophore capable of entering one or more excited states when exposed to UV and visible light, such as sunlight. An excited state may lead to undesirable photobleaching of colorants.

Polymeric materials may be included in, for example, coatings, moldings, paints, inks, and the like. Reactive oxygen species ("ROS") may photooxidize polymers. For example, hydroperoxide groups, aldehydes, and ketones may form on the polymer backbone upon exposure to ROS. Photooxidation may result in, for example, chain scission (e.g., reduced molecular weight), crosslinking (e.g., increased molecular weight), secondary oxidative reactions, and/or combinations thereof. A photooxidized polymer material may be altered, appearing weathered, discolored, and/or coarse relative to an unoxidized material. Consequences (e.g., unwanted consequences) of such polymer degradation may include altered strength (e.g., tensile strength, impact strength), elasticity, resilience, rigidity, ductility, and/or combinations thereof. It may be desirable, therefore, to return electronically excited chromophores to the ground state before they can transfer excited state energy to a oxygen molecules, according to some embodiments.

The present disclosure relates, in some embodiments, to molecules that may receive excited state energy from other molecules (e.g., light-absorbing molecules). According to some embodiments, the present disclosure also relates to molecules that may quench, dissipate, and/or otherwise resolve excited state energy. A molecule that donates excited state energy may be referred to as a donor molecule and/or a molecule that receives excited state energy may be referred to as a receiver or acceptor molecule in some embodiments. An acceptor molecule may comprise, for example, a conjugated fused polycyclic molecule. In some embodiments, a donor molecule may be a photoactive—it may absorb incident radiation (e.g., UV radiation). For example, a molecule exposed to light may absorb one or more photons. Absorbed energy (e.g., photons) may raise a low energy state electron (e.g., ground state electron) to an excited energy state (e.g., singlet or triplet). Formation and/or resolution of the excited energy state may lead to unwanted effects including, for example, formation of radicals and/or chemical breakdown of polymers, dyes, and/or pigments.

Various strategies may be adopted for mitigating the adverse effects of potentially exciting energy sources (e.g., light). For example, the object may be isolated from potentially exciting energy sources. Isolation may include a complete photo, electro, and/or thermal disconnect between the potential source(s) and the object to be protected. Another strategy may include filtering the potential source(s) such that the object and potential source are in limited photo, electro, and/or thermal communication. For example, light may be filtered (e.g., using a sunscreen) such that less or no radiation can reach the object to produce adverse effects in the object. In yet another approach, adverse effects from potentially exciting energy sources may also be mitigated by limiting or preventing free radical damage. For example, anti-oxidants may be added to react with the free radicals formed before the radicals have an opportunity to interact with and damage the object to be protected.

These strategies may not always produce desired results. Accordingly, it may be desirable to move upstream in the excitation process. For example, preventing radical formation may have advantages over applying antioxidants afterwards. Isolation and/or filtering techniques may be employed to prevent formation of the excited energy state. However, these approaches may not be satisfactory either, for example, where exposure of the object to the potentially exciting energy source is desirable, necessary and/or inevitable.

According to some embodiments, the present disclosure relates to molecules, compositions, systems, and methods for promptly resolving excited energy states after formation. Excited state resolution may occur through a pathway or pathways that mitigate or prevent unwanted and/or harmful effects (e.g., radical formation, sensitization of surrounding molecules, producing unwanted photoproducts).

According to some embodiments, compositions, systems, and methods of the present disclosure may be operable without regard to the source of the excitation energy. For example, excited energy states may be resolved where the excited state arose from another excited species by way of sensitization and/or direct electromagnetic radiation of any wavelength sufficient to eject an electron from its ground state to an excited state. Examples of electromagnetic radiation include visible light, ultra violet radiation, and X-rays. Thus, molecules and compositions according to some embodiments of the disclosure may provide a broad spectrum of protection. For example, protection may be provided in a UV range through filtering and/or quenching and/or in a visible range by quenching.

In some embodiments, the present disclosure relates to conjugated fused polycyclic molecules. For example, a conjugated fused polycyclic molecule may comprise a conjugated fused tricyclic molecule. A conjugated fused polycyclic molecule may include and/or may exclude any desired atom or functional group, according to some embodiments. For example, a conjugated fused polycyclic molecule may exclude halogens, silicon and/or selenium. Each ring of a conjugated fused polycyclic molecule may have, in some embodiments, about 3 to about 8 members. For example, a polycyclic molecule may include a fused tricyclic moiety in which the rings are designated X, Y, and Z. Rings X and Y may have 6 members each, interposed by ring Z having 5 or 6 members. Rings X, Y, and Z may be co-planar, for example, to increase or maximize electron delocalization and/or regulating reduction potential.

A conjugated fused polycyclic compound may have, according to some embodiments, a structure according to Formula I or a salt thereof:

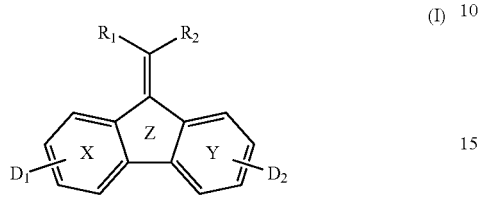
(I)

wherein

R₁ may be independently nitrile, C(O)R₃, C(O)N(R₄)R₅, C(O)—S—R₆, or fused aryl,

R₂ may be independently nitrile, C(O)R₇, C(O)N(R₈)R₉, C(O)—S—R₁₀, or fused aryl, R₃, R₄, R₅, R₆, R₇, R₈, R₉, and R₁₀ may be independently H, aryl, substituted aryl, fused aryl, alkyl, substituted alkyl, or branched alkyl, D₁ may be independently H, hydroxyl, or R₁₁, D₂ may be independently H, hydroxyl, or R₁₂, R₁₁ and R₁₂ may be independently H, alkyl, heteroalkyl, alkoxyl, heteroalkoxyl, aryl, heteroaryl, or fused aryl, provided that R₁ and R₂ are not both nitrile, R₁ and R₂ are not fused to each other, R₁₁ and R₁₂ do not comprise azo, the fused tricyclic moiety defined by rings X, Y, and Z is the only tricyclic moiety in the molecule, and D₁ and D₂ are not fused to each other.

In some embodiments, R₁ may further comprise C(O)OR₃ or aryl and/or R₂ may further comprise C(O)OR₇ or aryl. R₁ and/or R₂ may comprise one or more electron-withdrawing groups. Substitutions (e.g., on rings X and Y) may be chosen for ready non-radioactive decay (e.g., para substitution), in some embodiments.

According to some embodiments, a conjugated fused polycyclic molecule may have a molecular weight of less than about 2,000, less than about 1,800, less than about 1,600, less than about 1,400, less than about 1,200, less than about 1,000, less than about 900, less than about 800, less than about 750, less than about 700, less than about 650, less than about 600, less than about 550, and/or less than about 500. For example, a conjugated fused polycyclic molecule may have a molecular weight of about 240 to about 750. Ring X and D₁ together may have a molecular weight of up to about 500 (e.g., up to about 400, up to about 300, up to about 250, about 75 to about 200, about 75 to about 300, and combinations thereof). Ring Y and D₂ together may have a molecular weight of up to about 500 (e.g., up to about 400, up to about 300, up to about 250, about 75 to about 200, about 75 to about 300, and combinations thereof), according to some embodiments. R₁ and/or R₂ each independently may have a molecular weight of up to about 500 (e.g., up to about 400, up to about 300, up to about 250, about 40 to about 200, about 40 to about 300, and combinations thereof).

Examples of Formula I may include Formulas I(a)-I(i):

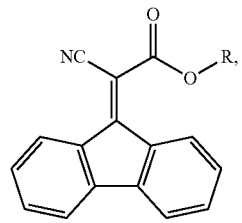
I(a)

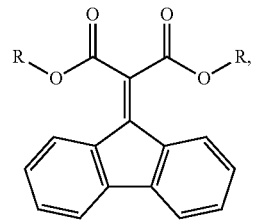
I(b)

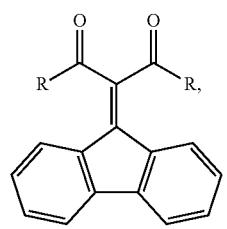
I(c)

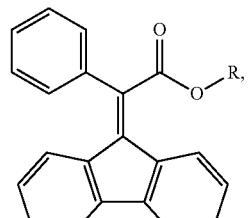
I(d)

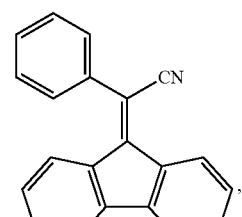
I(e)

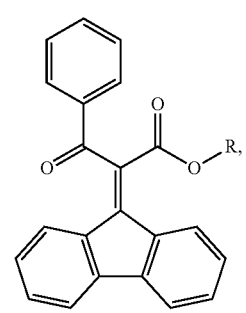
I(f)

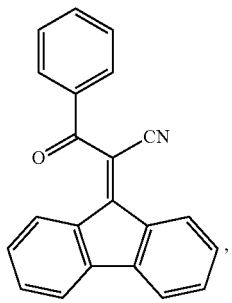

I(g)

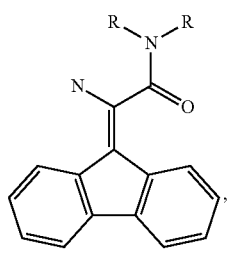

I(h)

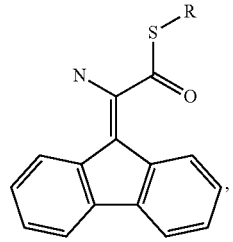

I(i)

wherein each R may be independently selected from $R_1$, $R_2$, $R_3$, $R_4$, $R_5$, $R_6$, $R_7$, $R_8$, $R_9$, $R_{10}$, $R_{11}$, $R_{12}$, and/or combinations thereof. In some embodiments, substituents (e.g., $R_1$, $R_2$, $R_3$, $R_4$, $R_5$, $R_6$, $R_7$, $R_8$, $R_9$, $R_{10}$, $R_{11}$, $R_{12}$, $D_1$, $D_2$) may be the same or different. According to some embodiments, substituents may be independently selected. In some embodiments, each R may be $C_1$-$C_{30}$ alkyl, $C_1$-$C_{20}$ alkyl, or $C_1$-$C_{10}$ alkyl. For example, R may include, but is not limited to, methyl, ethyl, propyl, isopropyl, or 2-ethylhexyl.

According to some embodiments, an aryl group may comprise a carbocyclic aromatic ring system having a single ring, two fused rings, or three fused rings. An aryl group may be selected from phenyl, naphthyl, tetrahydronaphthyl, phenanthrenyl, biphenylenyl, indanyl, indenyl, anthracenyl, and fluorenyl.

An alkyl group may comprise, in some embodiments, a straight- and/or branched-chain saturated hydrocarbon having from about 1 to about 30 (C1-C30) or more carbon atoms. Examples of alkyl groups may include methyl, ethyl, n-propyl, isopropyl, n-butyl, sec-butyl(2-methylpropyl), t-butyl(1,1-dimethylethyl), and 3,3-dimethylpentane. An alkoxyl group may comprise —O-alkyl, in some embodiments.

A substituted alkyl group may comprise, in some embodiments, an alkyl having one or more substituents. Substituents may include, for example, heteroalkyl, ester, carboxy, cyano, amino, amido, sulfur, and/or halo. In some embodiments, a substituted alkyl group may be mono-, di-, or tri-substituted at each of one, two, or three carbon atoms. Substituents may be present on a single carbon or distributed among more than one carbon.

A nitrile group (also called a cyano group) may comprise a —C≡N (also "—CN"), in some embodiments.

Formula I, in some embodiments, excludes 9-(dicyanomethylene)fluorine (e.g., because $R_1$ and $R_2$ cannot both be nitrile if $D_1$ and $D_2$ are hydrogen).

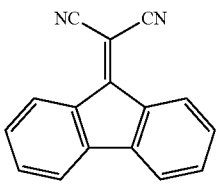

I(j)

According to some embodiments, $R_1$ and $R_2$ may be the same or different. For example, $R_1$ and $R_2$ may be selected to be different from each other. $R_1$ and $R_2$ may be selected, according to some embodiments, such that the two are distinct from each other (e.g., not fused to each other forming a 5 or 6 member ring). In some embodiments, $R_1$ cannot be nitrile if $R_7$ is a branched alkyl. $R_3$ cannot be a branched alkyl if $R_2$ is nitrile, according to some embodiments. $R_3$ and $R_7$ cannot be methyl or ethyl, according to some embodiments. For example, $R_3$ and $R_7$ may be selected to exclude methyl and ethyl where $D_1$ and/or $D_2$ comprise an ethylene group and/or a ketone. In some embodiments, $R_1$ may exclude $C(O)OR_3$ and/or exclude aryl. $R_2$ may likewise exclude $C(O)OR_7$ and/or exclude aryl.

$D_1$ and/or $D_2$, according to some embodiments, may be selected to exclude an azo group (e.g., —N=N—), an imine group (e.g., —N=C—), a nitro group (e.g., —$NO_2$), an ethylene group (e.g., non-aryl —C=C—), an ester group (e.g., —C(O)—O—), a sulfone group, a ketone group, a nitrile group, a carboxyl group (e.g., —COOH), a ketone, a thio ether group (e.g., —S—), and/or combinations thereof. According to some embodiments, $D_1$ and/or $D_2$ may be selected to exclude a group that comprises an azo group, an imine group, a nitro group, an ethylene group, an ester group, a sulfone group, a ketone group, a nitrile group, a carboxyl group, a ketone, a thio ether group, and/or combinations thereof. $D_1$ and/or $D_2$, according to some embodiments, may be selected to be the same or different. $D_1$ may include a ring that is fused to ring X according to some embodiments. $D_2$ may include, in some embodiments, a ring that is fused to ring Y. In some embodiments, $D_1$ and $D_2$ cannot both be —H. $D_1$ and $D_2$, according to some embodiments, are distinct from each other (e.g., not fused to each other forming a ring). For example, $D_1$ and $D_2$ may be distinct if $R_1$ and $R_2$ are both nitrile. $D_1$ and $R_1$ may be distinct from each other (e.g., not fused to each other forming a ring). $D_2$ and $R_2$ may be distinct from each other (e.g., not fused to each other forming a ring). In some embodiments, $D_1$ may exclude alkenyl, $D_2$ may exclude alkenyl, or $D_1$ and $D_2$ may both exclude alkenyl.

$D_1$ and/or $D_2$ may be joined, according to some embodiments, to rings X and/or Z, respectively, by any desired bond. In some embodiments, $D_1$ and/or $D_2$ may be joined to rings X and/or Z, respectively, by any bond other than a carbonyl (e.g., D-C(O)—X) and/or any bond other than an ester (e.g., D-C(O)—O—X, X—C(O)—O-D). According to some embodiments, Ring X may comprise no substituents other than $D_1$ and/or ring Z may comprise no substituents other than $D_2$.

According to some embodiments, if $R_1$ and $R_2$ are both nitrile, $D_1$ and/or $D_2$ may be selected to exclude an azo group, an imine group, a nitro group, an ethylene group, an ester group (e.g., a butyl ester group), a sulfone group, a nitrile group, a carboxyl group, a thio ether group, and/or combinations thereof. If $R_1$ is nitrile and $R_2$ is a substituted aryl (or vice versa), $D_1$ and/or $D_2$ may be selected to exclude a nitro group, in some embodiments.

A conjugated fused polycyclic compound may have, according to some embodiments, a structure according to Formula II or a salt thereof:

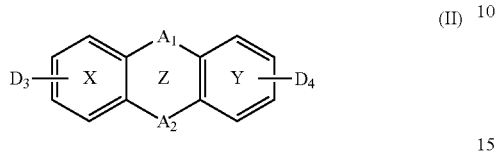

wherein $A_1$ may be independently carbonyl, $C=C(R_{13})R_{14}$, O, S, $S=O$, $S(O)=O$, $C=S$, $R_{13}$ may be independently nitrile, $C(O)OR_{15}$, $C(O)R_{16}$, $C(O)N(R_{17})R_{18}$, $C(O)-S-R_{19}$, aryl, substituted or fused aryl, $R_{14}$ may be independently nitrile, $C(O)OR_{20}$, $C(O)R_{21}$, $C(O)N(R_{22})R_{23}$, $C(O)-S-R_{24}$, aryl, substituted or fused aryl, $R_{15}$, $R_{16}$, $R_{17}$, $R_{18}$, $R_{19}$, $R_{20}$, $R_{21}$, $R_{22}$, $R_{23}$, and $R_{24}$, may be independently aryl, substituted aryl, fused aryl, alkyl, substituted alkyl, or branched alkyl, $A_2$ may be independently carbonyl, $C=C(R_{13})R_{14}$, O, S, $S=O$, $S(O)=O$, $C=S$, $D_3$ may be independently H, hydroxyl, or $R_{25}$, $D_4$ may be independently H, hydroxyl, or $R_{26}$, $R_{25}$ may be independently alkyl, heteroalkyl, alkoxyl, heteroalkoxyl, aryl, heteroaryl, or fused aryl, $R_{26}$ may be independently alkyl, heteroalkyl, alkoxyl, heteroalkoxyl, aryl, heteroaryl, or fused aryl, provided that at least one of $A_1$ and $A_2$ is $C=C(R_{13})R_{14}$, if neither $A_1$ nor $A_2$ is S, for each $C=C(R_{13})R_{14}$, no more than one of $R_{13}$ and $R_{14}$ is nitrile (e.g., if both $A_1$ and $A_2$ are $C=C(R_{13})R_{14}$, no more than one of $R_{13}$ and $R_{14}$ of the $A_1$ group may be nitrile and no more than one of $R_{13}$ and $R_{14}$ of the $A_2$ group may be nitrile), and if either $A_1$ nor $A_2$ is O, for each $C=C(R_{13})R_{14}$, no more than one of $R_{13}$ and $R_{14}$ is $C(O)OR_{15/20}$ (i.e., if $R_{13}$ is $C(O)OR_{15}$, $R_{14}$ cannot be $C(O)OR_{20}$ and vice versa).

According to some embodiments, $R_1$ and/or $R_2$ may comprise one or more electron-withdrawing groups. Substitutions (e.g., on rings X and Y) may be chosen for ready non-radioactive decay (e.g., para substitution), in some embodiments.

According to some embodiments, a conjugated fused polycyclic molecule may have a molecular weight of less than about 2,000, less than about 1,800, less than about 1,600, less than about 1,400, less than about 1,200, less than about 1,000, less than about 900, less than about 800, less than about 750, less than about 700, less than about 650, less than about 600, less than about 550, and/or less than about 500. For example, a conjugated fused polycyclic molecule may have a molecular weight of about 240 to about 750. Ring X and $D_3$ together may have a molecular weight of up to about 500 (e.g., up to about 400, up to about 300, up to about 250, about 75 to about 200, about 75 to about 300, and combinations thereof). Ring Y and $D_4$ together may have a molecular weight of up to about 500 (e.g., up to about 400, up to about 300, up to about 250, about 75 to about 200, about 75 to about 300, and combinations thereof), according to some embodiments. $A_1$, $A_2$, $R_{10}$ and/or $R_{11}$ each independently may have a molecular weight of up to about 500 (e.g., up to about 400, up to about 300, up to about 250, about 40 to about 200, about 40 to about 300, and combinations thereof).

Examples of Formula II may include Formulas II(a)-II(bj):

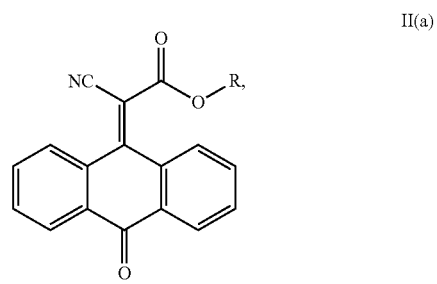

II(a)

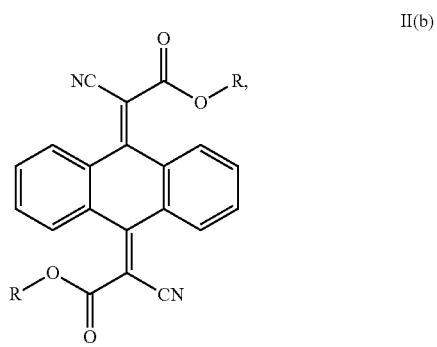

II(b)

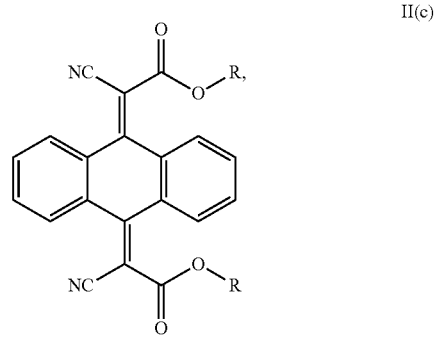

II(c)

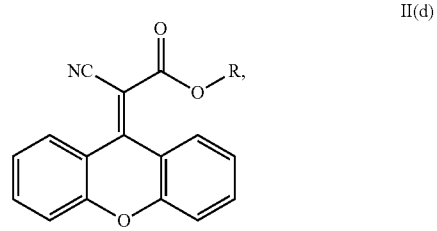

II(d)

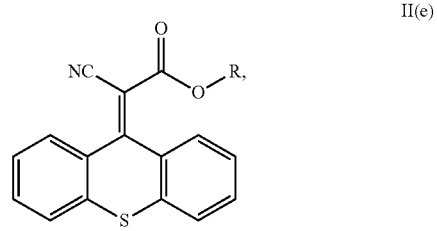

II(e)

-continued
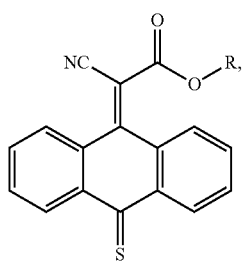
II(f)
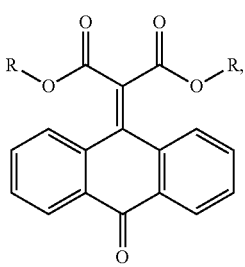
II(g)
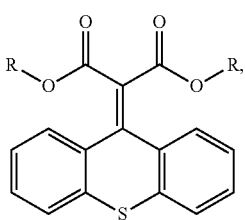
II(h)
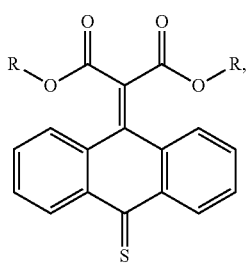
II(i)
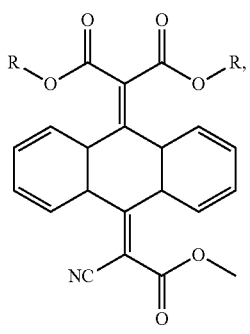
II(j)
-continued
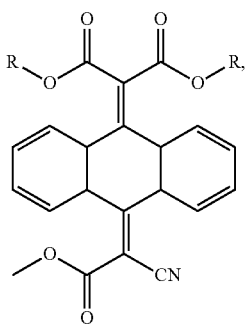
II(k)
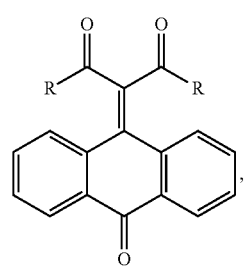
II(l)
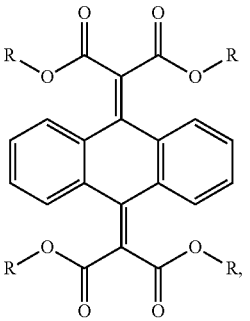
II(m)
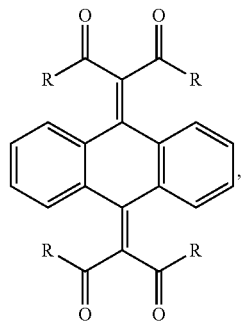
II(n)
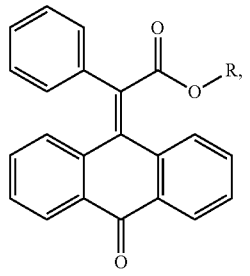
II(o)

II(p)
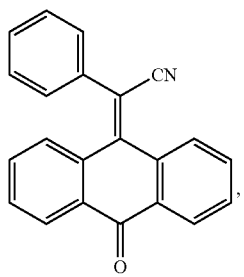
II(q)
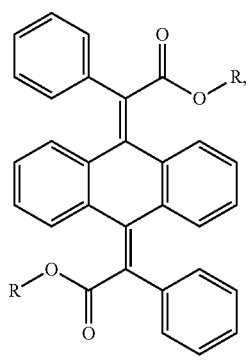
II(r)
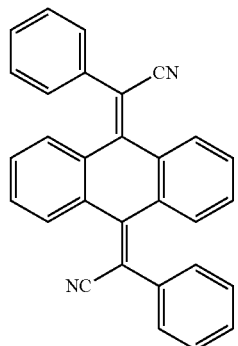
II(s)
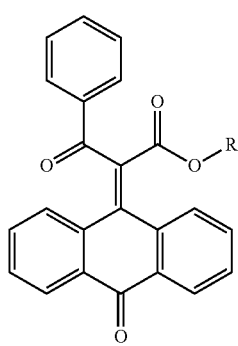
II(t)
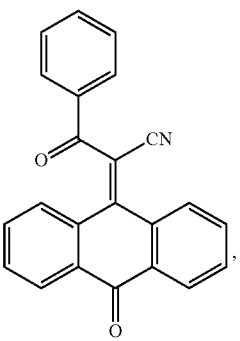
II(u)
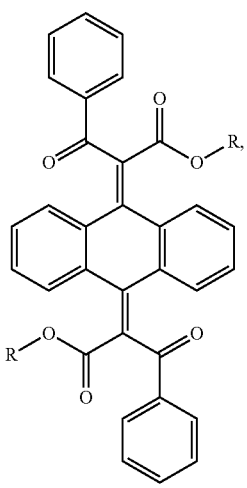
II(v)
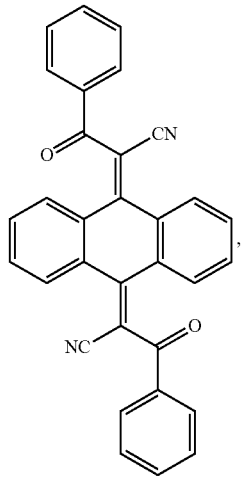
II(w)
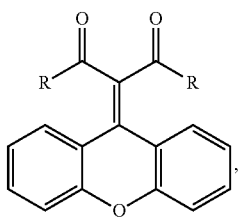

II(x)
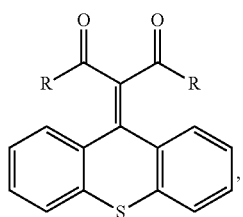
II(y)
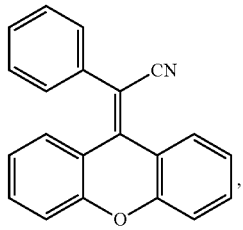
II(z)
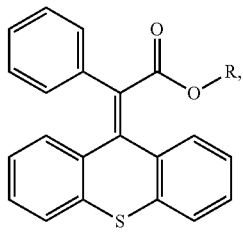
II(aa)
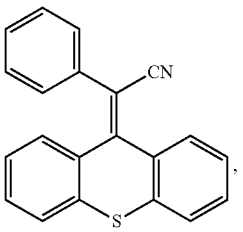
II(ab)
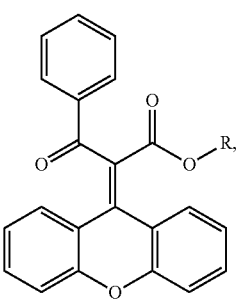
II(ac)
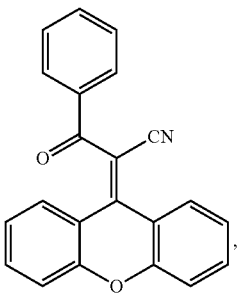
II(ad)
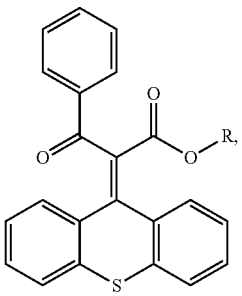
II(ae)
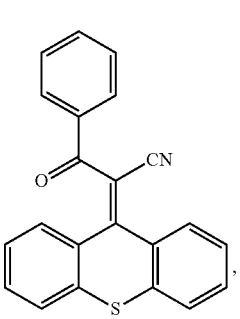
II(af)
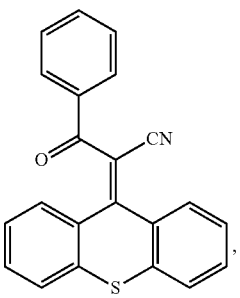
II(ag)
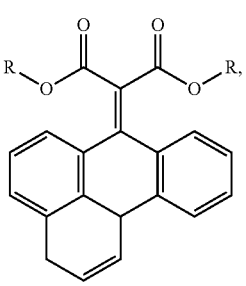
II(ah)
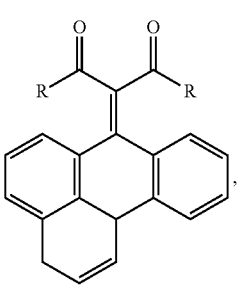

-continued
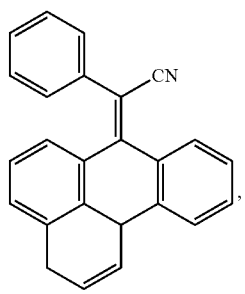
II(ai)
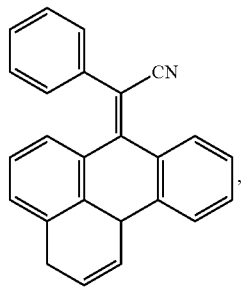
II(aj)
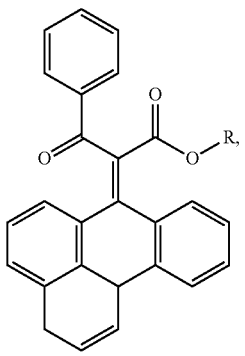
II(ak)
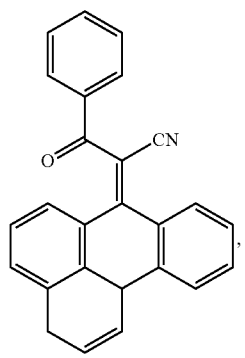
II(al)
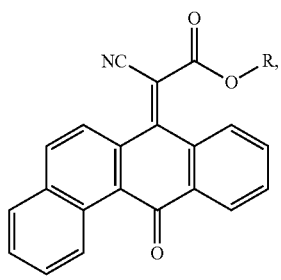
II(am)
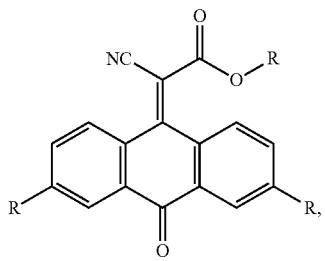
II(an)
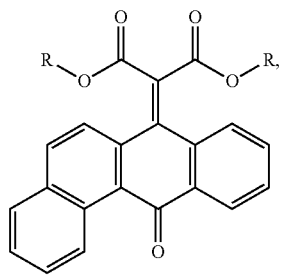
II(ao)
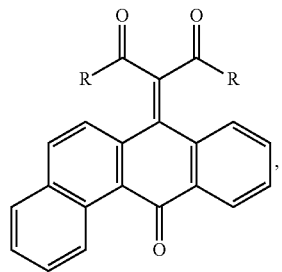
II(ap)
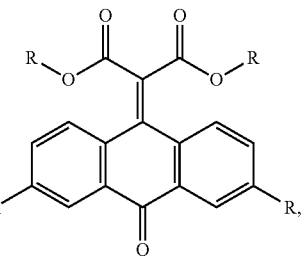
II(aq)
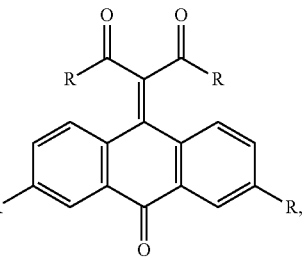
II(ar)
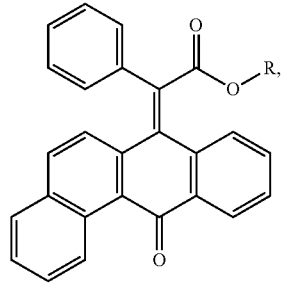
II(as)

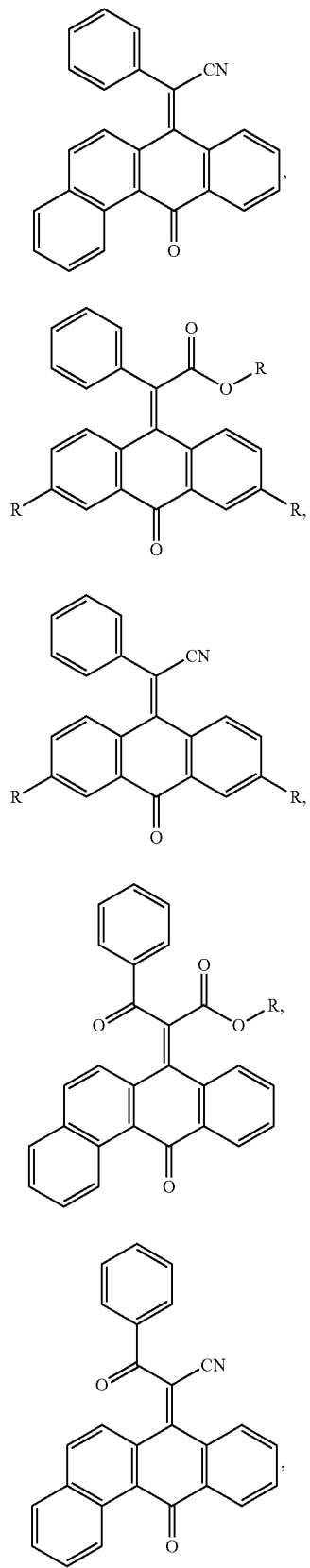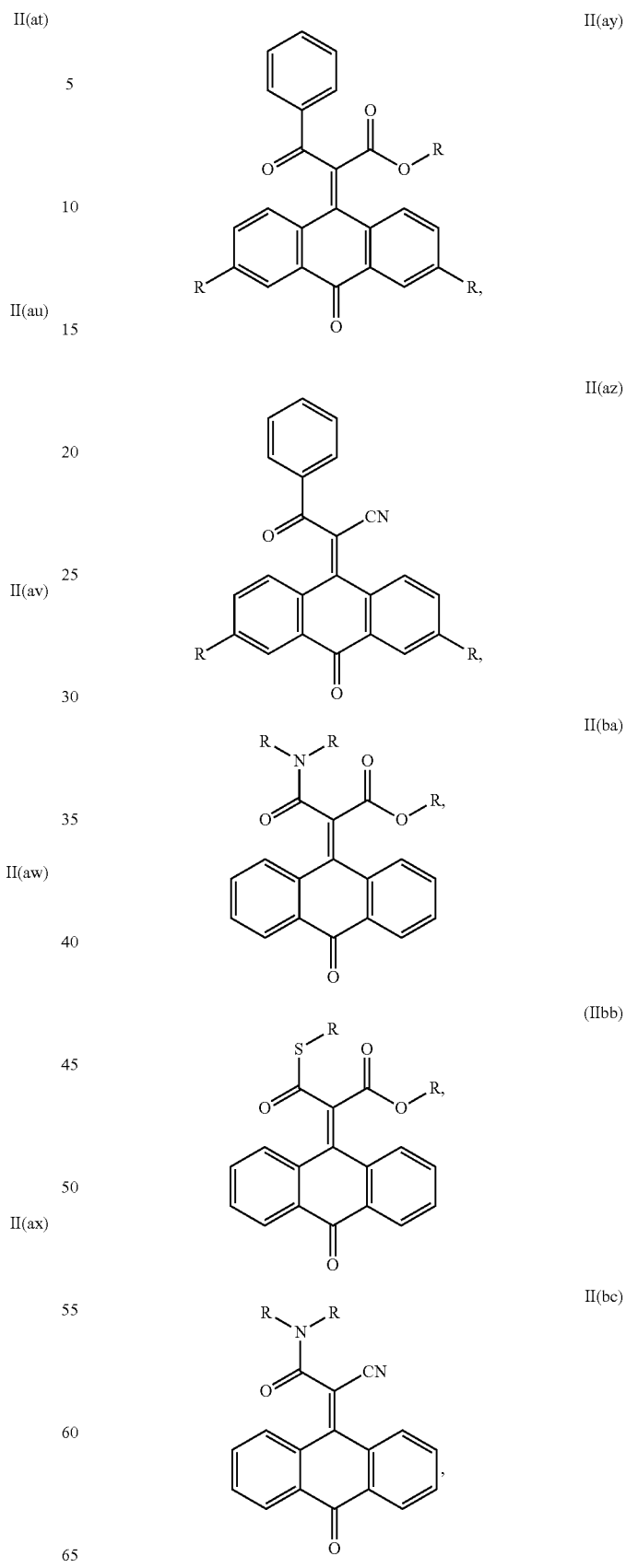

II(bd)
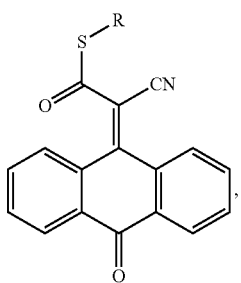

II(be)
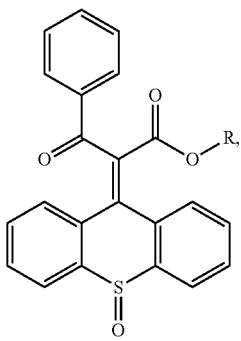

II(bf)
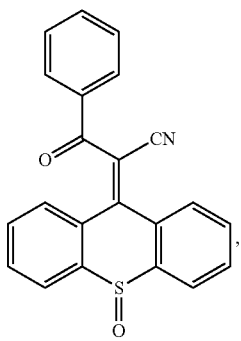

II(bg)
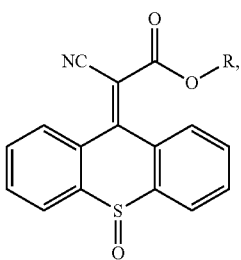

II(bh)
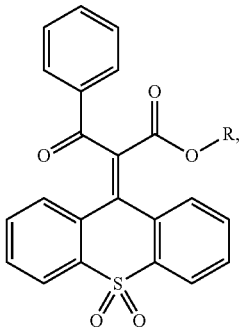

II(bi)
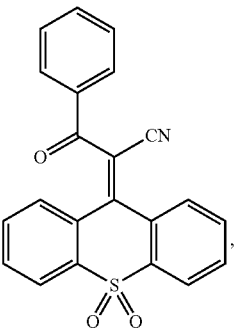

II(bj)
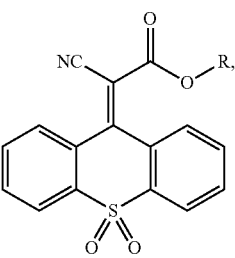

II(bk)
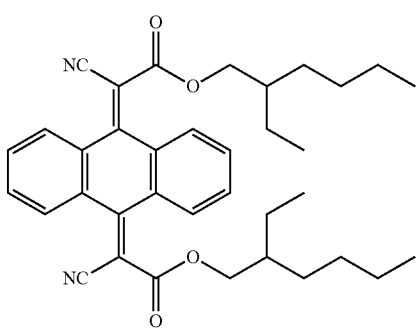

wherein each R may be independently selected from $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and/or combinations thereof. In some embodiments, substituents (e.g., $A_1$, $A_2$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $D_3$, $D_4$) may be the same or different. According to some embodiments, substituents may be independently selected. In some embodiments, each R may be $C_1$-$C_{30}$ alkyl, $C_1$-$C_{20}$ alkyl, or $C_1$-$C_{10}$ alkyl. For example, R may include, but is not limited to, methyl, ethyl, propyl, isopropyl, or 2-ethylhexyl.

Formula II, in some embodiments, excludes:

II(bl)
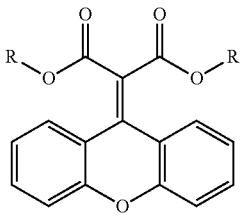

(e.g., because $R_{13}$ cannot be $C(O)OR_{15}$ where $R_{14}$ is $C(O)OR_{20}$).

According to some embodiments, $D_3$ and $D_4$ may not comprise an azo group. For example, $D_3$ and $D_4$ may exclude azo where $R_{13}$ and $R_{14}$ are nitrile and $A_1$ is a carbonyl group. $D_3$ and $D_4$ may exclude azo where $R_{13}$ and $R_{14}$ are nitrile and $A_2$ is a carbonyl group. $D_3$ and $D_4$ may not comprise, in some embodiments, an amine (e.g., a primary amine). For example, $D_3$ and $D_4$ may exclude a primary amine where $R_{13}$ and $R_{14}$ are nitrile and $A_1$ is a carbonyl group. $D_3$ and $D_4$ may exclude a primary amine where $R_{13}$ and $R_{14}$ are nitrile and $A_2$ is a carbonyl group. $D_3$ and $D_4$ may not comprise an imine group, according to some embodiments. For example, $D_3$ and $D_4$ may exclude an imine group where $R_{13}$ and $R_{14}$ are nitrile.

In some embodiments, $D_3$ and $D_4$ may not comprise a nitro group. For example, $D_3$ and $D_4$ may not comprise a nitro group where $R_{13}$ and $R_{14}$ are nitrile and $A_1$ is —O—. $D_3$ and $D_4$ may not comprise a nitro group where $R_{13}$ and $R_{14}$ are nitrile and $A_2$ is —O—. $D_3$ and $D_4$ may not comprise, according to some embodiments, a methylether group (e.g., a —OCH$_3$). For example, $D_3$ and $D_4$ may not comprise a methylether group where $R_{13}$ and $R_{14}$ are nitrile and $A_1$ is —O—. $D_3$ and $D_4$ may not comprise a methylether group where $R_{13}$ and $R_{14}$ are nitrile and $A_2$ is —O—.

$D_3$ and $D_4$ may not comprise an ethylene group (e.g., a non-aromatic, non-cyclic, carbon-carbon double bond), according to some embodiments. For example, $D_3$ and $D_4$ may exclude an ethylene group where the ethylene joins a fused polycyclic molecule to a backbone, other identical or similar polycyclic moieties, or to a polymer or other macromolecule. $D_3$ and $D_4$ may exclude an ethylene group where $R_{13}$ and $R_{14}$ are nitrile.

In some embodiments, $R_{15}$ and $R_{20}$ may not comprise a methyl group. For example, $R_{15}$ and $R_{20}$ may not comprise a methyl group where $A_1$ is —O—. $R_{15}$ and $R_{20}$ may not comprise a methyl group where $A_2$ is —O—. $R_{15}$ and $R_{20}$ may not comprise, in some embodiments, an ethyl group. For example, $R_{15}$ and $R_{20}$ may not comprise an ethyl group where $A_1$ is —O—. $R_{15}$ and $R_{20}$ may not comprise an ethyl group where $A_2$ is —O—.

$D_3$ and/or $D_4$ may be joined, according to some embodiments, to rings X and/or Z, respectively, by any desired bond. In some embodiments, $D_3$ and/or $D_4$ may be joined to rings X and/or Z, respectively, by any bond other than a carbonyl (e.g., D-C(O)—X) and/or any bond other than an ester (e.g., D-C(O)—O—X, X—C(O)—O-D). According to some embodiments, Ring X may comprise no substituents other than $D_3$ and/or ring Z may comprise no substituents other than $D_4$.

In some embodiments, a molecule of Formula I or Formula II may comprise at least three fused conjugated rings and may have a total of up to 3 rings, up to 4 rings, up to 5 rings, or up to 6 rings. A molecule of Formula I or Formula II may have, according to some embodiments, up to 4 rings fused to each other. In some embodiments, a molecule of Formula I or Formula II may include a single atom that is shared by up to 3 rings. A molecule of Formula I or Formula II may include no more than one atom that is shared by 3 rings and/or no atoms that are shared by more than 3 rings, according to some embodiments. Two rings fused to each other may share 2 atoms (e.g., carbon atoms) and 1 bond (e.g., single bond, double bond, conjugated pi bond) according to some embodiments.

A conjugated fused polycyclic molecule according to Formula I may have and/or may require $R_1$, $R_2$, $R_3$, $R_4$, $R_5$, $R_6$, $R_7$, $R_8$, $R_9$, $R_{10}$, $R_{11}$, $R_{12}$, $D_1$, and/or $D_2$ to have a structure other than a polymeric structure, in some embodiments. A conjugated fused polycyclic molecule according to Formula II may have and/or may require $A_1$, $A_2$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $D_3$, and/or $D_4$ to have a structure other than a polymeric structure, in some embodiments. For example, a conjugated fused polycyclic molecule may comprise only one tricyclic group (e.g., rings X, Y, and Z) per molecule. A conjugated fused polycyclic molecule may have a monomeric and/or non-repeating structure, in some embodiments. A free conjugated fused polycyclic molecule, according to some embodiments, may be soluble in a selected solvent and/or may not be covalently linked to a polymer.

According to some embodiments, a polymeric structure may comprise a step-growth polymer such as a polyester, a polyamides, or a polyurethane. The polymer structure can also be a chain-growth polymer such as a polyacrylate, a polystyrene, a polyolefine and their co-polymer.

In some embodiments, a conjugated fused polycyclic molecule may resolve an excited state according to a mechanism comprising:

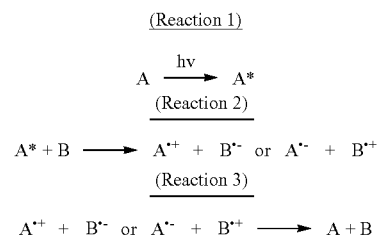

wherein A is a light-absorbing donor molecule and B is a conjugated fused polycyclic acceptor molecule.

A conjugated fused polycyclic compound may have, according to some embodiments, a structure according to Formula III or a salt thereof:

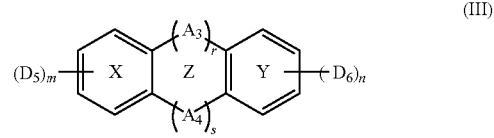

wherein
 m and n each independently may be 0, 1, 2, 3, or 4,
 r and s each may be 0 or 1,
 $A_3$ and $A_4$ each independently may be carbonyl, C=C($R_{27}$)$R_{28}$, O, S, S=O, S(O)=O, or C=S,
 $R_{27}$ may be nitrile, C(O)O$R_{29}$, C(O)$R_{30}$, C(O)N($R_{31}$)$R_{32}$, C(O)—S—$R_{33}$, C(O)—O—S—$R_{34}$, C=CH$R_{35}$, N($R_{36}$)$_3^+$, F, Cl, Br, I, CF$_3$, CCl$_3$, NO$_2$, aryl, substituted aryl, or fused aryl,
 $R_{28}$ may be nitrile, C(O)O$R_{37}$, C(O)$R_{38}$, C(O)N($R_{39}$)$R_{40}$, C(O)—S—$R_{41}$, C(O)—O—S—$R_{42}$, C=CH$R_{43}$, N($R_{44}$)$_3^+$, F, Cl, Br, I, CF$_3$, CCl$_3$, NO$_2$, aryl, substituted aryl, or fused aryl,
 $R_{29}$ and $R_{37}$ each independently may be H, alkyl, cycloalkyl, alkenyl, cycloalkenyl, alkynyl, aryl, substituted aryl, or fused aryl,
 $R_{30}$, $R_{31}$, $R_{32}$, $R_{33}$, $R_{34}$, $R_{35}$, $R_{38}$, $R_{39}$, $R_{40}$, $R_{41}$, $R_{42}$, and $R_{43}$ each independently may be H, alkyl, cycloalkyl, alkenyl, cycloalkenyl, alkynyl, or aryl, substituted aryl, or fused aryl, alkyl, substituted alkyl, or branched alkyl,
 $R_{36}$ and $R_{44}$ each independently may be H or $C_1$-$C_6$ alkyl, and $D_5$ and $D_6$ may be independently $R_{27}$, $R_{28}$, heteroaryl, hydroxyl, alkyl, or alkoxyl, provided that r+s≥1, and at least one of $A_3$ and $A_4$ is $C=C(R_{27})R_{28}$.

According to some embodiments, $R_1$ and/or $R_2$ may comprise one or more electron-withdrawing groups. Substitutions (e.g., on rings X and Y) may be chosen for ready non-radioactive decay (e.g., para substitution), in some embodiments.

The present disclosure relates, in some embodiments, to a compositions for resolving an electronically excited state of a donor molecule. Compositions may include at least one donor molecule and at least one acceptor molecule, according to some embodiments. Compositions may be formulated for any desired application. For example, compositions may be formulated for industrial, cosmetic, culinary, pharmaceutical, medical, and/or recreational uses. Compositions may include, in some embodiments, paints (e.g., paints for cars, boats, aircraft, buildings, signs, roadways, and any other building or structure exposed to light), coatings (e.g., clear coatings), textiles (e.g., woven or non-woven fabrics), polymers (e.g., plastics, rubbers), bituminous materials, inks, toners, photographic emulsions, glass, make-up materials, suncare materials, and combinations thereof.

In some embodiments, a composition comprising a donor and/or acceptor molecule may be formulated for use in or with roofing materials. For example, an acceptor and/or a donor may be included in an underlayment, a bituminous material, a resin (e.g., bonded to a reinforcing mat), a covering layer, and/or an adhesive.

Donor molecules may include, for example, photounstable visible light abosorbers and UV light absorbers. Donors may be sensitizers (e.g., photosensitizers), in some embodiments. Examples of donor molecules may include, according to some embodiments, pigments, porphyrins, riboflavins, melanins, azo, xanthene, phenothiazinium, triphenyl methane, and/or dibenzoylmethane derivatives. For example, it has been found that conjugated fused polycyclic molecules may resolve (e.g., quench) the singlet and/or triplet excited energy state of photounstable visible light and photounstable UV light absorbers. Transfer of excited state energy from a donor molecule to an acceptor molecule may result in returning the donor molecule to its ground state and/or reduction in the generation of singlet oxygen or other unwanted effects. Where a composition is a topical for application to skin, the contacted skin may be relieved of at least some of the oxidative stress to which it would have otherwise been exposed.

Accordingly, by applying one or more of the conjugated fused tricyclic compounds, in a dermatologically or cosmetically acceptable carrier, onto mammalian skin, e.g., human skin, the skin may not suffer from oxidative stress due to the generation of potentially cytotoxic singlet oxygen. Thus, the compositions and methods described herein advantageously quench the excited state reached by dibenzoylmethane derivatives, porphyrins, and/or related chromophores endogenous to human skin, thereby significantly reducing the generation of singlet oxygen in cells and preventing oxidative stress.

In some embodiments, a method may comprise contacting a photolabile visible light and/or UV absorber (e.g., excited to a singlet and/or triplet excited state) with a with a conjugated fused polycyclic compound. As a result, the light absorber is returned to its ground state so that it can absorb more UV radiation, thereby protecting the skin for longer durations.

Photounstable UV absorber may include, for example, dibenzoylmethane derivatives, such as butylmethoxy dibenzoylmethane (Avobenzone). Porphyrins may include, for example, protoporphyrin IX and other endogenous chromophores. Donor and/or acceptor molecules may be included in photoactive sunscreen, cosmetic and dermatological compositions.

According to some embodiments, the present disclosure relates to compositions for resolving an excited state of a donor molecule. A composition may comprise, for example, a molecule of Formula I, II, and/or III. In some embodiments, where $R_1$, $R_2$, $R_{13}$, and $R_{14}$ are selected from nitrile and C(O)OMe, $R_1 \neq R_2$, and $R_{13} \neq R_{14}$, a compound of Formula I, II or III may be selected from:

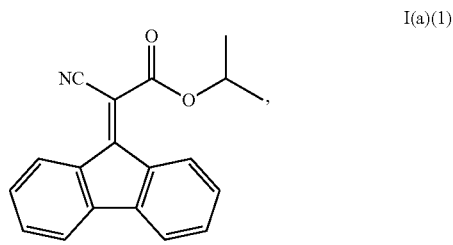

I(a)(1)

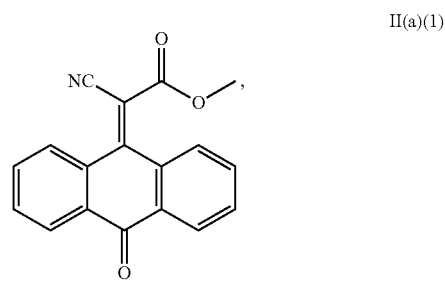 [SMILES: COC(=O)C(C#N)=C1c2ccccc2C(=S)c2ccccc21]

II(a)(1)

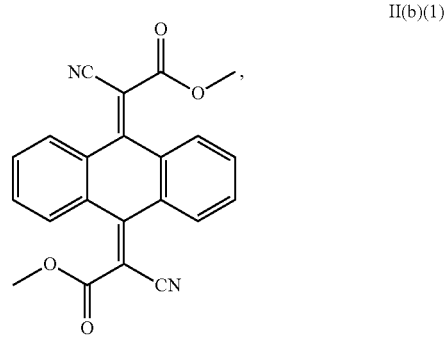

II(b)(1)

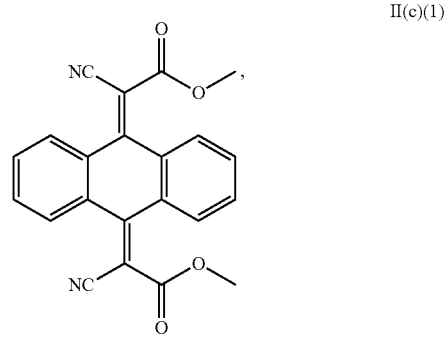

II(c)(1)

II(d)(1)
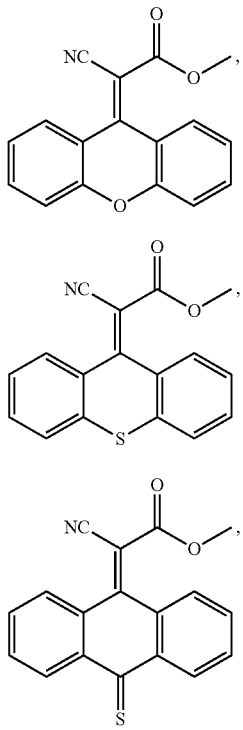

and/or combinations thereof.

According to some embodiments, where $R_1=R_2=C(O)OMe$, $A_1$ is $C=C(R_{13})R_{14}$, for which $R_{13}, =R_{14}=C(O)OMe$, and $A_2$ is as shown in Formula II, a compound of Formula I, II or III may be selected from:

I(b)(1)
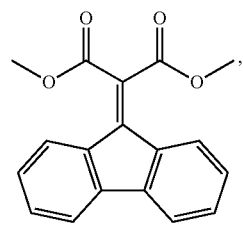

II(g)(1)
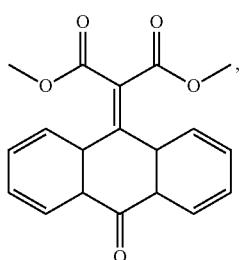

II(h)(1)
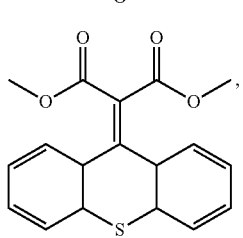

II(i)(1)
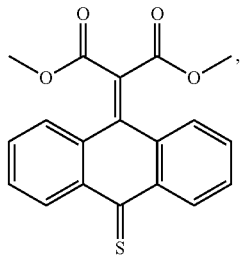

II(j)(1)
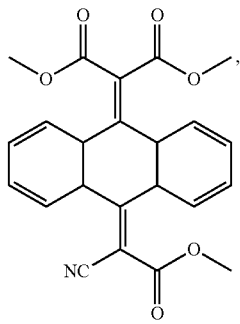

II(k)(1)
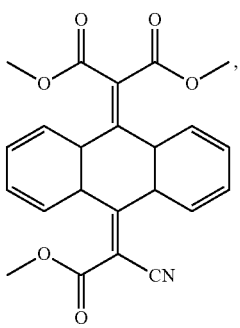

II(b1)(1)
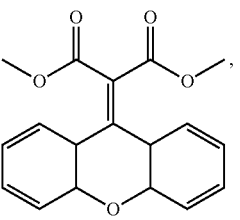

and/or combinations thereof.

A conjugated fused polycyclic compound of Formulas I, II, and/or III may be included in a composition (e.g., a cosmetic or dermatological composition) at any desired concentration. For example, conjugated fused polycyclic compound may be included in a cosmetic or dermatological composition in an amount of about 0.01% by weight to about 20% by weight, from about 0.1 to about 20% by weight, or from about 0.1% to about 10% by weight, in each case based on the total weight of the composition.

In some embodiments, a donor molecule may comprise a pigment (e.g., a porphyrin). A photodegradable pigment may include, according to some embodiments, exogenous pigments, such as exogenous porphyrin compounds, or endogenous pigments, such as non-hematogenous pigments, hematogenous (i.e., blood derived) pigments, or mixtures thereof. In some embodiments, an endogenous photodegradable pigment is a non-hematogenous pigment, such as, for example, melanins, flavins, pterins, and/or urocanic acid. A photodegradable non-hematogenous pigment may comprise, in some embodiments, a melanin, such as, for example, eumelanin, pheomelanin, neuromelanin, or mixtures thereof. According to some embodiments, a photodegradable non-hematogenous pigment may comprise a flavin, such as, for example, riboflavin, flavin mononucleotide, a flavoprotein, and/or flavin adenine dinucleotide. A photodegradable non-hematogenous pigment may comprise a pterin, such as, for example, pteridine, biopterin, tetrahydrobiopterin, molybdopterin, cyanopterin, tetrahydromethanopterin, folic acid, and combinations thereof, according to some embodiments. A photodegradable endogenous pigment may be, in some embodiments, a hematogenous pigment, for example, hemoglobin, bile pigments, porphyrins, and mixtures thereof. In some embodiments, the photodegradable hematogenous pigment is a bile pigment. In some embodiments, the bile pigment is bilirubin, biliverdin, or a mixture thereof.

A porphyrin may have its singlet and/or triplet excited states resolved (e.g., quenched) by a conjugated fused polycyclic molecule, according to some embodiments. A porphyrin may comprise the moiety of Formula IV (and derivatives and tautomers thereof), as shown in Formula IVa, and Formula IVb (protoporphyrin IX). Porphyrins are a group of organic compounds, mainly naturally occurring. One of the best-known porphyrins is heme, the pigment in red blood cells.

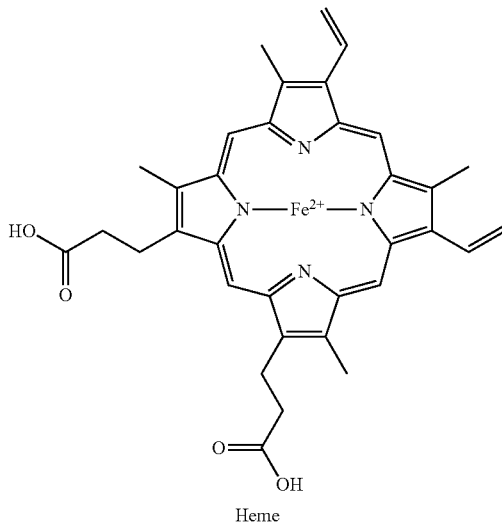

Heme

Heme is a cofactor of the protein hemoglobin. Porphyrins are heterocyclic macrocycles composed of four modified pyrrole subunits interconnected at their a carbon atoms via methine bridges (=CH—), as shown in Formula I. Porphyrins are aromatic. That is, they obey Hückel's rule for aromaticity, possessing $4n+2$ $\pi$ electrons ($n=4$ for the shortest cyclic path) delocalized over the macrocycle. Thus, porphyrin macrocycles are highly conjugated systems and typically have very intense absorption bands in the visible region and may be deeply colored. The macrocycle has 26 $\pi$ electrons in total. The parent porphyrin is porphine, and substituted porphines are called porphyrins.

According to some embodiments, a porphyrin without a metal-ion in its cavity is a free base. A porphyrin may comprise a chelated metal (e.g., having a 2+ or 3+ oxidation state). A chelated metal may include, for example, beryllium, magnesium, aluminum, calcium, strontium, barium, radium, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, indium, tin, lead, and platinum.

Some iron-containing porphyrins are called hemes. Heme-containing proteins, or hemoproteins, are found extensively in nature. Hemoglobin and myoglobin are two $O_2$-binding proteins that contain iron porphyrins. Various cytochromes are also hemoproteins.

A porphyrin molecule in an electronically excited state can transfer its excited state energy to oxygen contained in blood and/or skin cells, thereby generating cell-damaging singlet excited state oxygen (hereinafter "singlet oxygen"), or free radical oxygen. According to some embodiments, a system may photostabilize the excited state of the porphyrin molecule so that it does not generate cell-toxic singlet oxygen, for example, by resolving the excited state of the porphyrin molecule, returning it to the ground state before it transfers its excited state energy to nearby oxygen molecule.

A porphyrin may include, in some embodiments, a porphyrin moiety according to Formula IV:

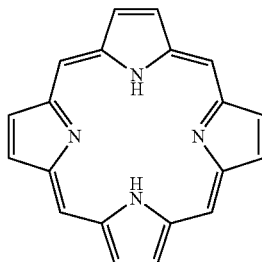

IV

A porphyrin may include, in some embodiments, a porphyrin moiety according to Formula IV(a):

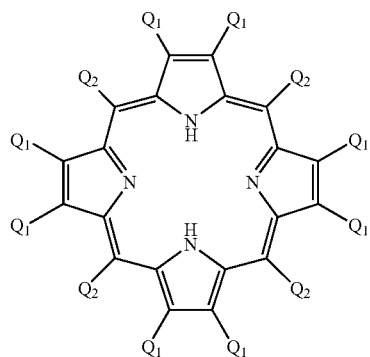

IV(a)

wherein:
each $Q_1$ may be independently selected from H, alkyl, alkenyl, alkynyl, hydroxyl, alkoxyl, carboxyl, carboxylic ester, amino, sulfhydryl, aryl, and heteroaryl; and,
each $Q_2$ may independently selected from H, alkyl, alkenyl, alkynyl, hydroxyl, alkoxyl, carboxyl, carboxylic ester, amino, sulfhydryl, aryl, and heteroaryl.

In some embodiments, each $Q_1$ may be independently selected from the group consisting of H, $C_1$-$C_6$ unsubstituted alkyl, $C_1$-$C_6$ hydroxyalkyl, $C_1$-$C_6$ carboxyalkyl, $C_1$-$C_6$ esteralkyl, $C_1$-$C_6$ sulfhydrylalkyl $C_1$-$C_6$ alkenyl, amino, aryl, and heteroaryl.

In some exemplary embodiments, each $Q_1$ may be independently selected from the group consisting of H, $C_1$-$C_4$ unsubstituted alkyl, $C_1$-$C_4$ hydroxyalkyl, $C_1$-$C_4$ carboxyalkyl, $C_1$-$C_4$ esteralkyl, $C_1$-$C_6$ sulfhydrylalkyl, $C_1$-$C_4$ alkenyl, aryl, and heteroaryl. For example, each $Q_1$ may be independently selected from the group consisting of H, methyl, ethyl, propyl, isopropyl, n-butyl, sec-butyl, isobutyl, tert-butyl, ethenyl, 1-propenyl, 2-propenyl, 1-hydroxyethyl, 2-hydroxyethyl, phenyl, acetic acid, methyl acetate, ethyl acetate, propionic acid, methyl propanate, ethylpropanate, and

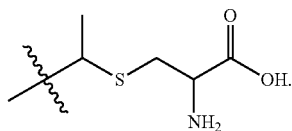

In some embodiments, each $Q_2$ may be independently selected from H, $C_1$-$C_6$ alkyl, $C_1$-$C_6$ alkenyl, aryl, and heteroaryl. Each $Q_2$ may be independently selected from H, $C_1$-$C_4$ alkyl, $C_1$-$C_4$ alkenyl, phenyl, naphthyl, and pyridyl, in some embodiments. For example, each $Q_2$ may be independently selected from H, phenyl, hydroxyphenyl, dihydroxyphenyl, trihydroxyphenyl, methoxyphenyl, dimethoxyphenyl, trimethoxyphenyl, carboxyphenyl, trimethylanilinium, naphthyl, sulfonatophenyl, pyridyl, and N-methylpyridyl.

Examples of a porphyrins that may attain an excited state may include 5-azaprotoporphyrin IX, bis-porphyrin, coproporphyrin III, deuteroporphyrin, deuteroporphyrin IX dichloride, diformyl deuteroprophyrin IX, dodecaphenylporphyrin, hematoporphyrin, hematoporphyrin IX, hematoporphyrin monomer, hematoporphyrin dimer, hematoporphyrin derivative, hematoporphyrin derivative A, hematoporphyrin IX dihydrochloride, hematoporphyrin dihydrochloride, mesoporphyrin, mesoporphyrin IX, monohydroxyethylvinyl deuteroporphyrin, 5,10,15,20-tetra(o-hydroxyphenyl)porphyrin, 5,10,15,20-tetra(m-hydroxyphenyl) porphyrin, 5,10,15,20-tetra(p-hydroxyphenyl) porphyrin, 5,10,15,20-tetrakis(3-methoxyphenyl)-porphyrin, 5,10,15,20-tetrakis(3,4-dimethoxyphenyl)porphyrin, 5,10,15,20-tetrakis(3,5-dimethoxyphenyl)porphyrin, 5,10,15,20-tetrakis(3,4,5-trimethoxyphenyl)porphyrin, 2,3,7,8,12,13,17,18-octaethyl-5,10,15,20-tetraphenylporphyrin, porphyrin c, protoporphyrin, protoporphyrin IX, tetra-(4-N-carboxyphenyl)-porphine, tetra-(3-methoxyphenyl)-porphine, tetra-(3-methoxy-2,4-difluorophenyl)-porphine, 5,10,15,20-tetrakis(4-N-methylpyridyl)porphine, tetra-(4-N-methylpyridyl)-porphine tetrachloride, tetra-(3-N-methylpyridyl)-porphine, tetra-(2-N-methylpyridyl)-porphine, tetra(4-N,N,N-trimethylanilinium)porphine, tetra-(4-N,N,N"-trimethylamino-phenyl)porphine tetrachloride, tetranaphthaloporphyrin, tetraphenylporphyrin, tetra-(4-sulfonatophenyl)-porphine, 4-sulfonatophenylporphine, uroporphyrin, uroporphyrin III, uroporphyrin IX, and uroporphyrin I, and esters thereof.

In some embodiments, a porphyrin compound may be an ester selected from the group consisting of 5-azaprotoporphyrin dimethylester, coproporphyrin III tetramethylester, deuteroporphyrin IX dimethylester, diformyl deuteroporphyrin IX dimethylester, hematoporphyrin IX dimethylester, mesoporphyrin dimethylester, mesoporphyrin IX dimethylester, monoformyl-monovinyl-deuteroporphyrin IX dimethylester, protoporphyrin dimethylester, and protoporphyrin IX dimethylester.

In some embodiments, a porphyrin compound may be selected from the group consisting of coproporphyrin III, coproporphyrin III tetramethylester, deuteroporphyrin, deuteroporphyrin IX dichloride, deuteroporphyrin IX dimethylester, hematoporphyrin, hematoporphyrin IX, hematoporphyrin derivative, hematoporphyrin derivative A, hematoporphyrin IX dihydrochloride, hematoporphyrin dihydrochloride, hematoporphyrin IX dimethylester, mesoporphyrin, mesoporphyrin dimethylester, mesoporphyrin IX, mesoporphyrin IX dimethylester, protoporphyrin, protoporphyrin IX, protoporphyrin dimethylester, protoporphyrin IX dimethylester, uroporphyrin, uroporphyrin III, uroporphyrin IX, and uroporphyrin I.

For example, a porphyrin compound may include protoporphyrin IX, deuteroporphyrin IX dichloride, deuteroporphyrin IX dimethylester, hematoporphyrin, hematoporphyrin IX, hematoporphyrin derivative, mesoporphyrin dimethylester, mesoporphyrin IX, or mesoporphyrin IX dimethylester.

According to some embodiments, a porphyrin compound may comprise protoporphyrin IX:

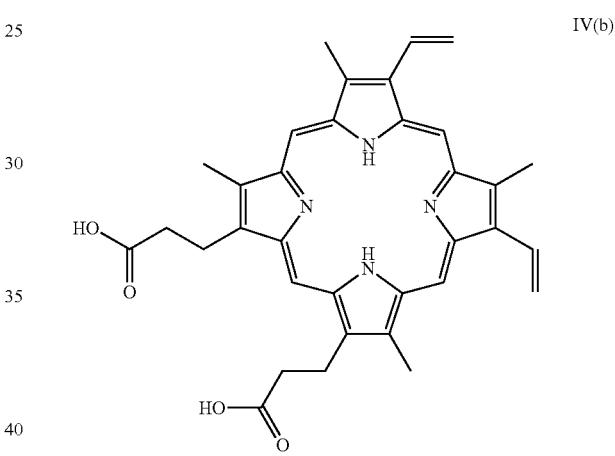

IV(b)

In some embodiments, a conjugated fused tricyclic compound of Formulas I, II, and/or III (e.g., II(a), II(b), II(d), II(e), II(c)) may be included in a cosmetic or dermatological composition for coating a skin surface to protect the skin from getting damaging amounts of singlet oxygen when skin cell-contained or blood-contained porphyrin compounds (e.g., protoporphyrin IX), are exposed to sunlight, or other visible light.

A dibenzoylmethane derivative may be selected from the group consisting of 2-methyldibenzoylmethane; 4-methyldibenzoylmethane; 4-isopropyldibenzoylmethane; 4-tert-butyldibenzoylmethane; 2,4-dimethydibenzoylmethane; 2-5-dimethydibenzoylmethane; 4,4'-diisopropyldibenzoylmethane; 4,4'-dimethoxydibenzoylmethane; 4-tert-butyl-4'-methoxdibenzoylmethane; 2-methyl-5-isopropy-4'-methoxydibenzoylmethane; 2-methyl-5-tert-butyl-4'-methoxydibenzoylmethane; 2,4-dimethyl-4'-methoxydibenzoymethane; 2,6-dimethyl-4-tert-butyl-4'-methoxydibenzolmthane, and combinations thereof. A compound according to Formulas I, II, and/or III may also photostabilize retinoids, coenzyme Q, cholecalciferol, and/or resveratrol.

In some embodiments, a sunscreen, cosmetic or dermatological composition described herein may comprise one or more fused tricyclic compounds as well as one or more UV-absorbing, chromophore-containing compounds. For example, a composition may include both UV-A and UV-B photoactive compounds in a cosmetically acceptable carrier, optionally including additives, such as emollients, stabilizers, emulsifiers, and combinations thereof. These additives may be used in preparing a UV filter composition in an emulsion (oil-in-water or water-in-oil) from a composition that includes one or more photoactive compounds and a solvent or a solvent combination that includes one or more organic solvents and water. When made, an emulsion may be an oil-in-water emulsion, wherein the oil phase is primarily formed from a mixture of the UV filter compound(s) including, for example, a dibenzoylmethane derivative, such as Avobenzone, and one or more organic solvents.

A photoactive composition may include one or more photoactive compounds, wherein the photoactive compound(s) act to absorb UV radiation and thereby protect the substrate (e.g., human skin, resins, films, and the like) from the harmful effects of UV radiation. Absorption may cause a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, many of those pathways adversely affect the ability of the photoactive compound to further absorb UV radiation. Conjugated fused polycyclic molecules may accept electronic singlet excited state energy from UV-absorbers, such as Avobenzone, octyl methoxycinnamate (Octinoxate), and octyl salicylate (Octisalate). Conjugated fused polycyclic compounds may be effective UVA absorbers in addition to providing electronic singlet state energy quenching of other UV-absorbing compounds in sunscreen, cosmetic and dermatological compositions. In some embodiments, the efficacy of conjugated fused polycyclic molecules may be enhanced (e.g., synergistically enhanced) when combined with one or more additional electronic singlet excited state quenching compounds such as oxybenzone and/or an alkoxy crylene. Photostabilization may be achieved in sunscreen compositions containing conjugated fused polycyclic molecules described herein together with octyl methoxycinnamate and Avobenzone.

A photoactive compound is one that responds to light (e.g., visible, UV light) photoelectrically. For example, photoactive compound-containing compositions that respond to UV radiation photoelectrically by photoactive compound photodegradation may benefit by the inclusion of conjugated fused polycyclicmolecules described herein. Conjugated fused polycyclic compounds, according to some embodiments, are useful photostabilizers and/or photoactive compounds when combined with any single or combination of photoactive compounds.

In some embodiments, a photoactive compound may be selected from the group consisting of p-aminobenzoic acid and salts and derivatives thereof; anthranilate and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naptholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxdydiphenyldisulfonate and salts and derivatives thereof; coumarin and derivatives thereof; diazole derivatives; quinine derivatives and salts thereof; quinoline derivatives; hydroxyl-substituted benzophenone derivatives; naphthalate derivatives; methoxy-substituted benzophenone derivatives; uric acid derivatives; vilouric acid derivatives; tannic acid and derivatives thereof; hydroquinone; benzophenone derivatives; 1,3,5-triazine derivatives; phenyldibenzimidazole tetrasulfonate and salts and derivatives thereof; terephthalyidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; and combinations of the foregoing.

A cosmetic or dermatological composition may include a cinnamate ester, such as 2-ethylhexyl p-methoxycinnamate, isoamyl p-methoxycinnamate, and a combination thereof. For example, a cinnamate ester may be 2-ethylhexyl p-methoxycinnamate. In some embodiments, a cinnamate ester may be present in the composition in an amount in a range of about 0.1 wt. % to about 15 wt. %, based on the total weight of the composition.

The cosmetic or dermatological composition also may include about 0.1 to about 10 wt. % of a triplet quencher selected from the group consisting of octocrylene, methyl benzylidene camphor, diethylhexyl 2,6-naphthalate, and combinations thereof.

In some embodiments, a cosmetic or dermatological composition may also include a UVA filter and/or UVB filter compound and/or a broad-band filter compound for protection of the skin from UVA and/or UVB wavelengths. Photostability is a problem with all UV filters because they all reach an electronic singlet excited state upon exposure to UV radiation. According to some embodiments, filters that may be photostabilized by a conjugated fused polycyclic molecule may include p-aminobenzoic acid, its salts and its derivatives (e.g., ethyl, isobutyl, glyceryl esters, p-dimethylaminobenzoic acid); anthranilates (e.g., o-aminobenzoates, methyl, menthyl, phenyl, benzyl, phenylethyl, linalyl, terpinyl, and cyclohexenyl esters); salicylates (e.g., octyl, amyl, phenyl, benzyl, menthyl (homosalate), glyceryl, and dipropyleneglycol esters); cinnamic acid derivatives (e.g., menthyl and benzyl esters, alpha-phenyl cinnamonitrile, butyl cinnamoyl pyruvate); dihydroxycinnamic acid derivatives (e.g., umbelliferone, methylumbelliferone, methylaceto-umbelliferone); camphor derivatives (e.g., 3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (e.g., esculetin, methylesculetin, daphnetin, and the glucosides, esculin and daphnin); hydrocarbons (e.g., diphenylbutadiene, stilbene); dibenzalacetone; benzalacetophenone; naphtholsulfonates (e.g., sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (e.g., 7-hydroxy, 7-methyl, 3-phenyl); diazoles (e.g., 2-acetyl-3-bromoindazole, phenyl benzoxazole, methyl naphthoxazole, various aryl benzothiazoles); quinine salts (e.g., bisulfate, sulfate, chloride, oleate, and tannate); quinoline derivatives (e.g., 8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (e.g., oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane). For example, UV filters that may be photostabilized by a conjugated fused polycyclic molecule may include 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)]aminobenzoate, 2-ethylhexylsalicylate, glycerol p-aminobenzoate, 3,3,5-trimethylcyclohexylsalicylate, and combinations thereof.

Photoactive compositions disclosed herein may include one or more photoactive compounds, according to some embodiments. For example, a photoactive composition may comprise one or more UV-A photoactive compounds and one or more UV-B photoactive compounds. A sunscreen composition may include a photoactive compound selected from the group consisting of p-aminobenzoic acid and salts and derivatives thereof anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxynaphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and combinations of the foregoing.

UV A radiation (about 320 nm to about 400 nm), is recognized as contributing to causing damage to skin, particularly to very lightly colored or sensitive skin. A sunscreen composition may include a UV-A photoactive compound (e.g., a dibenzoylmethane derivative UV-A photoactive compound). Examples of a UV-A absorbing dibenzoylmethane derivative may include include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

For a product marketed in the United States, cosmetically acceptable photoactive compounds and concentrations (reported as a percentage by weight of the total cosmetic sunscreen composition) may include: aminobenzoic acid (also called para aminobenzoic acid and PABA; 15% or less), Avobenzone (also called butyl methoxy dibenzoylmethane; 3% or less), cinoxate (also called 2 ethoxyethyl p methoxycinnamate; 3% or less), dioxybenzone (also called benzophenone 8; 3% or less), homosalate ((also called 3,3,5-trimethylcyclohexyl salicylate, 15% or less), menthyl anthranilate (also called menthyl 2 aminobenzoate; 5% or less), octocrylene (also called 2 ethylhexyl 2 cyano 3,3 diphenylacrylate; 10% or less), octyl methoxycinnamate (7.5% or less), octyl salicylate (also called 2 ethylhexyl salicylate; 5% or less), oxybenzone (also called benzophenone 3; 6% or less), padimate O (also called octyl dimethyl PABA; 8% or less), phenylbenzimidazole sulfonic acid (water soluble; 4% or less), sulisobenzone (also called benzophenone 4; 10% or less), titanium dioxide (25% or less), trolamine salicylate (also called triethanolamine salicylate; 12% or less), and zinc oxide (25% or less).

Other cosmetically acceptable photoactive compounds and concentrations (percent by weight of the total cosmetic sunscreen composition) may include diethanolamine methoxycinnamate (10% or less), ethyl-[bis(hydroxypropyl)]aminobenzoate (5% or less), glyceryl aminobenzoate (3% or less), 4 isopropyl dibenzoylmethane (5% or less), 4 methylbenzylidene camphor (6% or less), terephthalylidene dicamphor sulfonic acid (10% or less), and sulisobenzone (also called benzophenone 4, 10% or less).

For a product marketed in the European Union, cosmetically acceptable photoactive compounds and concentrations (reported as a percentage by weight of the total cosmetic sunscreen composition) may include: PABA (5% or less), camphor benzalkonium methosulfate (6% or less), homosalate (10% or less), benzophenone 3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG 25 PABA (10% or less), isoamyl p methoxycinnamate (10% or less), ethylhexyl triazone (5% or less), drometrizole trieloxane (15% or less), diethylhexyl butamido triazone (10% or less), 4 methylbenzylidene camphor (4% or less), 3 benzylidene camphor (2% or less), ethylhexyl salicylate (5% or less), ethylhexyl dimethyl PABA (8% or less), benzophenone 4 (5%, expressed as acid), methylene bis benztriazolyl tetramethylbutylphenol (10% or less), disodium phenyl dibenzimidazole tetrasulfonate (10% or less, expressed as acid), bis ethylhexyloxyphenol methoxyphenol triazine (10% or less), methylene bisbenzotriazolyl tetramethylbutylphenol (10% or less, also called TINOSORB M or Bisoctrizole), and bisethylhexyloxyphenol methoxyphenyl triazine. (10% or less, also called TINOSORB S or Bemotrizinol).

Addition of polar solvents to the oil phase of a composition may, in some embodiments, increase the photostability of photoactive compounds (e.g., in a sunscreen composition). In some embodiments, a sunscreen composition may comprise one or more highly polar solvents in the oil-phase of the composition. For example, a sufficient amount of a polar solvent may be present in a sunscreen composition to raise the dielectric constant of the oil-phase of the composition to a dielectric constant of at least about 7 (e.g., at least about 8).

A photoactive compound may be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for Avobenzone). Likewise, a sunscreen composition may include a plurality of photoactive compounds and a sunscreen composition, as a whole, may be considered stable when, for example, after 30 MED irradiation the sunscreen composition has retained at least about 90% of its original absorbance at one or more wavelengths of interest (e.g., at or near the peak absorbance wavelength of the primary photoactive compound).

According to some embodiments, a conjugated fused polycyclic molecule may be included in a sunscreen, cosmetic or dermatological formulation with a water soluble UV filter compound and/or a broad-band filter compound. A cosmetic or dermatological formulation optionally may further include a dibenzoylmethane derivative and/or a dialkyl naphthalate.

Water-soluble UV filter substances may include, in some embodiments, sulfonated UV filters. For example, water-soluble UV filter substances may include: phenylene-1,4-bis(2-benzimidazyl)-3,3'-5,5'-tetrasulfonic acid, which has the following structure:

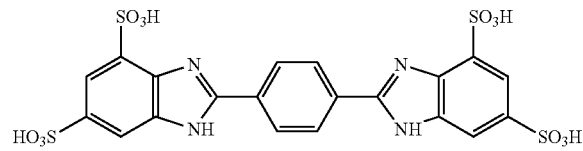

and its salts, especially the corresponding sodium, potassium or triethanolammonium salts, in particular phenylene-1,4-bis(2-benzimidazyl)-3,3'-5,5'-tetrasulfonic acid bissodium salt

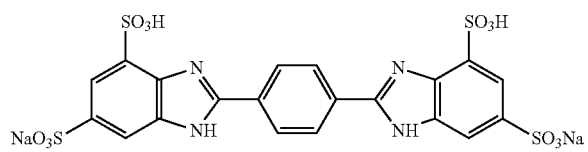

with the INCI name disodium phenyl dibenzimidazole tetrasulfonate (CAS No.: 180898-37-7), which is obtainable for example under the proprietary name Neo Heliopan A P from Haarmann & Reimer.

Examples of sulfonated UV filters may include salts of 2-phenylbenzimidazole-5-sulfonic acid, such as its sodium, potassium or its triethanolammonium salts, and the sulfonic acid itself

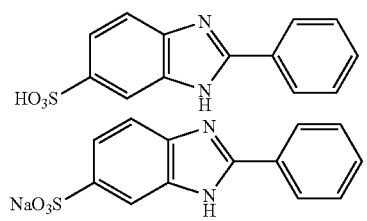

with the INCI name phenylbenzimidazole sulfonic acid (CAS No. 27503-81-7), which is obtainable for example under the proprietary name Eusolex 232 from Merck or under Neo Heliopan Hydro from Haarmann & Reimer.

Water-soluble UV B and/or broad-band filter substances may include, in some embodiments, sulfonic acid derivatives of 3-benzylidenecamphor, such as, for example, 4-(2-oxo-3-bornylidenemethyl)benzene-sulfonic acid, 2-methyl-5-(2-oxo-3-bornylidenemethyl)sulfonic acid and the salts thereof.

The total amount of one or more water-soluble UV filter substances in the finished cosmetic or dermatological preparations may be chosen from the range 0.01% by weight to about 20% by weight, from about 0.1 to about 20% by weight, or from about 0.1% to about 10% by weight, in each case based on the total weight of the composition.

According to some embodiments, a conjugated fused polycyclic molecule according to Formulas I, II, and/or III(e.g., I(a), I(a)(1), II(a), II(a)(1), II(b), II(b)(1), II(d), II(d)(1), II(e), II(e)(1), II(c), II(c)(1), and combinations thereof) may be included in sunscreen, cosmetic or dermatological formulation with a hydroxybenzophenone compound and/or a broad-band filter compound and optionally together with a dibenzoylmethane derivative and/or a dialkyl naphthalate.

According to some embodiments, a composition having a conjugated fused polycyclic molecule may have no need to comprise (e.g., may exclude) other UV photostabilizers.

A hydroxybenzophenone may have the following structural formula:

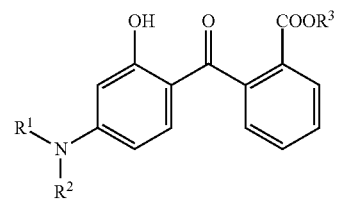

where $R^1$ and $R^2$ independent of one another are hydrogen, $C_1$-$C_{20}$-alkyl, $C_3$-$C_{10}$-cycloalkyl or $C_3$-$C_{10}$-cyloalkenyl, wherein the substituents $R^1$ and $R^2$ together with the nitrogen atom to which they are bound can form a 5- or 6-ring and $R^3$ is a $C_1$-$C_2$0 alkyl radical.

For example, a hydroxybenzophenone may comprise 2-(4'-diethylamino-2'-hydroxybenzoyl)benzoic acid hexyl ester (also: aminobenzophenone) having the structure

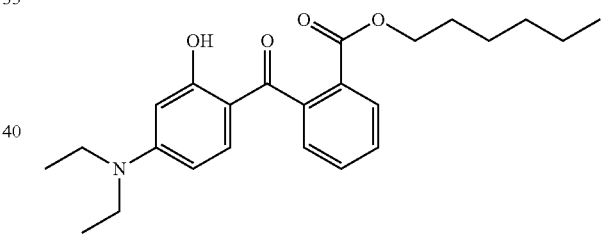

and is available from BASF under the Uvinul A Plus.

According to some embodiments, sunscreen, cosmetic or dermatological preparations may comprise 0.1 to 20% by weight, 0.1 to 15% by weight, and/or 0.1 to 10% by weight, of one or more hydroxybenzophenones.

According to some embodiments, sunscreen, cosmetic or dermatological preparations may comprise about 0.001% to about 30% by weight, about 0.01% to about 20% by weight, and/or about 0.5 to about 15% by weight, of one or more dialkyl naphthalates available, for example, under the trade name Hallbrite TQ™ from HallStar Innovaction Corp. or Corapan TQ™ from H&R. Dialkyl naphthalates may comprise branched alkyl groups with 6 to 10 carbon atoms According to some embodiments, a cosmetic or dermatological light-protection composition may be formulated for use as a sunscreen, cosmetic or dermatological light-protection material and one or more additional purposes including, for example, treatment, care and cleansing of the skin and/or hair and as a cosmetic product in decorative cosmetics.

In some embodiments, a conjugated fused polycyclic molecule may be included in a composition with a benzotriazole derivative compound and/or a broad-band filter compound and optionally, together with a dibenzoylmethane derivative and/or a dialkyl naphthalate. An example of a benzotriazole derivative is 2,2'-methylenebis(6-(2H-benzotriazol-2-yl)-4-(1,1,3,3-tetramethylbutyl)phenol), which has the chemical structural formula

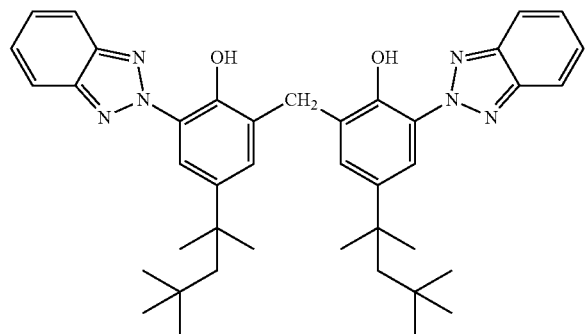 [SMILES: CC(C)(C)CC(C)(C)c1cc(Cc2cc(C(C)(C)CC(C)(C)C)cc(-n3nc4ccccc4n3)c2O)c(O)c(-n2nc3ccccc3n2)c1]

(INCL: bisoctyltriazole). It is obtainable under the proprietary name Tinosorb® from CIBA-Chemikalien GmbH and is distinguished by good UV absorption properties. The disadvantage of this substance is the characteristic of forming imperceptibly thin films on the skin which have unpleasant tactile properties.

According to some embodiments, a UV filter compound that may be included in a composition may be selected from UV filter compounds disclosed in published PCT application WO 2009/020676, hereby incorporated by reference (e.g., water-soluble, organic and particulate UV filter compounds).

In some embodiments, a UV filter compound may be a benzotriazle compound having the structure

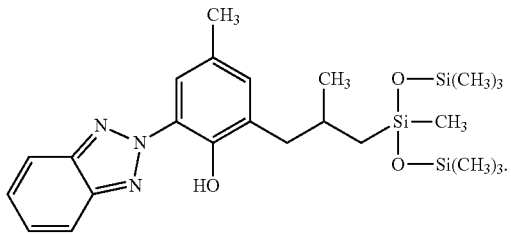

Particulate UV filter substances may include inorganic pigments. In some embodiments, inorganic pigments may include, for example, metal oxides and/or other metal compounds which are slightly soluble or insoluble in water. For example, an inorganic pigment may include oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

Zinc oxides may be used in the form of oily or aqueous predispersions. Zinc oxide particles and predispersions of zinc oxide particles which are suitable according to the disclosure may be distinguished by a primary particle size of <300 nm. Zinc oxide may include, for example, Z-Cote HP1 and Z-Cote from BASF and zinc oxide NDM from Haarmann & Reimer.

In some embodiments, titanium dioxide pigments may be in the form of both the rutile and anatase crystal modification and/or may be surface-treated ("coated"), for example, to form or retain a hydrophilic, amphiphilic or hydrophobic character. This surface treatment may consist of providing the pigments with a thin hydrophilic and/or hydrophobic inorganic and/or organic layer. The various surface coatings may contain water.

Inorganic surface coatings, in some embodiments, may comprise aluminum oxide ($Al_2O_3$), aluminum hydroxide $Al(OH)_3$ or aluminum oxide hydrate (also: alumina, CAS No.: 1333-84-2), sodium hexametaphosphate ($NaPO_3)_6$, sodium metaphosphate ($NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings, in some embodiments, may include one or more polymeric materials. Some examples of polymeric materials may include polyacrylate, polystyrene, polyester, polyurethanes, and copolymers thereof. These organic surface coatings may occur alone, in combination and/or in combination with inorganic coating materials.

Coated and uncoated titanium dioxides may be used in the form of oily or aqueous predispersions. In some embodiments, dispersion aids and/or solubilization mediators may be included.

According to some embodiments, a titanium dioxide may have a primary particle size of about 10 nm to about 150 nm. Examples of a titanium dioxide may include MT-100 Z and MT-100 TV from Tayca Corporation, Eusolex T-2000 from Merck and titanium dioxide T 805 from Degussa.

In some embodiments, pigments may comprise latex particles. Latex particles may include those described in the following publications: U.S. Pat. No. 5,663,213 and EP 0 761 201. Latex particles may be formed from water and styrene/acrylate copolymers (e.g., "Alliance SunSphere" from Rohm & Haas).

A compositions, according to some embodiments, may include one or more antioxidants. A composition may include any desired antioxidant, for example, an antioxidant suitable or conventional for cosmetic and/or dermatological applications.

An antioxidants may be selected, according to some embodiments, from amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, .gamma.-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. .gamma.-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyro-phenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients, which may be suitable according to some embodiments of the disclosure.

Thus, in some embodiments, a cosmetic or dermatological composition may include one or more oxidation-sensitive or UV-sensitive ingredients selected from the group consisting of retinoid compounds, coenzyme Q, cholecalciferol, resveratrol, carotenoid compounds, lipoic acid and derivatives thereof, vitamin E and derivatives thereof, vitamin F and derivatives thereof, and dioic acid in an amount from about 0.0001 wt % to about 10 wt %, based on the total weight of the composition.

In some embodiments, hydrophilic active ingredients (individually or in any combinations with one another) may be stabilized by their use together with one or more conjugated fused tricyclic compounds. Examples of hydrophilic active ingredients may include include biotin; carnitine and derivatives; creatine and derivatives; folic acid; pyridoxine; niacinamide; polyphenols (flavonoids, alpha-glucosylrutin); ascorbic acid and derivatives; Hamamelis; Aloe Vera; panthenol; and amino acids. In some embodiments, hydrophilic active ingredients may include water-soluble antioxidants, such as, for example, vitamins.

The amount of hydrophilic active ingredients (one or more compounds) in the preparations may be about 0.0001 to about 10% by weight (e.g., about 0.001 to about 5% by weight), based on the total weight of the preparation.

According to some embodiments, a composition may include one or more antioxidants. Examples of antioxidants may include all antioxidants customary or suitable for cosmetic and/or dermatological applications. The amount of antioxidants (one or more compounds) in the preparations may be about 0.001 to about 30% by weight, about 0.05 to about 20% by weight, about 0.1 to about 10% by weight, based on the total weight of the preparation.

The respective concentrations of vitamin E and/or derivatives thereof may be selected, in some embodiments, from the range about 0.001% to about 10% by weight, based on the total weight of the Formulation. According to some embodiments, the respective concentrations of vitamin A or vitamin A derivatives, or carotenes or derivatives thereof may be selected from the range from 0.001 to 10% by weight, based on the total weight of the formulation, according to some embodiments.

In some embodiments, a cosmetic preparation may comprise one or more cosmetic or dermatological active ingredients. Active ingredients may include, for example, antioxidants which may protect the skin against additional oxidative stress, natural active ingredients and/or derivatives thereof. Examples of active ingredients may include, for example, ubiquinones, retinoids, carotenoids, creatine, taurine and/or β-alanine.

Formulations, according to some embodiments of the disclosure, may comprise antiwrinkle active ingredients. For example, a formulation may comprise an antiwrinkle active ingredient selected from flavone glycosides (e.g., α-glycosylrutin), coenzyme Q10, vitamin E and/or derivatives and the like. Formulations comprising an antiwrinkle active ingredient may be suitable for the prophylaxis and/or treatment of cosmetic or dermatological changes in skin. Skin changes may include, for example changes that arise, for example, during skin aging. Formulations with an antiwrinkle active ingredient may be suitable for the prophylaxis and/or treatment of conditions including, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g., age spots), increased susceptibility to mechanical stress (e.g., cracking) and the like.

In some embodiments, cosmetic or dermatological compositions may include triazines, benzotriazoles, latex particles, organic pigments, inorganic pigments, and mixtures thereof.

A cosmetic or dermatological compositions may include conventional additives and solvents used for the treatment, care and cleansing of skin and/or the hair and as a make-up product in decorative cosmetics.

For use in protecting skin from oxidative stress, a cosmetic and/or dermatological compositions may contain about 0.01 wt. % to about 20 wt. % cyano-containing fused tricyclic compound(s) and the composition may be applied to the skin and/or the hair in a sufficient quantity in the manner customary for cosmetics.

A cosmetic and dermatological compositions described herein may comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological Formulation, such as alcohols, polyols, polymers, foam stabilizers, electrolytes, organic solvents or silicone derivatives.

The present disclosure relates, in some embodiments, to articles that may include a conjugated fused polycyclic molecule. Some examples of an article may include buildings, bridges, automobiles, appliances, boats, fabrics (e.g., garments), signs, and sports equipment (e.g., nets, balls, boards, flags). An article may be combined with a conjugated fused polycyclic molecule during manufacture or synthesis, according to some embodiments. A conjugated fused polycyclic molecule (e.g., a composition comprising a conjugated fused polycyclic molecule) may be applied to an article after it is formed.

The present disclosure relates, in some embodiments, systems for resolution of an excited energy state. A system may comprise, for example, a donor molecule (e.g., a porphyrin according to Formula IV) and/or an acceptor molecule (e.g., a polycyclic molecule according to Formula I or II).

In some embodiments, the disclosure relates to a method of suppressing the generation of singlet oxygen and/or other reactive oxygen species or radicals by an excited donor molecule (e.g., porphyrin, mammalian porphyrin). A method may include contacting an acceptor molecule with a donor molecule in any desired milieu. A method may include suppressing the formation of free radical oxygen, superoxide anion, peroxide, hydroxyl radical, and/or hydroxyl ion, in some embodiments.

In some embodiments, the disclosure relates to a method of quenching excited state energy from a pigment and/or porphyrin compound that has been excited by exposure to and absorption of light (e.g., having a wavelength in the wavelength range of 380-800 nm), comprising contacting (e.g., reacting) a pigment and/or porphyrin compound comprising a porphyrin moiety of Formula IV or a derivative or tautomer thereof with a polycyclic molecule according to Formula I or Formula II.

The disclosure further relates, according to some embodiments, to a method of protecting skin from oxidative stress caused by the generation of free radical oxygen comprising coating at least a portion of the skin with a porphyrin excited state quencher capable of accepting or donating an electron from or to a porphyrin compound in the excited state and returning the excited porphyrin compound to its ground state, said porphyrin quencher comprising a molecule according to Formulas I, II, and/or II.

In some embodiments, the disclosure relates to a method of quenching excited state energy from a porphyrin compound that has been excited by exposure to and absorption of light (e.g., having a wavelength in the wavelength range of 380-800 nm), comprising contacting (e.g., reacting) a porphyrin compound comprising a porphyrin moiety of Formula IV or a derivative or tautomer thereof with a polycyclic molecule according to Formula I or Formula II.

Excited states of porphyrins may be harnessed to administer photodynamic therapy (PDT). Protoporphyrin IX ($C_{34}H_{34}N_4O_4$) is used in PDT, for example, as a treatment for basal cell carcinoma (BCC), which is the most common form of skin cancer in humans. The PDT treatment involves applying a photosensitizer precursor, such as aminolevulinic acid (ALA) to the cancerous cells, waiting a few hours for the ALA to be taken up by the cells and converted to protoporphyrin IX, and then irradiating the cancerous cells with light in the wavelength of about 380 to about 650 nm. This illumination excites the protoporphyrin IX to a singlet excited state, after which it intersystem crosses to a triplet excited state, thereby making it reactive with oxygen. Consequently, cytotoxic singlet oxygen is generated that kills cancerous and pre-cancerous cells. To mitigate potentially adverse effects of PDT on non-carcinogenic cells, a molecule having Formula I or Formula II may be contacted with the cells to be protected.

In some embodiments, the disclosure relates to a method of protecting healthy cells adjacent to cancerous or pre-cancerous cells undergoing photodynamic therapy comprising applying a composition comprising an acceptor molecule (e.g., an acceptor according to Formulas I, II, and/or Formula III) to said adjacent cells to reduce the generation of free radical oxygen from said healthy cells while the photodynamic therapy generates free radical oxygen from said cancerous or pre-cancerous cells. In some embodiments, a composition may further comprise a porphyrin excited state quencher compound comprising a porphyrin moiety of Formula IV or a derivative or tautomer thereof.

Conjugated fused polycyclic molecules may be accessible through a condensation reaction between a carboxyl compound and an active hydrogen containing compound. Examples of such methods appear in the Examples below.

As will be understood by those skilled in the art who have the benefit of the instant disclosure, other equivalent or alternative compositions, objects, methods, and systems for quenching, dissipating, and/or otherwise resolving excited state energy can be envisioned without departing from the description contained herein. Accordingly, the manner of carrying out the disclosure as shown and described is to be construed as illustrative only.

Persons skilled in the art may make various changes in the kind, number, and/or arrangement of R-groups, substituents, and/or heteroatoms without departing from the scope of the instant disclosure. In addition, the size of an object and/or system may be scaled up or down to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, object, and/or system may be prepared and or used as appropriate for animal and/or human use (e.g., with regard to sanitary, infectivity, safety, toxicity, biometric, and other considerations). Elements, compositions, objects, systems, methods, and method steps not recited may be included or excluded as desired or required.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/−about 10%, depicted value +/−about 50%, depicted value +/−about 100%) and/or a range endpoint. With respect to the former, a value of 50 depicted in an example, table, and/or drawing may form the basis of a range of, for example, about 45 to about 55, about 25 to about 100, and/or about 0 to about 100. Disclosed percentages are weight percentages except where indicated otherwise.

All or a portion of an object and/or system for quenching, dissipating, and/or otherwise resolving excited state energy may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

Example 1: Absorption Spectra

Figures 2A, 2B:
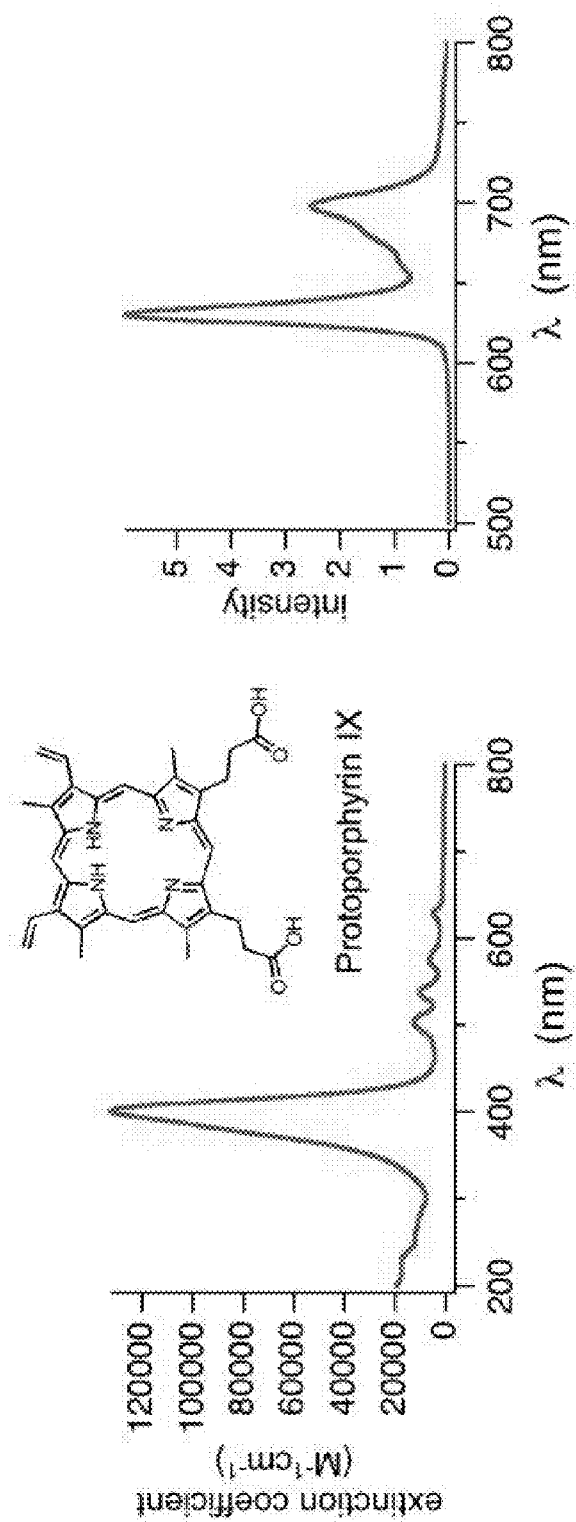
FIG. 2A illustrates an absorption spectrum of protoporphyrin IX in acetonitrile. λex=510 nm, according to a specific example embodiment of the disclosure.
FIG. 2B illustrates a fluorescence spectrum of protoporphyrin IX in acetonitrile. λex=510 nm, according to a specific example embodiment of the disclosure.

UV and visible light absorption spectra were recorded to investigate to what extent each stabilizer itself absorbs UV light. FIG. 1 reveals that the stabilizers are strong UV absorbers with large extinction coefficients (molar absorptivity) of 16,200 M-1 cm-1 (Formula I(a)(1); λmax=334 nm) and 13,200 M-1 cm-1 (SolaStayS1; λmax=336 nm). Protoporphyrin IX has weak absorption bands above 450 nm, where the two compounds are transparent (FIG. 2). The compound with the oxygen bridge (Formula II(d)(1)) caused a bathochromic shift of the UV absorption of the lowest energy band. The compound with the sulfur bridge (Formula II(e)(1)) shifted the lowest energy band further into the visible region.

Example 2: Protoporphyrin Quenchers—Singlet State

Photoexcitation in these absorption bands generates singlet excited states which deactivate to the ground state or intersystem cross to the triplet state. Formulas I, II, and/or III molecules and alkoxycrylene may target the singlet excited states and/or the triplet states.

Figures 3A, 3B:
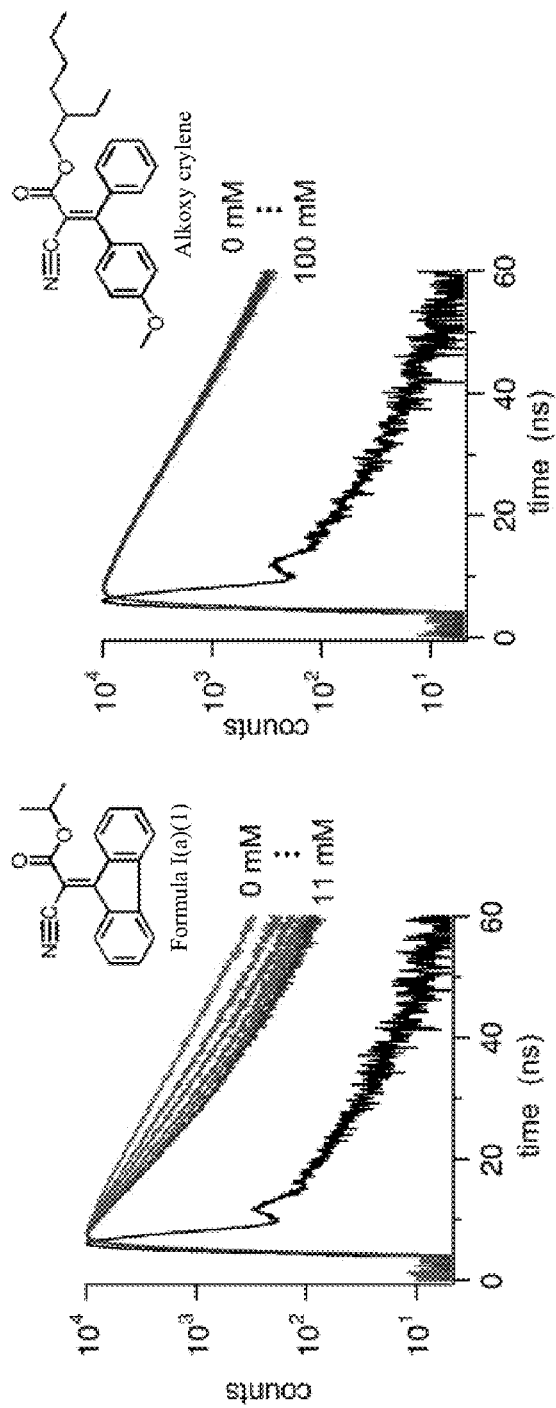
FIG. 3A illustrates fluorescence decay traces monitored at 690 nm using time correlated single photon counting of the compound of Formula I(a)(1) in acetonitrile solutions in the absence and presence of different amounts of stabilizers, according to a specific example embodiment of the disclosure.
FIG. 3B illustrates fluorescence decay traces monitored at 690 nm using time correlated single photon counting of alkoxy crylene in acetonitrile solutions in the absence and presence of different amounts of stabilizers, according to a specific example embodiment of the disclosure.

Fluorescence lifetime measurements are a convenient way to measure singlet state quenching by stabilizers. Protoporphyrin IX decay traces were recorded in the absence and presence of compound I(a)(1) and alkoxy crylene (FIG. 3). The experiments show that the compound of Formula I(a)(1) significantly quenches the protoporphyrin IX fluorescence (reduces fluorescence lifetime; FIG. 3). However, the alkoxy crylene compound caused no reduction in fluorescence lifetime, even at high concentrations, such as 0.1 M (FIG. 3).

Figure 4A:
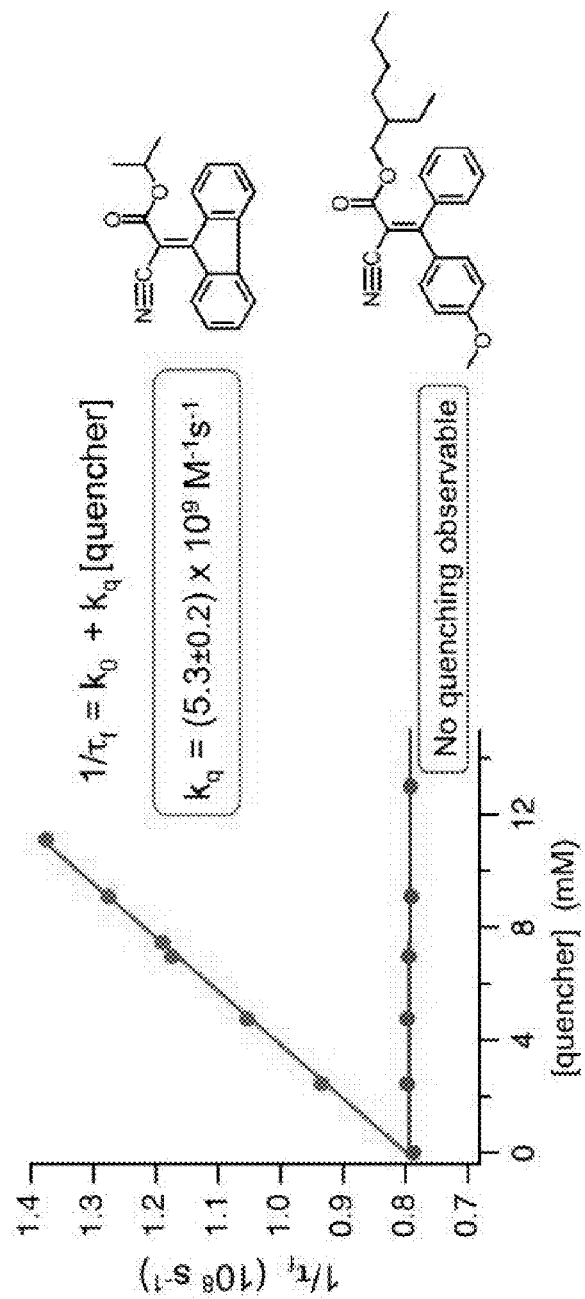
FIG. 4A is a graph showing inverse fluorescence lifetime vs. acceptor concentration used for determining $k_q$, the bimolecular rate constant for quenching of protoporphyrin IX fluorescence by the compounds of Formula I(a)(1) and alkoxy crylene, according to a specific example embodiment of the disclosure, using the experimental data shown in FIG. 3.
Figures 4B, 4C:
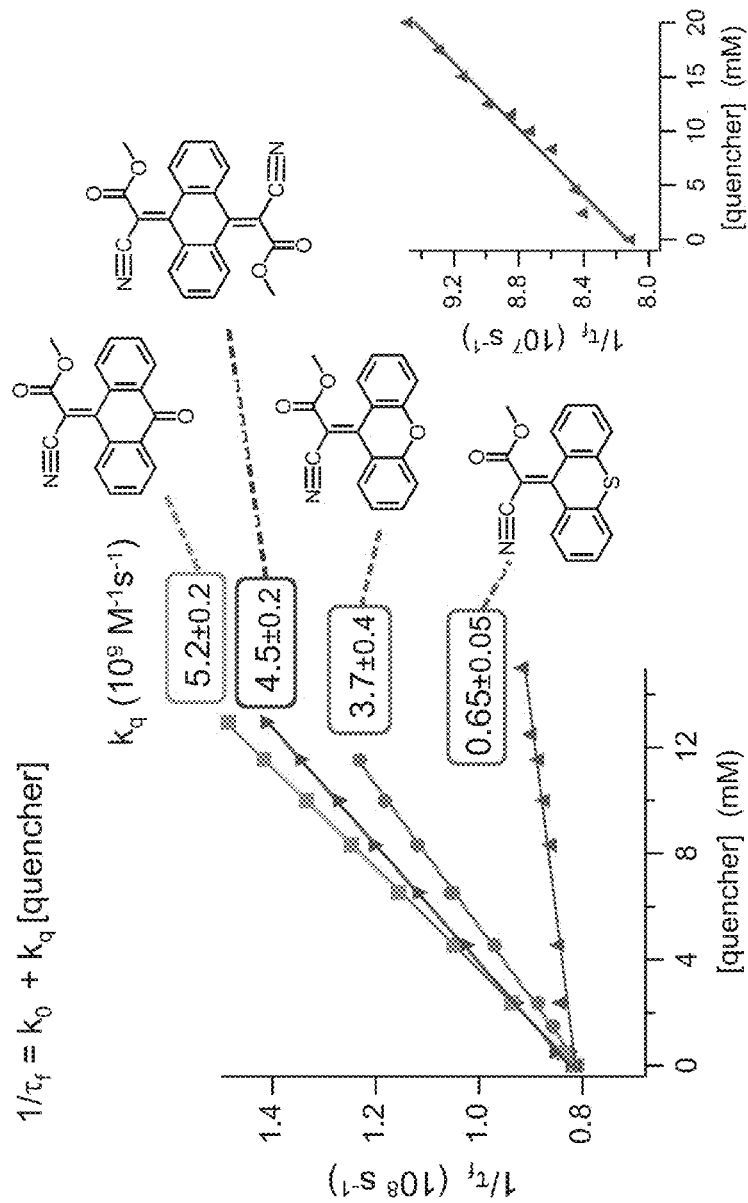
FIG. 4B is a graph showing inverse fluorescence lifetime vs. acceptor concentration used for determining $k_q$, the bimolecular rate constant for quenching of protoporphyrin IX fluorescence by the compounds of Formula II(a)(1), Formula II(d)(1), Formula II(e)(1), and a mixture of Formula II(b)(1) and II(c)(1), according to a specific example embodiment of the disclosure.
FIG. 4C is a graph in which the data shown in FIG. 4B for Formula II(e)(1) is plotted separate from the other data traces.

The collected data shown in FIG. 3 were used to determine the bimolecular quenching rate constant for singlet excited state quenching by the compounds. The quenching rate constant may be directly extracted from the slope of the plot of the inverse fluorescence lifetime vs. the concentration of the two compounds (FIG. 4). The data reveal a high quenching rate constant with the compound of Formulas I(a)(1), II(a)(1), II(d)(1), II(e)(1), and the mixture of II(b)(1) and II(c)(1) (close to the diffusion limit) but no observable quenching with the alkoxy crylene compound.

Example 3: Protoporphyrin Quenchers—Singlet State

To investigate if triplet states of protoporphyrin IX are quenched by the two compounds, laser flash photolysis experiments were performed. In these experiments, a deoxygenated acetonitrile solution of protoporphyrin IX is excited with short laser pulses from a Nd-YAG laser (355 nm, 5 ns pulse width). Difference absorption kinetic traces were recorded at different observation wavelengths (300 to 800 nm) and from these a transient absorption spectrum was constructed (FIG. 5A). This difference spectrum shows ground state depletion at 400 nm (where protoporphyrin IX absorbs strongly; see FIG. 2). In addition, two bands are observed at 320 and 440 nm, which are assigned to the triplet-triplet absorption of protoporphyrin IX. The triplet absorption decayed with a lifetime of 52 μs with subsequent recovery of the ground state absorption (FIG. 5B and FIG. 5C, respectively).

Figure 6A:
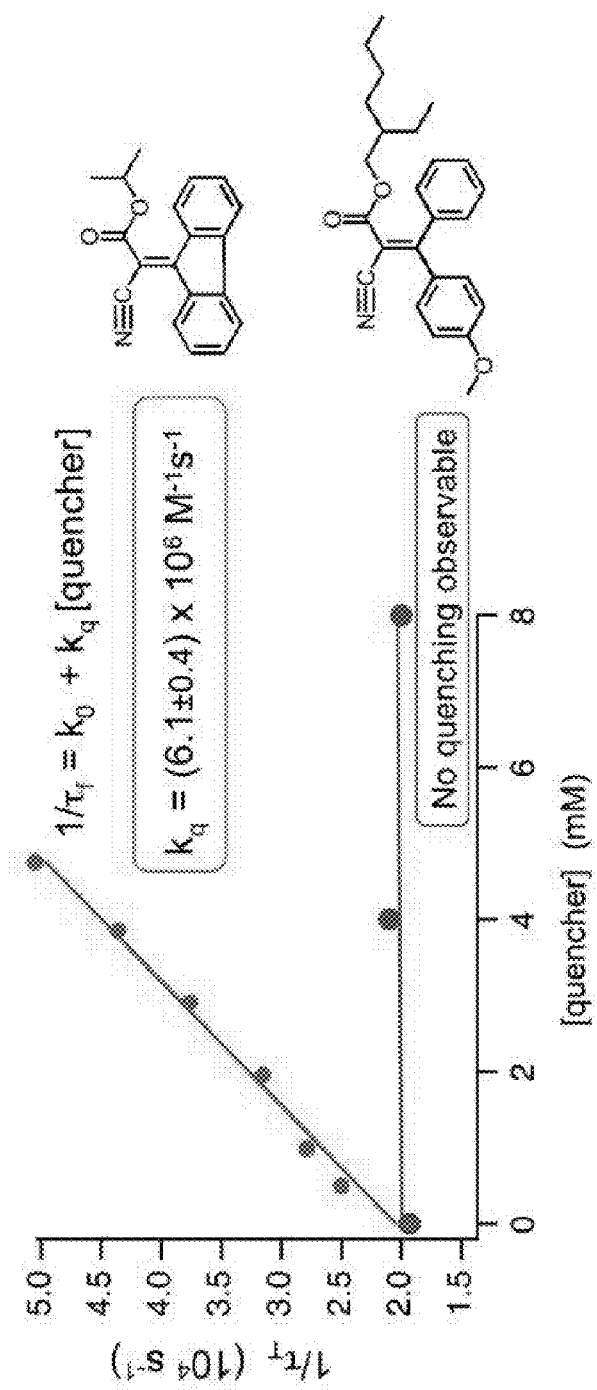
FIG. 6A is a graph showing inverse triplet state lifetime (measured at 440 nm by laser flash photolysis) vs. acceptor concentration used for determining $k_q$, the bimolecular rate constant for quenching of protoporphyrin IX triplet states by the compounds of Formula I(a)(1) and alkoxy crylene, according to a specific example embodiment of the disclosure.
Figures 6B, 6C, 6D:
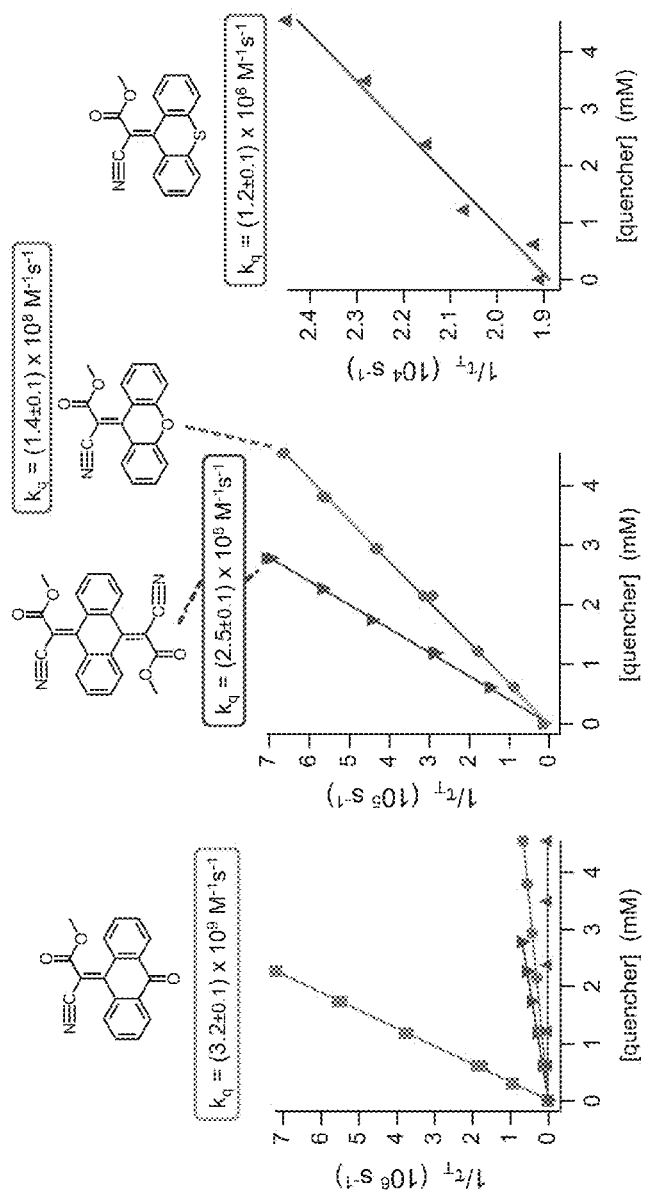
FIG. 6B is a graph showing inverse triplet state lifetime (measured at 440 nm by laser flash photolysis) vs. acceptor concentration used for determining $k_q$, the bimolecular rate constant for quenching of protoporphyrin IX triplet states by the compounds of Formula II(a)(1), according to a specific example embodiment of the disclosure.
FIG. 6C is a graph showing inverse triplet state lifetime (measured at 440 nm by laser flash photolysis) vs. acceptor concentration used for determining $k_q$, the bimolecular rate constant for quenching of protoporphyrin IX triplet states by the compounds of a mixture of Formula II(b)(1) and II(c)(1), according to a specific example embodiment of the disclosure.
FIG. 6D is a graph showing inverse triplet state lifetime (measured at 440 nm by laser flash photolysis) vs. acceptor concentration used for determining $k_q$, the bimolecular rate constant for quenching of protoporphyrin IX triplet states by the compounds of Formula II(e)(1), according to a specific example embodiment of the disclosure.

Triplet absorption kinetics at 440 nm may be utilized to obtain triplet quenching rate constants by the stabilizers. Triplet decay traces at 440 nm were recorded in the presence of different amounts of the alkoxy crylene, Formulas I(a)(1), II(a)(1), II(d)(1), II(e)(1), and the mixture of II(b)(1) and II(c)(1). The decay traces were fitted to a first-order kinetics. The plot of these pseudo-first-order rate constants (inverse decay lifetime) vs. the concentration of the two compounds gives directly the bimolecular triplet quenching rate constant from the slope (FIG. 6).

The triplet quenching rate constant for the compound of Formula I(a)(1) is three orders of magnitude smaller than singlet excited state quenching by the compound of Formula I(a)(1). However, since the triplet lifetime (52 μs) is more than three orders of magnitude larger than the singlet excited state lifetime (13 ns), the smaller rate constant for triplet quenching is compensated by the longer triplet lifetime. This makes protoporphyrin IX triplet state quenching by the compound of Formula I(a)(1) more efficient than singlet excited state quenching. Similar to the fluorescence quenching experiments, no triplet quenching was observed by the alkoxy crylene compound. Similarly, the triplet excited state quenching of PPIX varies over three orders of magnitude for Formula II(a)(1), II(d)(1), II(e) (1), and the mixture of II(b)(1) and II(c)(1). Interestingly, Formula II(a)(1) was the most efficient quencher—the PPIX triplet state quenching is almost as fast as the singlet state quenching.

Because Formula II(a)(1) contains a ketone functionality, intersystem crossing into the triplet state could be promoted after photoexcitation due to spin-orbit coupling. Stabilizer triplet states could generate singlet oxygen. Low-temperature luminescence experiments in a ethanol matrix at 77 K were performed in search for phosphorescence of potential triplet states. Only a very weak luminescence was observed with maximum at 492 nm and a quantum yield of less than 1%. Because the excitation spectrum of this luminescence did not match the absorption spectrum, it can be concluded that this luminescence is probably caused by an impurity and no long-lived triplet states of Formula II(a)(1) are formed.

Example 4: Mechanisms for Resolving Excited States—Control

Figures 7A, 7B, 7C:
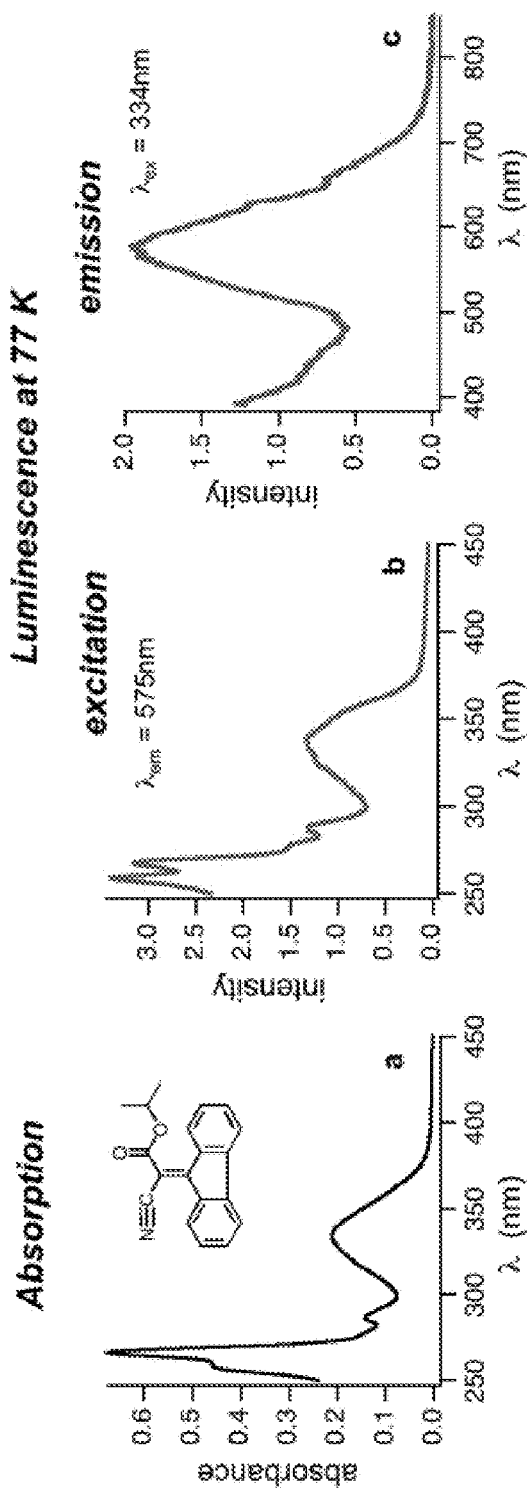
FIG. 7A illustrates an absorption spectrum of the compound of Formula I(a)(1) in ethanol solution at 77K, according to a specific example embodiment of the disclosure.
FIG. 7B illustrates a luminescence excitation spectrum of the compound of Formula I(a)(1) in ethanol solution at 77K, according to a specific example embodiment of the disclosure.
FIG. 7C illustrates a luminescence emission spectrum of the compound of Formula I(a)(1) in ethanol solution at 77K, according to a specific example embodiment of the disclosure.

The quenching mechanism of protoporphyrin IX singlet excited states and triplet states by the compound of Formulas I, II, and III may be further clarified. A simple energy transfer mechanism would depend on the singlet and triplet energies of compounds of Formula I and protoporphyrin IX. To get information on excited state energies of the stabilizer, luminescence experiments were performed. The compound of Formula I(a)(1) in ethanol solution did not give detectable fluorescence at room temperature. However, weak luminescence was observed of the compound of Formula I(a)(1) in a frozen ethanol matrix at 77 K. The luminescence with maximum at 575 nm (FIG. 7c) originates from the compound of Formula I(a)(1), because the luminescence excitation spectrum (FIG. 7b) matches well the absorption spectrum of the compound of Formula I(a)(1) (FIG. 5a). The luminescence lifetime could not be determined, because of the weak signal intensity. However, attempts to record time resolved luminescence spectra suggests that the lifetime is shorter than the microsecond time scale. This suggests that the luminescence at 575 nm is not a typical phosphorescence and probably is the fluorescence. If the luminescence at 575 nm is the fluorescence, then the Stoke's shift is unusually large. Independent of the assignment of the luminescence to the fluorescence or phosphorescence, this excited state energy is higher than singlet and triplet energies of protoporphyrin IX and rules out a simple energy transfer quenching mechanism. Another possible quenching mechanism is electron transfer quenching which would depend on the redox potentials of the protoporphyrin and the two quencher compounds.

Figures 8A, 8B:
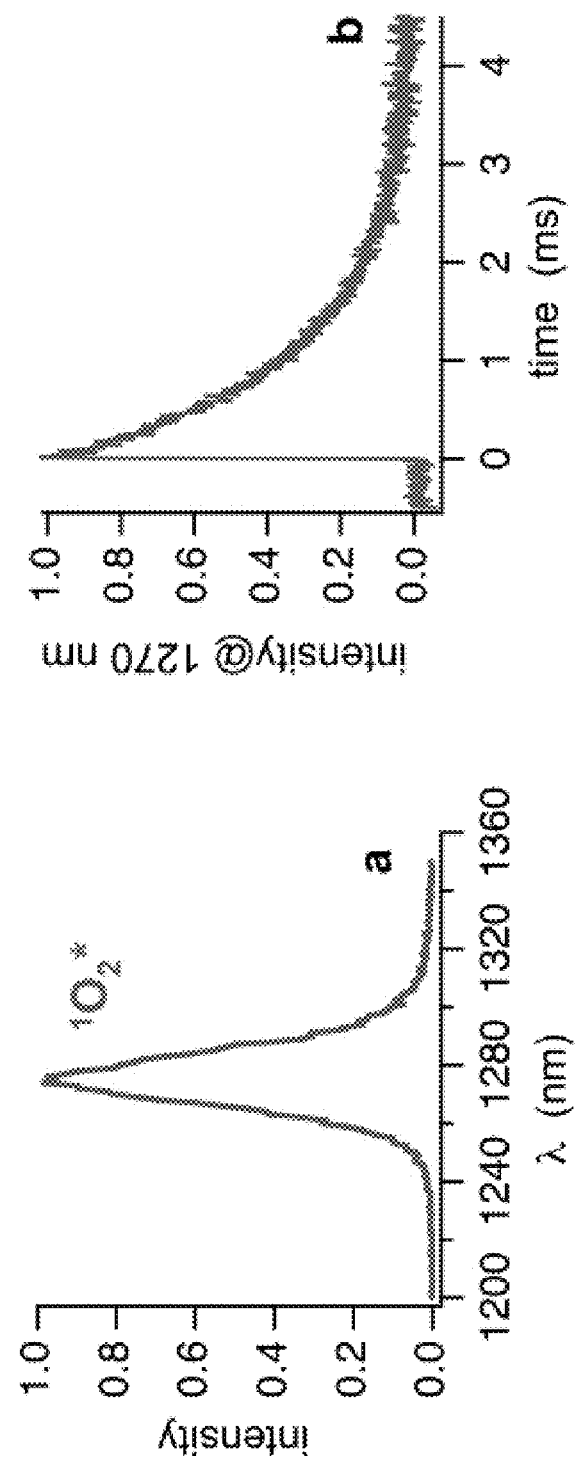
FIG. 8A illustrates a singlet oxygen phosphorescence spectrum generated by photoexcitation (532 nm) of tetrapenylporphyrin in air saturated $CCl_4$ solutions using steady-state lamp excitation, according to a specific example embodiment of the disclosure.
FIG. 8B illustrates a decay trace generated by photoexcitation (532 nm) of tetrapenylporphyrin in air saturated $CCl_4$ solutions using pulsed laser excitation, according to a specific example embodiment of the disclosure.
Figures 9A, 9B:
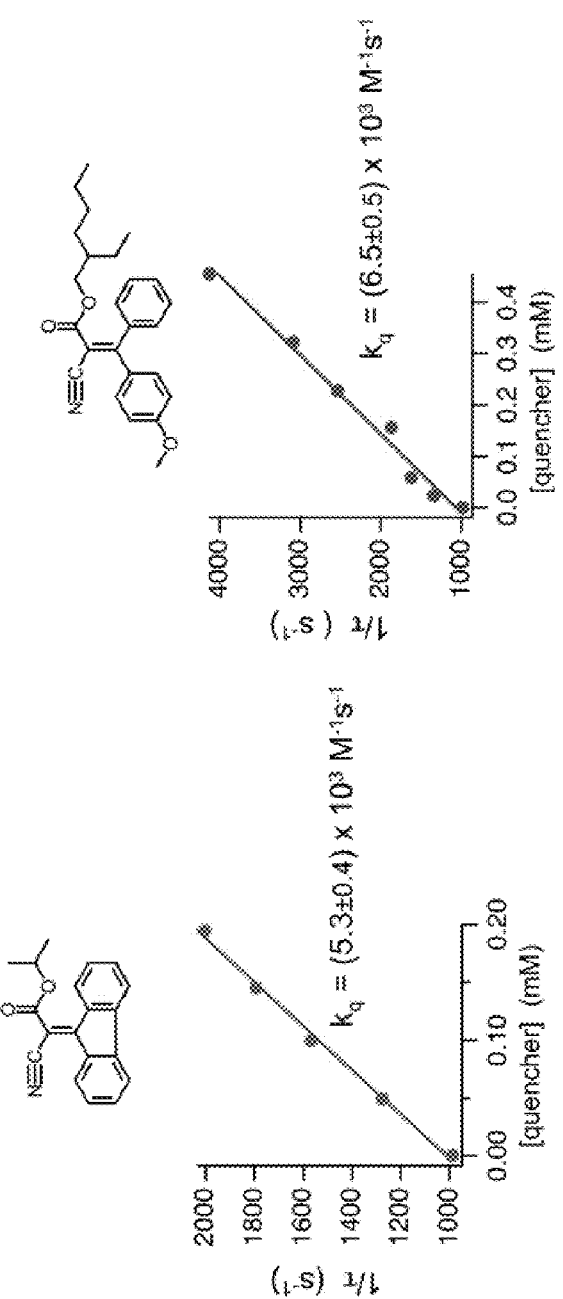
FIG. 9A illustrates inverse phosphorescence lifetime vs. absorption molecule concentration used to determine singlet oxygen quenching rate constants $k_q$ for Formula I(a)(1), according to a specific example embodiment of the disclosure.
FIG. 9B illustrates inverse phosphorescence lifetime vs. absorption molecule concentration used to determine singlet oxygen quenching rate constants $k_q$ for alkoxy crylene, according to a specific example embodiment of the disclosure.

Singlet oxygen quenching by compounds of Formula I is another possible photoprotection mechanism. A convenient way to generate singlet oxygen is by photoexcitation of tetraphenylporphyrin (TPP) in the presence of dissolved oxygen. FIG. 8 shows a typical singlet oxygen phosphorescence spectrum (FIG. 8A) and its decay trace (FIG. 8B). The solvent $CCl_4$ was selected, because it is known that the singlet oxygen has a long lifetime in this solvent (ms time scale), which makes the measurement of quenching kinetics easier. Singlet oxygen phosphorescence decay traces, such as shown in FIG. 8B, were recorded in the presence of different quencher concentrations. After fitting the decay traces to a first-order kinetic model, the bimolecular quenching constants were determined from the plots shown in FIG. 9. The singlet oxygen quenching rate constants of both compounds are relatively low. The slightly higher rate constant for the alkoxy crylene compound is consistent with the additional substituents compared to the compound of Formula I(a)(1).

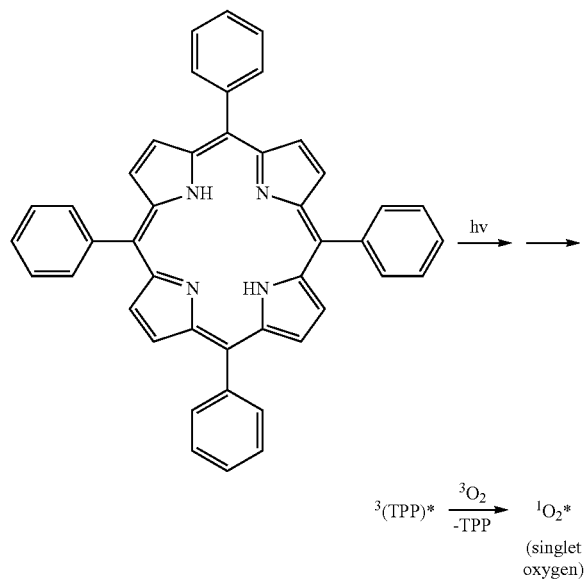

Figure 10:
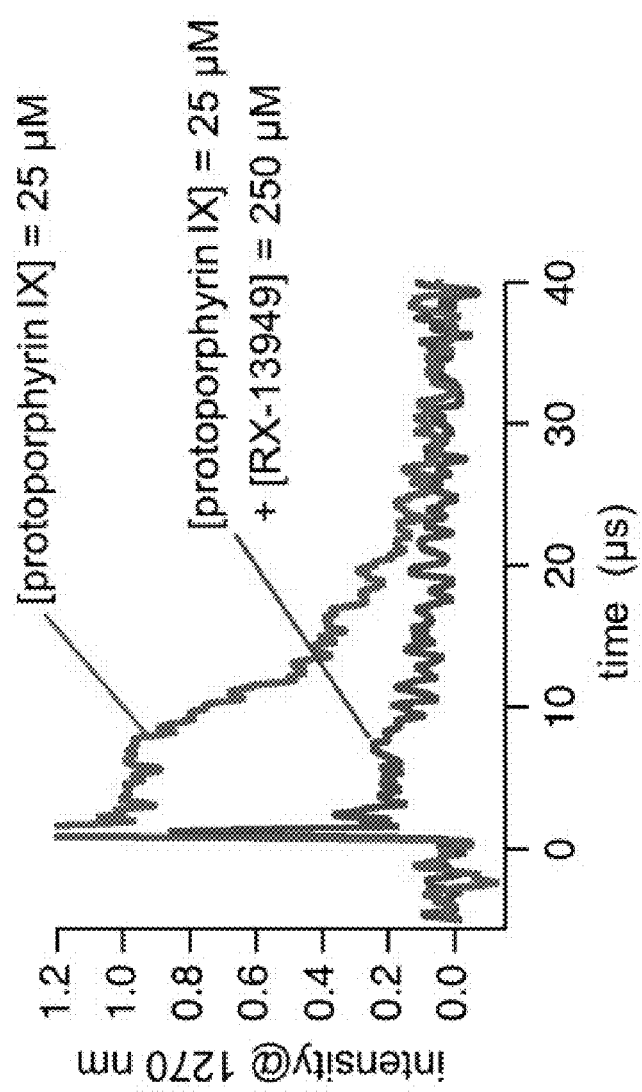
FIG. 10 illustrates singlet oxygen phosphorescence decay traces generated by pulsed laser excitation (355 nm) of protoporphyrin IX in air saturated DMSO-$d_6$ solutions in the absence and presence of the compound of Formula I(a)(1), according to a specific example embodiment of the disclosure.
Figure 11:
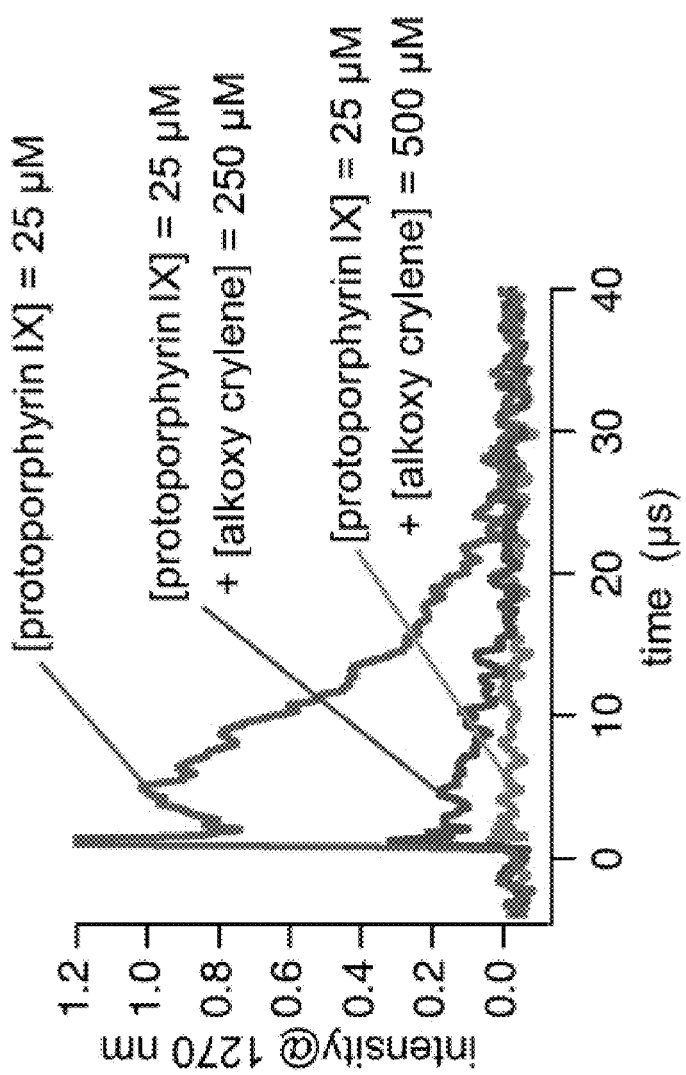
FIG. 11 illustrates singlet oxygen phosphorescence decay traces generated by pulsed laser excitation (355 nm) of protoporphyrin IX in air saturated DMSO-$d_6$ solutions in the absence and presence of the alkoxy crylene compound at different concentrations, according to a specific example embodiment of the disclosure.

Singlet oxygen was generated by pulsed laser excitation in the UV (355 nm) by protoporphyrin IX. Protoporphyrin IX was selected on the basis of its high extinction coefficient (FIG. 2). The solvent DMSO-$d_6$ was selected because of good solubility of the sensitizer and stabilizers. The deuterated form of DMSO was used because of the longer singlet oxygen lifetime in deuterated solvents compared to solvents containing hydrogen. FIG. 10 and FIG. 11 show kinetic traces of singlet oxygen phosphorescence generated from photoexcitation of protoporphyrin IX. In the presence of small amounts (250 μM) of the compound of Formula I(a)(1) (FIG. 10) or the alkoxy crylene compound (FIG. 11) significantly reduced singlet oxygen phosphorescence. However, the reduced amount of generated singlet oxygen in the presence of the alkoxy cylene compound is probably caused by competitive excitation light absorption, where most of the light is absorbed by the compound of Formula I(a)(1) or the two compounds and not by protoporphyrin IX. Excited state quenching of the protoporphyrin IX by the two compounds is unlikely to occur at these low stabilizer concentrations (μM). As shown in FIGS. 4 and 6, much higher stabilizer concentrations are needed (mM) for excited sensitizer state quenching of porphyrin compounds (sensitizers).

Figures 12A, 12B:
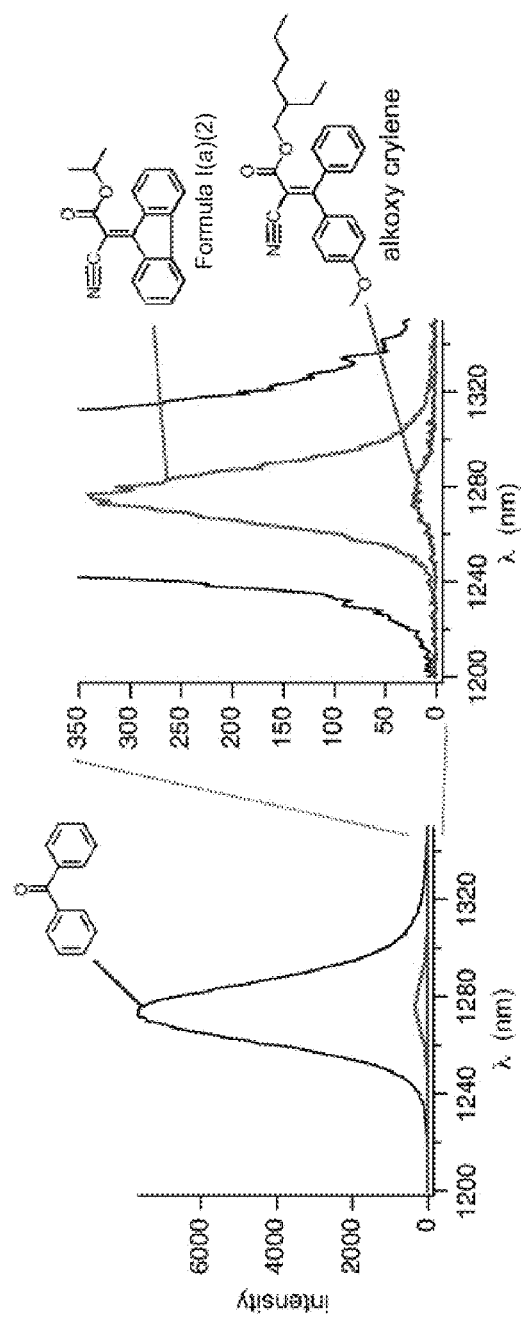
FIG. 12A illustrates singlet oxygen phosphorescence spectra generated by photoexcitation of Formula I(a)(1) and alkoxy crylene at 355 nm in benzophenone in air saturated $CCl_4$ solution.
FIG. 12B illustrates and enlargement of the lower portion of FIG. 12A.

To investigate to what extent the stabilizers can generate singlet oxygen upon direct UV photolysis, singlet oxygen phosphorescence measurements were performed under photolysis at 355 nm. For these experiments $CCl_4$ was selected as solvent, because of the long lifetime of singlet oxygen in this solvent, which makes these experiments easier to perform. Weak singlet oxygen signals were observed upon photolysis at 355 nm (FIG. 12). Using benzophenone as reference (quantum yield of singlet oxygen generation: 0.35) the low quantum yields of singlet oxygen generation were estimated: compound of Formula I(a)(1): 0.015 and alkoxy crylene: ~0.001.

Figure 13:
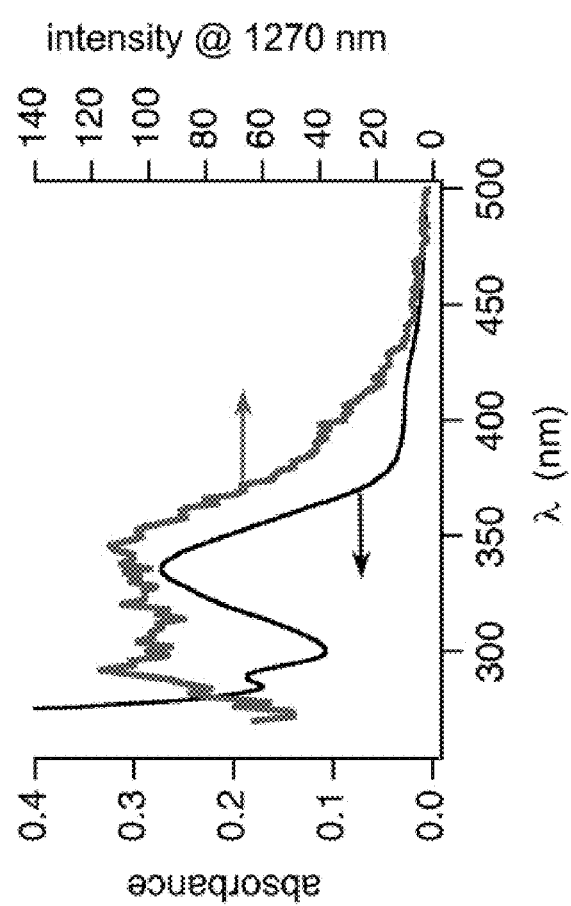
FIG. 13 illustrates an absorption spectrum and a singlet oxygen phosphorescence excitation spectrum (monitored at 1270 nm) of alkoxy crylene in air saturated $CCl_4$ solutions, according to a specific example embodiment of the disclosure.

To ensure that the observed weak singlet oxygen signals truly originated from the two compounds and not from possible impurities in the sample or solvent, singlet oxygen phosphorescence excitation spectra were recorded. Because the excitation spectrum resembles the absorption spectrum (FIG. 13), it can be concluded that the major amount of observed weak singlet oxygen phosphorescence was generated from compounds of Formula I. However, no match of the excitation spectrum with the absorption spectrum was observed for the alkoxy crylene compound, which suggests that the observed very weak singlet oxygen originated mostly from impurities.

In conclusion, the mechanism of photoprotection by compounds of Formula I and the non-fused alkoxy crylene compound is probably dominated by their strong light absorption and fast deactivation to the ground state. However, excited state quenching, as shown for protoporphyn IX with the compound of Formula I(a)(1), should provide additional photoprotection.

Example 5: Mechanisms for Resolving Excited States—Quenching

Figure 14A:
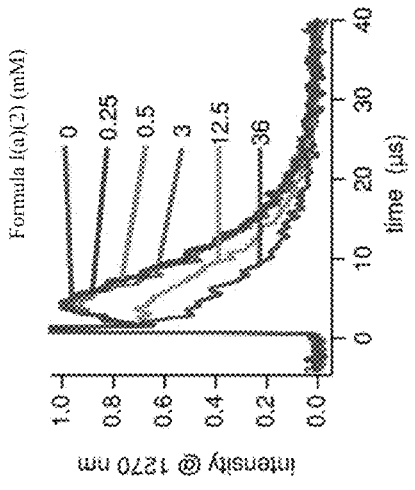
FIG. 14A illustrates singlet oxygen phosphorescence decay traces of protoporphyrin IX (25 μM) in air saturated DMSO-$d_6$ solutions in the absence and presence of the compound of Formula I(a)(1), according to a specific example embodiment of the disclosure, monitored at 1270 nm generated by pulsed laser excitation at 355 nm.
Figure 14B:
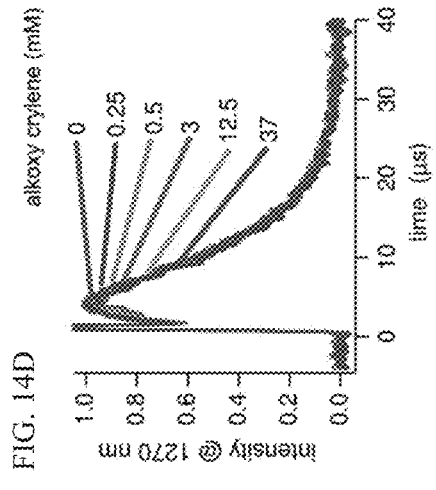
FIG. 14B illustrates singlet oxygen phosphorescence decay traces of protoporphyrin IX (25 μM) in air saturated DMSO-$d_6$ solutions in the absence and presence of the compound of Formula I(a)(1), according to a specific example embodiment of the disclosure, monitored at 1270 nm generated by pulsed laser excitation at 532 nm.
Figure 14C:
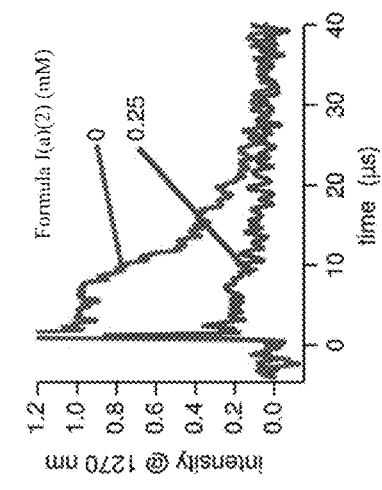
FIG. 14C illustrates singlet oxygen phosphorescence decay traces of protoporphyrin IX (25 μM) in air saturated DMSO-$d_6$ solutions in the absence and presence of an alkoxy crylene compound, according to a specific example embodiment of the disclosure, monitored at 1270 nm generated by pulsed laser excitation at 355 nm.
Figure 14D:
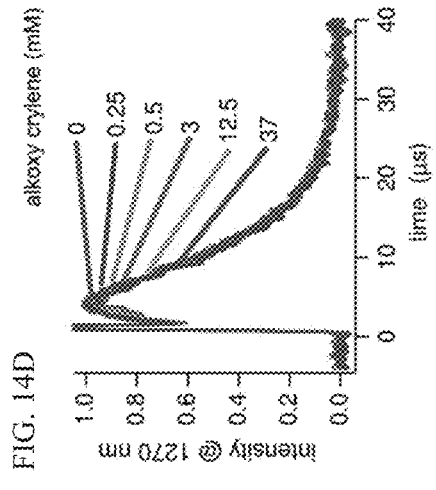
FIG. 14D illustrates singlet oxygen phosphorescence decay traces of protoporphyrin IX (25 μM) in air saturated DMSO-$d_6$ solutions in the absence and presence of an alkoxy crylene compound, according to a specific example embodiment of the disclosure, monitored at 1270 nm generated by pulsed laser excitation at 532 nm.

In the previous experiments, singlet oxygen was generated by pulsed laser excitation in the UV spectral region (355 nm) of protoporphyrory IX. The singlet oxygen generation was mostly suppressed by addition of small amounts of the compound of Formula I(a)(1) or the alkoxy crylene compound (FIG. 14A and FIG. 14C). This was explained by a simple optical screening mechanism, where the compound of Formula I(a)(1) and alkoxy crylene absorb the UV light.

In this example, laser excitation was performed with visible light at 532 nm, where the compound of Formula I(a)(1) and the alkoxy crylene compound are transparent. No suppression of singlet oxygen generation was observed by the presence of the alkoxy crylene compound even at high concentrations (37 mM) (FIG. 1D). The absence of singlet oxygen suppression with 532 nm excitation supports the optical screening mechanism with 355 nm excitation. In the presence of the compound of Formula I(a)(1) at concentrations above 3 mM the amount of generated singlet oxygen was reduced (FIG. 14B). This reduction is probably caused by protoporphyrin IX excited state quenching by the compound of Formula I(a)(1). In the previous experiments it was shown that protoporphyrin IX singlet and triplet excited states are quenched by the compound of Formula I(a)(1), but not by the alkoxy crylene compound.

The above-described experiments with protoporphyrin IX were performed in DMSO-$d_6$, a solvent with a relatively short singlet oxygen lifetime, because the polar protoporphyrin IX is not soluble enough is solvents with long singlet oxygen lifetimes, such as $CDCl_3$ and $CCl_4$. Solvents with long singlet oxygen lifetimes make singlet oxygen phosphorescence measurements significantly easier to perform. Additional experiments using the less polar dimethyl ester derivative of protoporphyrin IX were performed, which shows good solubility in $CDCl_3$. The excited state properties of protoporphyrin IX should not be affected by the methyl ester functionality.

Singlet oxygen phosphorescence experiments were performed to investigate if the large differences in triplet quenching rate constants have an impact on the observed singlet oxygen yields. The dimethyl ester derivative of PPIX (MePPIX, Formula IV(c)) was selected as sensitizer, because of better solubility in a solvent with long singlet oxygen lifetime ($CDCl_3$).

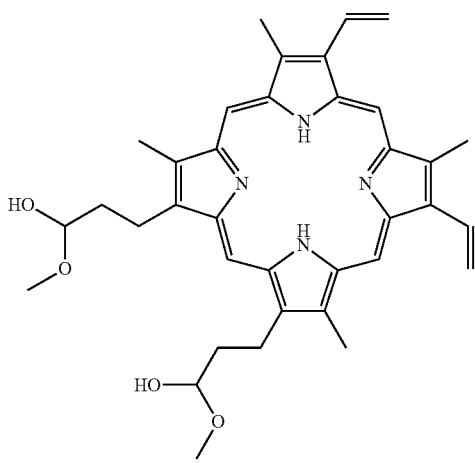

IV(c)

The excited state properties of protoporphyrin IX should not be effected by the methyl ester functionality. Air saturated $CDCl_3$ of MePPIX were excited with a pulsed Nd-YAG laser with visible light at 532 nm, where the stabilizers are mostly transparent. FIG. 15 shows the generated kinetic traces of singlet oxygen phosphorescence in the absence and presence of stabilizers. Comparison of these kinetic traces shows major differences for the different stabilizers. The non-bridged stabilizer, alkoxy crylene did not suppress singlet oxygen generation. The lack of singlet oxygen suppression is consistent with the lack of observable quenching of singlet or triplet excited states of PPIX by alkoxy crylene. The bridged stabilizers suppressed singlet oxygen generation to different degrees with II(a)(1) showing the largest suppression.

Figure 15A:
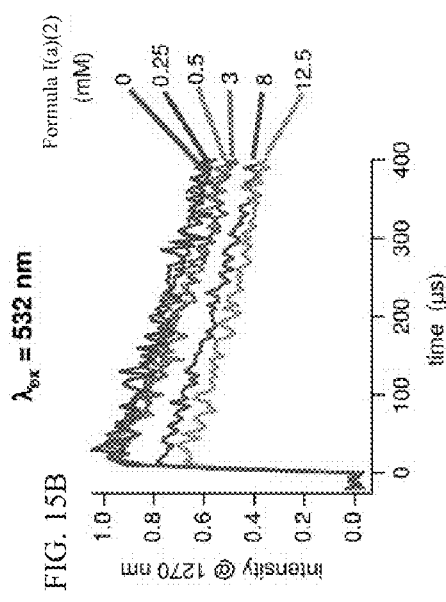
FIG. 15A illustrates singlet oxygen phosphorescence decay traces of protoporphyrin IX dimethyl ester (25 μM) in air saturated $CDCl_3$ solutions in the absence and presence of the compound of Formula I(a)(1), according to a specific example embodiment of the disclosure, monitored at 1270 nm generated by pulsed laser excitation at 355 nm.
Figure 15B:
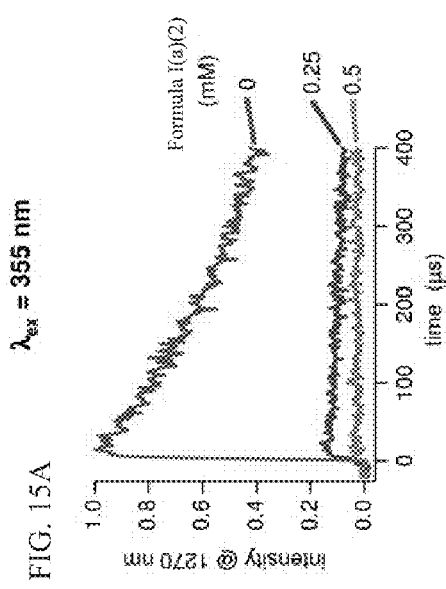
FIG. 15B illustrates singlet oxygen phosphorescence decay traces of protoporphyrin IX dimethyl ester (25 μM) in air saturated $CDCl_3$ solutions in the absence and presence of the compound of Formula I(a)(1), according to a specific example embodiment of the disclosure, monitored at 1270 nm generated by pulsed laser excitation at 532 nm.
Figure 15C:
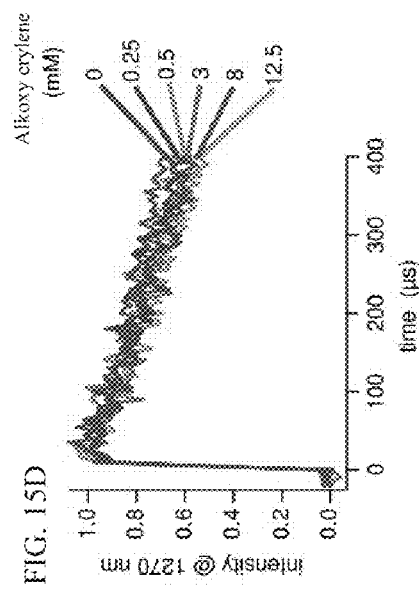
FIG. 15C illustrates singlet oxygen phosphorescence decay traces of protoporphyrin IX dimethyl ester (25 μM) in air saturated $CDCl_3$ solutions in the absence and presence of an alkoxy crylene compound, according to a specific example embodiment of the disclosure, monitored at 1270 nm generated by pulsed laser excitation at 355 nm.
Figure 15D:
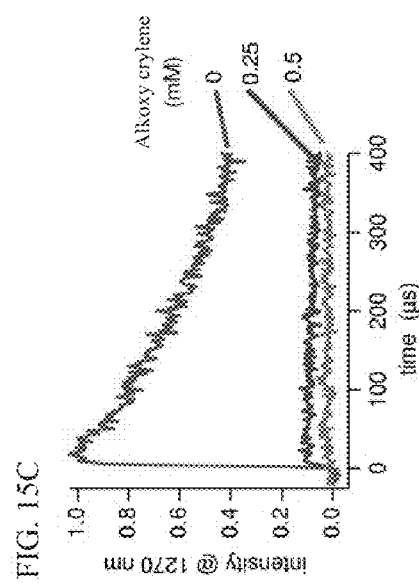
FIG. 15D illustrates singlet oxygen phosphorescence decay traces of protoporphyrin IX dimethyl ester (25 μM) in air saturated CDCl$_3$ solutions in the absence and presence of an alkoxy crylene compound, according to a specific example embodiment of the disclosure, monitored at 1270 nm generated by pulsed laser excitation at 532 nm.
Figure 15E:
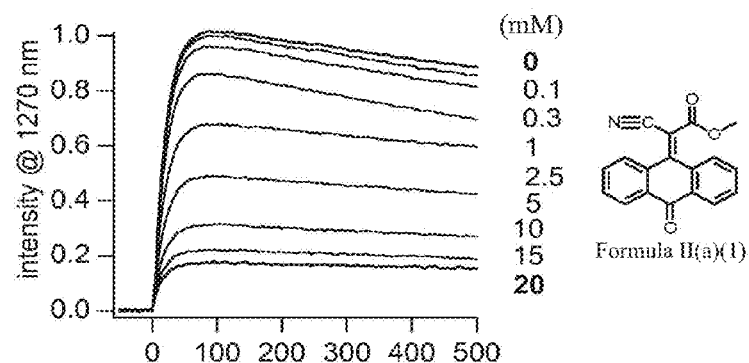
FIG. 15E illustrates singlet oxygen phosphorescence decay traces of protoporphyrin IX dimethyl ester (25 µM) in air saturated CDCl$_3$ solutions in the absence and presence of Formula II(a)(1), according to a specific example embodiment of the disclosure.
Figure 15F:
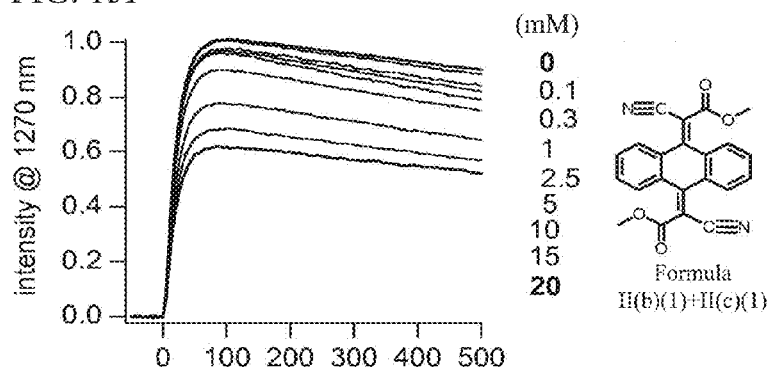
FIG. 15F illustrates singlet oxygen phosphorescence decay traces of protoporphyrin IX dimethyl ester (25 µM) in air saturated CDCl$_3$ solutions in the absence and presence of Formula II(b)(1) and II(c)(1), according to a specific example embodiment of the disclosure.
Figure 15G:
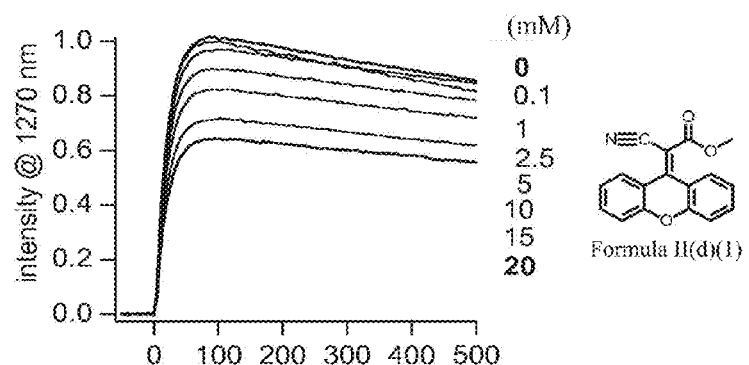
FIG. 15G illustrates singlet oxygen phosphorescence decay traces of protoporphyrin IX dimethyl ester (25 µM) in air saturated CDCl$_3$ solutions in the absence and presence of Formula II(d)(1), according to a specific example embodiment of the disclosure.
Figure 15H:
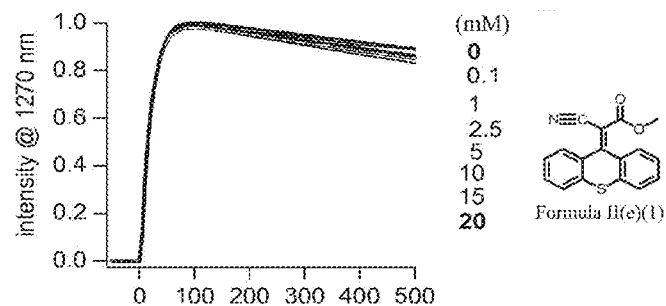
FIG. 15H illustrates singlet oxygen phosphorescence decay traces of protoporphyrin IX dimethyl ester (25 µM) in air saturated CDCl$_3$ solutions in the absence and presence of Formula II(e)(1), according to a specific example embodiment of the disclosure.
Figure 15I:
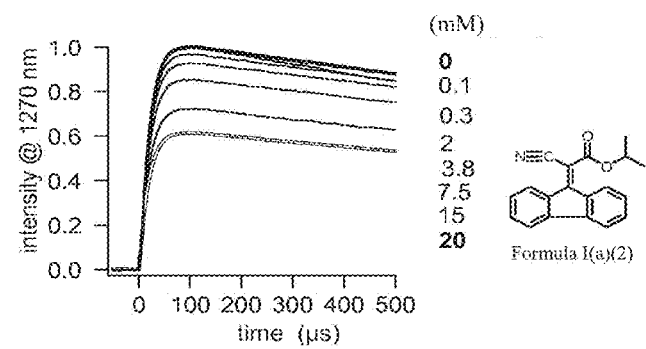
FIG. 15I illustrates singlet oxygen phosphorescence decay traces of protoporphyrin IX dimethyl ester (25 µM) in air saturated CDCl$_3$ solutions in the absence and presence of Formula II(a)(1), according to a specific example embodiment of the disclosure.
Figure 15J:
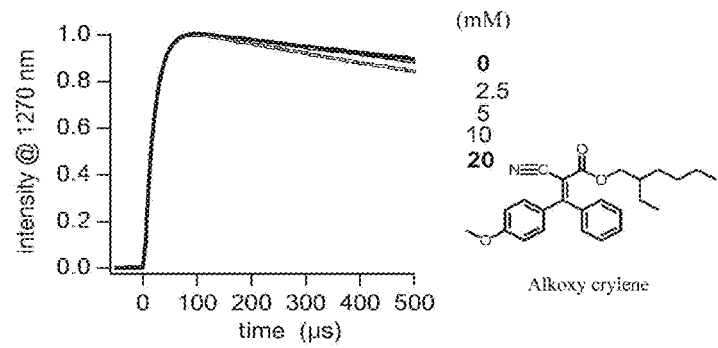
FIG. 15J illustrates singlet oxygen phosphorescence decay traces of protoporphyrin IX dimethyl ester (25 µM) in air saturated CDCl$_3$ solutions in the absence and presence of alkoxy crylene, according to a specific example embodiment of the disclosure.

The singlet oxygen phosphorescence experiments shown in FIG. 3 using the dimethyl ester derivative of protoporphyrin IX in $CDCl_3$ are qualitatively similar to those shown in FIG. 14 using protopophyrin IX in DMSO-$d_6$. Although singlet oxygen phosphorescence detection was easier in $CDCl_3$, decomposition of protoporphyrin IX dimethyl ester by singlet oxygen caused a larger error in phosphorescence intensity, which was especially visible in FIG. 15D compared to FIG. 14D. The longer singlet oxygen lifetime in $CDCl_3$ makes the chromophore more sensitive to oxidative damage.

Figure 16A:
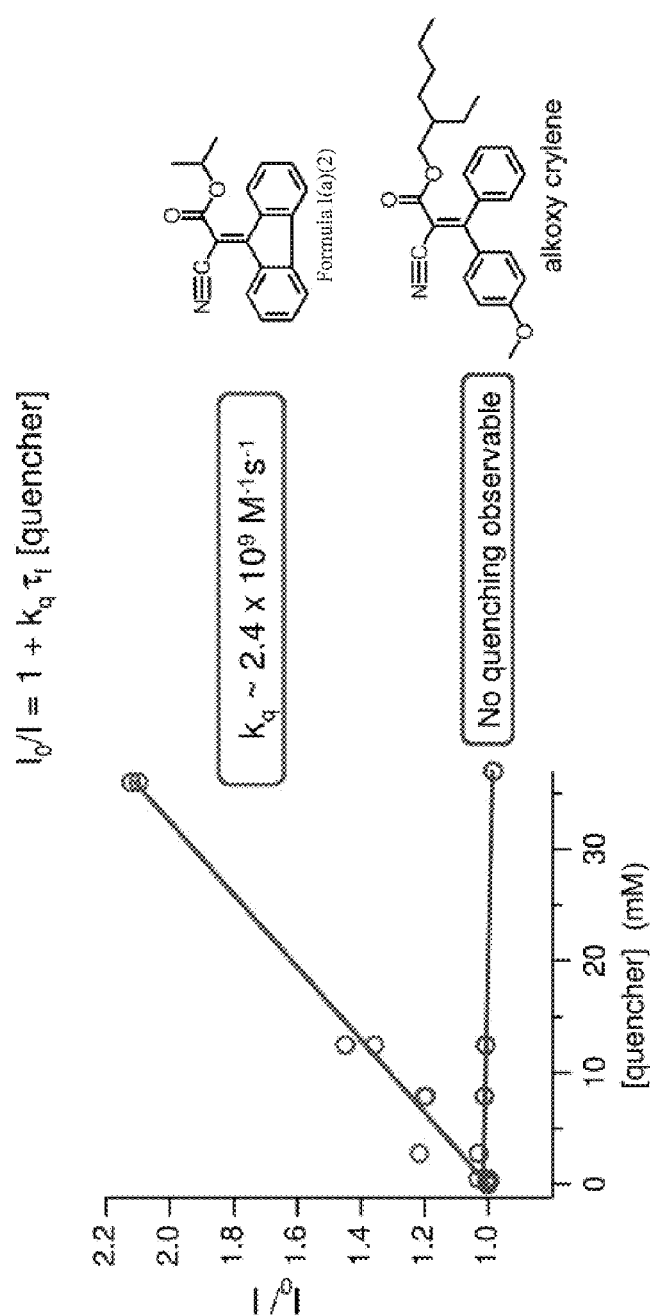
FIG. 16A illustrates a Stern-Volmer plot of singlet oxygen phosphorescence data from decay traces of protoporphyrin IX (25 µM) in air saturated DMSO-d$_6$ solutions in the absence and presence of the compound of Formula I (a)(1) and alkoxy crylene, according to a specific example embodiment of the disclosure, monitored at 1270 nm generated by pulsed laser excitation at 355 nm.
Figures 16B, 16C:
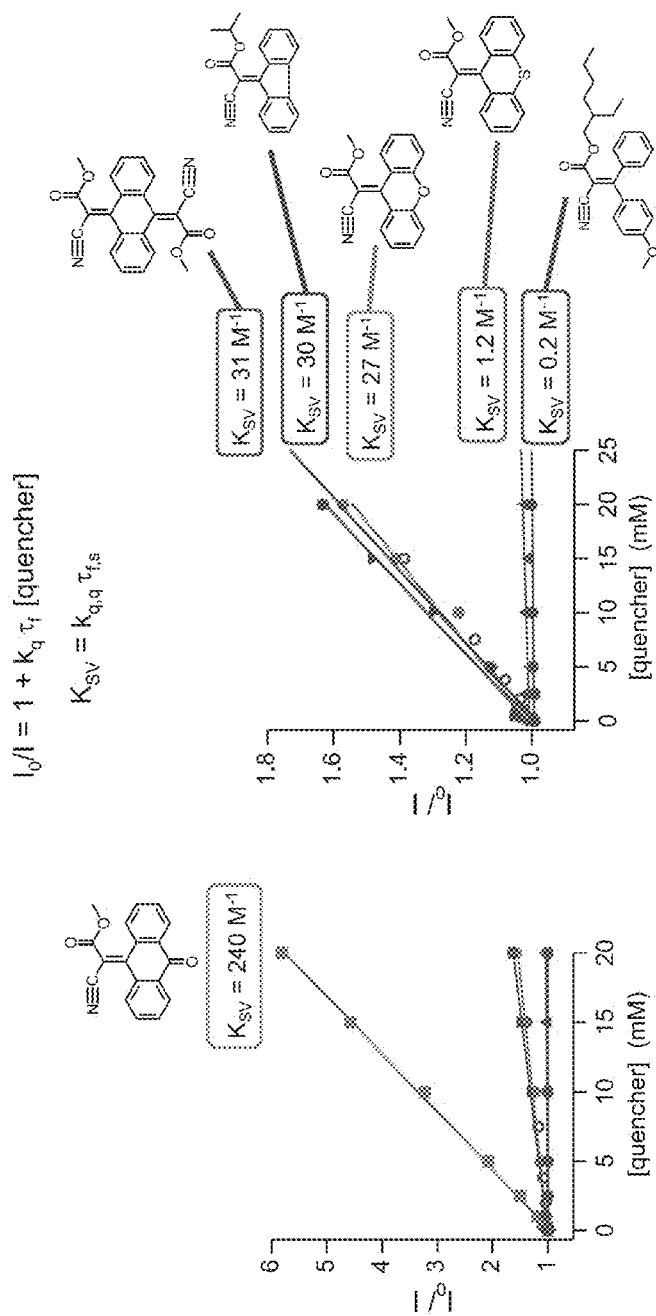
FIG. 16B illustrates a Stern-Volmer plot of singlet oxygen phosphorescence data from decay traces of protoporphyrin IX (25 µM) in air saturated DMSO-d$_6$ solutions in the absence and presence of the compound of Formula II(a)(1), according to a specific example embodiment of the disclosure, monitored at 1270 nm generated by pulsed laser excitation at 532 nm.
FIG. 16C illustrates a Stern-Volmer plot of singlet oxygen phosphorescence data from decay traces of protoporphyrin IX (25 µM) in air saturated DMSO-d$_6$ solutions in the absence and presence of the compound of Formula I(a)(1), II(b)(1), II(d)(1), II(e)(1), and alkoxy crylene, according to a specific example embodiment of the disclosure, monitored at 1270 nm generated by pulsed laser excitation at 355 nm.
Figure 17:
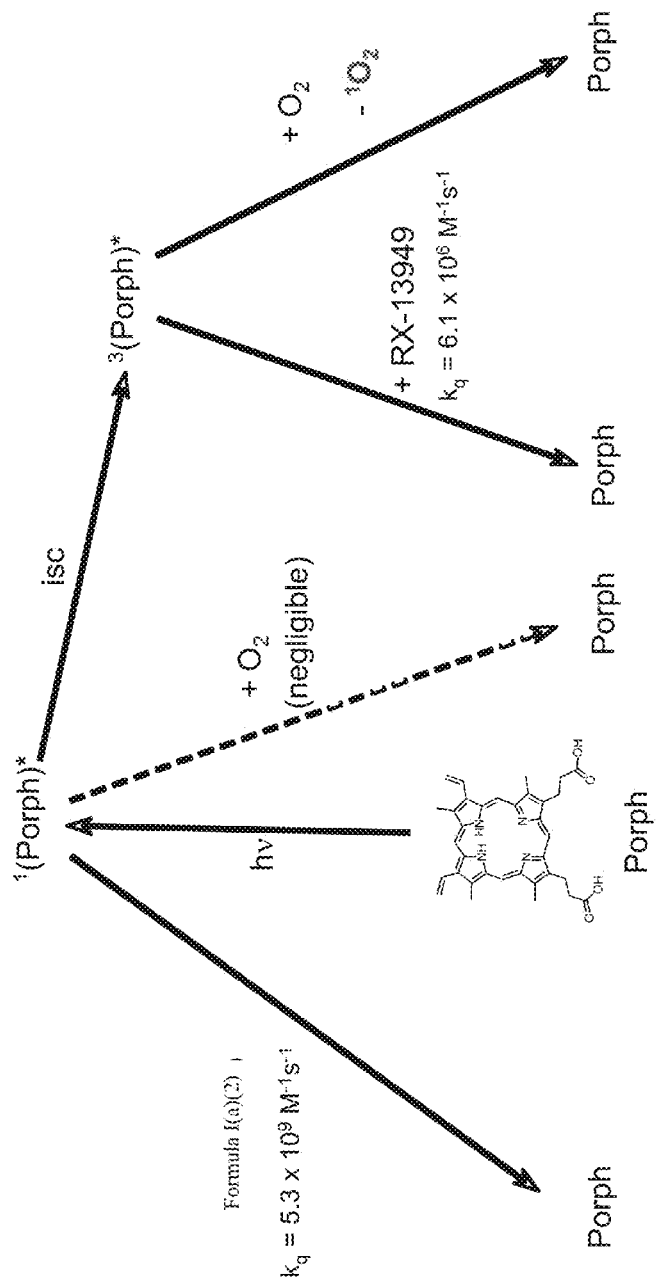
FIG. 17 illustrates a scheme of quenching mechanisms of protoporphyrin IX excited states, according to a specific example embodiment of the disclosure.

To demonstrate that the suppression of singlet oxygen generation from photoexcitation at 532 nm is caused by singlet excited state quenching of protoporphyrin IX by compounds of Formulas I, II, and III, Stern-Volmer analysis of the data in FIG. 14B and FIG. 15 was performed. The singlet oxygen phosphorescence intensity in the absence of the compound of Formulas I(a)(1), II(a)(1), II(d)(1), II(e)(1), or a mixture of II(b)(1) and II(c)(1) ($I_0$) divided by the singlet oxygen phosphorescence intensity in the presence of compounds of Formula I/II(I) was plotted against the Formula I/II concentration (FIG. 16). From the slope of these plots (Stern-Volmer constant) and the lifetime of the quenched excited state, the bimolecular quenching constant can be extracted. If the excited state, which is quenched by the compound of Formula I(a)(1) (which causes a reduction in singlet oxygen production) is the singlet excited state of protoporphyrin IX then, using the previously measured fluorescence lifetime in acetonitrile ($\tau f=12.7$ ns) a quenching rate constant of $2.4\times10^9$ $M^{-1}$ $s^{-1}$ is estimated. This rate constant is in the same order of the previously measured rate constant using fluorescence quenching ($5.3\times10^9$ $M^{-1}$ $s^{-1}$) which indicates that singlet excited state quenching of protoporphyrin by the compound of Formula I(a)(1) is predominantly causing the suppression of singlet oxygen generation. The rate constant derived from singlet oxygen phosphorescence quenching (FIG. 16) is only half of the more directly derived rate constant from fluorescence quenching, which could be caused by the difference in solvents or by some contribution of protoporphyrin triplet quenching by the compound of Formula I(a)(1). If the suppression of singlet oxygen generation would be entirely caused by triplet protoporphyrin IX quenching by the compound of Formula I(a)(1), the rate constant from the Stern-Volmer plot (FIG. 4) would be $\sim3\times10^7$ $M^{-1}$ $s^{-1}$ considering a protoporphyrin IX triplet lifetime of $\sim1$ μs in air saturated DMSO. This rate constant is 5 times higher than the directly measured rate constant by laser flash photolysis ($6.1\times10^6$ $M^{-1}$ $s^{-1}$). This suggests that protoporphyrin IX triplet quenching by compounds of Formulas I, II, and III makes only a minor contribution to the suppression of singlet oxygen generation under these conditions. It must be noted that protoporphyrin IX triplet lifetime of $\sim1$ μs in air saturated DMSO was only estimated based on the directly measured triplet lifetime in air saturated acetonitrile and considering the different oxygen concentration in DMSO compared to acetonitrile. If necessary, the protoporphyrin IX triplet lifetime in air saturated DMSO can easily be measured by laser flash photolysis. The complex reaction mechanism is summarized in Scheme 1 (FIG. 17).

Additional cyano-containing fused tricyclic compounds having Formulas I(a)(1), II(a)(1), II(b)(1), II(c)(1), and II(d)(1) were tested against the alkoxy crylene compound as shown in FIG. 18.

The redox potential of protoporphyrin IX, Formulas I(a)(1), II(a)(1), II(b)(1), II(d)(1), II(e)(1), and alkoxy crylene were determined with respect to a Ag/AgCl reference electrode. For these experiments, dimethylsulfoxide (DMSO) and tetrabutylammonium perchlorate (TBAP) were obtained from Sigma Aldrich and used as received. Acetone was obtained from Fisher Scientific. Solutions of 0.01 M (10 mM) of protoporphyrin IX, Formulas I(a)(1), II(a)(1), II(b)(1), II(d)(1), II(e)(1), and alkoxy crylene were prepared by dissolving measured amounts in a supporting electrolyte of 0.1 M TBAP in DMSO; the total volume of each sample solution was 15 mL. Platinum wires (BASi MW-1032) of diameter 0.5 mm were employed for both the working electrode (WE) and counter electrode (CE). A dry-solvent tolerant Ag/AgCl reference electrode (RE) was obtained from eDAQ (Model ET072). The WE and CE were cleaned prior to each by first rinsing in acetone, then DI, followed by soaking in ~50% aqueous $H_2SO_4$ for 10-20 minutes and then a final DI rinse. The RE electrode was cleaned prior to each use by an acetone rinse followed by DI rinse. Each sample solution was prepared in a fresh glass vial which had been rinsed with DI then acetone and allowed to dry Immediately after preparing each solution, it was purged with pure $N_2$ gas for 15-20 minutes with the electrodes in place. Voltammetry data was collected shortly afterwards with an EG&G PAR 263 A Potentiostant/Galvanostat operated using a Labview-based control program. Scans were performed at various potential ranges between +2.0V and −2.0V (vs Ag/AgCl); all scan rates were constant at 200 mV/s.

The voltammograms for protoporphyrin IX appear to show the presence of two distinct redox couples (FIG. 18A). The first redox couple (red curve) has a large reduction peak at −1255 mV and a smaller oxidation peak at −610 mV (two much smaller oxidation peaks are present at −202 mV and +164 mV which may also be associated with this couple); the redox potential for this couple is thus estimated as −932 mV. The second redox couple has a reduction peak near −1741 mV and an oxidation peak near −1152 mV; this yields a redox potential of approximately −1446 mV.

The voltammograms for Formula I(a)(1) also show the presence of two distinct redox couples (FIG. 18B). The first redox couple (red curve) has a reduction peak at −757 mV and an oxidation peak at −560 mV; the redox potential for this couple is thus estimated as −658 mV. The second redox couple has a reduction peak at −1297 mV and an oxidation peak at −1102 mV; the redox potential is approximately −1199 mV.

The voltammograms for Formula II(a)(1) show the presence of two distinct redox couples (FIG. 18C). The first redox couple (red curve) has a reduction peak at −864 mV and an oxidation peak at −706 mV; the redox potential for this couple is thus estimated as −785 mV. The second redox couple has a reduction peak at −1537 mV and oxidation peaks at −1466 mV (small) and +430 mV (large); the redox potential is estimated as −1501 mV.

The voltammograms for Formula II(e)(1) show the presence of two distinct redox couples (FIG. 18D). The first redox couple (red curve) has a reduction peak at −969 mV and an oxidation peak at −782 mV; the redox potential for this couple is thus estimated as −875 mV. The second redox couple has a reduction peak at −1409 mV and oxidation peaks at −1286 mV (small) and +434 mV (large); the redox potential is estimated as −1347 mV.

The voltammogram for Formula II(a)(1) shows the presence of only one distinct redox couple (FIG. 18E). This couple has a reduction peak at −656 mV and an oxidation peak at −300 mV; the redox potential is thus estimated as −493 mV.

The voltammogram for Formula II(b)(1) also shows the presence of only one distinct redox couple (FIG. 18F). This couple has a reduction peak at −545 mV and an oxidation peak at +54 mV; the redox potential for this couple is thus estimated as −245 mV.

The voltammograms for alkoxy crylene show the presence of two distinct redox couples. The first redox couple (red curve) has a reduction peak at −1183 mV and an oxidation peak at −1038 mV; the redox potential for this couple is thus estimated as −1110 mV. The second redox couple has a reduction peak at −1751 mV and an oxidation peak at +318 mV; the redox potential is estimated as −694 mV.

Example 6: Stabilization of Avobenzone Compositions

Figure 19:
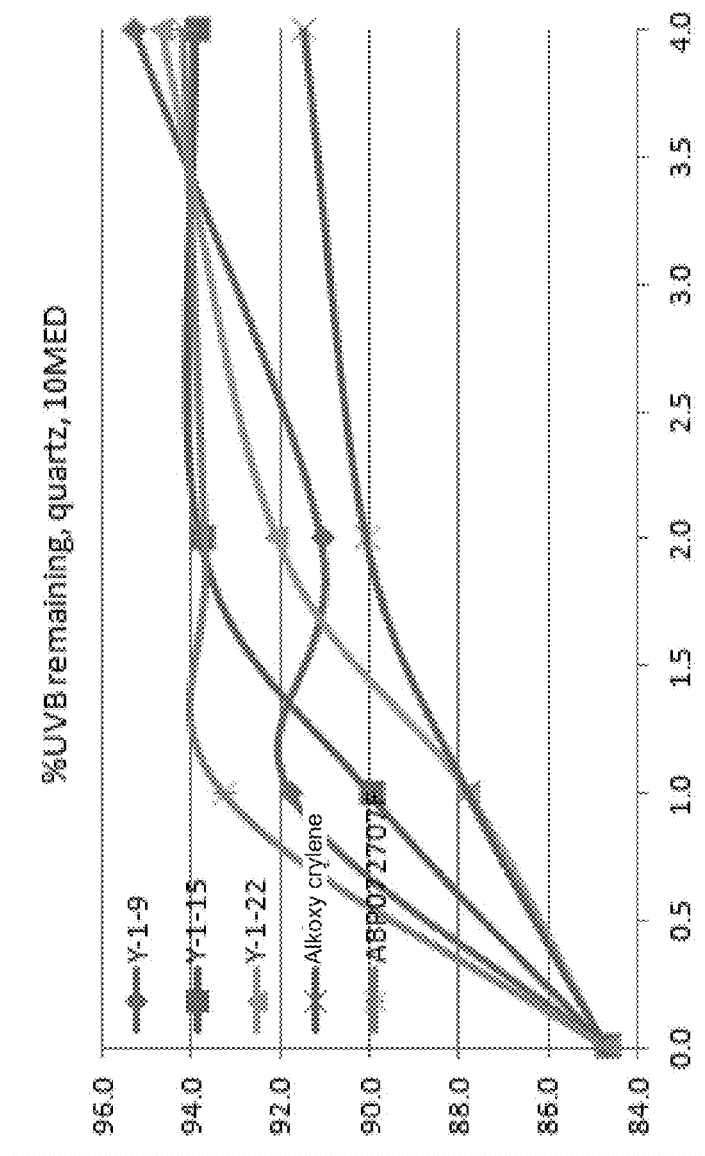
FIG. 19 illustrates a comparison of the ability of a conjugated fused polycyclic compound, according to a specific example embodiment of the disclosure, and ethylhexyl methoxycrylene to photostabilize solutions comprising Avobenzone.

Experiments were performed to assess the capacity of conjugated fused polycyclic molecules to photostabilize Avobenzone and the combination of oxymethoxy cinnamate (OMC) and Avobenzone relative to ethylhexyl methoxycrylene. Example 6 compares cyano-containing fused tricyclic compounds at 3% (w/w) to photostabilize 3% Avobenzone, except for A6, which brings Y-1-22 up to the same molar concentration as the others when they're at 3%. The results as shown in Table 1 are graphically in FIG. 19.

TABLE 1

Experiment 6-1, 20 uls solution on quartz

| Sample ID | A1 | A2 | A3 | A4 | A5 | A6 | A7 |
|---|---|---|---|---|---|---|---|
| Ethylhexyl cyano xanthenylidene acetate (Y-1-9) | 0.30 | | | | | | |
| Ethylhexyl cyano thioxanthenylidene acetate (Y-1-15) | | 0.30 | | | | | |
| Ethylhexyl dimethyl 2,2'-anthracene-9,10-diylidenebis (cyanoacetate) (Y-1-22) | | | 0.30 | | 0.45 | | |
| Ethylhexyl methoxycrylene | | | | 0.30 | | | |
| ABP072707F (a methoxy crylene) | | | | | | | 0.30 |
| Avobenzone | 0.30 | 0.30 | 0.30 | 0.30 | 0.30 | 0.30 | 0.30 |
| PA 18 | 0.20 | 0.20 | 0.20 | 0.20 | 0.20 | 0.20 | 0.20 |
| C12-C15 alkyl benzoate | 2.00 | 1.70 | 1.70 | 1.70 | 1.70 | 1.55 | 1.70 |
| Ethyl acetate | 7.50 | 7.50 | 7.50 | 7.50 | 7.50 | 7.50 | 7.50 |
| Total | 10.00 | 10.00 | 10.00 | 10.00 | 10.00 | 10.00 | 10.00 |
| % UVB remaining, quartz, 10med | 71.1 | 99.0 | 99.8 | 97.3 | 96.7 | 99.0 | 92.9 |
| % UVB remaining, quartz, 10med | 26.2 | 95.9 | 94.7 | 91.6 | 97.3 | 96.7 | 94.6 |

Figure 20:
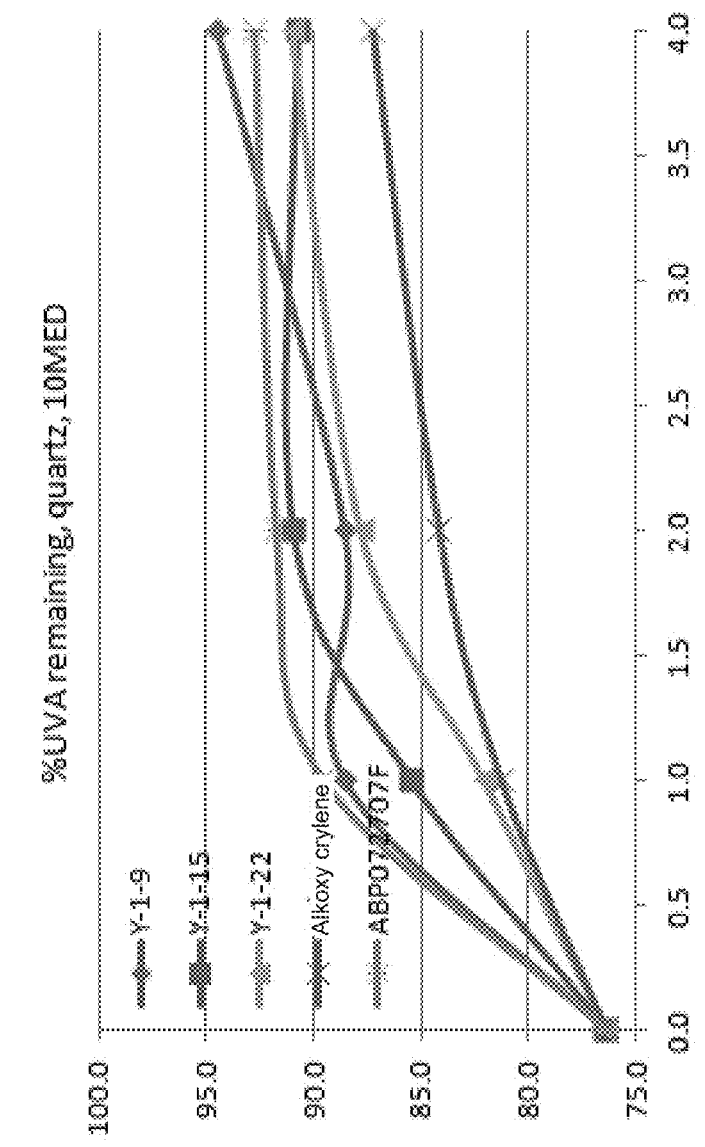
FIG. 20 illustrates a comparison of the ability of a conjugated fused polycyclic compound, according to a specific example embodiment of the disclosure, and ethylhexyl methoxycrylene to photostabilize solutions comprising Avobenzone and octylmethoxy cinnamate.

Experiment 6-2 compares the compounds at 3% to photostabilize Avobenzone at 3% and OMC at 7.5%. The results are shown in Table 2 and graphically in FIG. 20.

TABLE 2

Experiment 6-1, 20 uls solution on quartz

| | Y-1-9 | Y-1-15 | Y-1-22 | SolaStay S1 | ABP072707F |
|---|---|---|---|---|---|
| % UVB | | | | | |
| 0.0 | 84.7 | 84.7 | 84.7 | 84.7 | 84.7 |
| 1.0 | 91.8 | 90.0 | 87.8 | 87.8 | 93.3 |
| 2.0 | 91.1 | 93.8 | 92.1 | 90.1 | 93.7 |
| 4.0 | 95.3 | 93.9 | 94.7 | 91.5 | 94.2 |
| % UVA | | | | | |
| 0.0 | 76.4 | 76.4 | 76.4 | 76.4 | 76.4 |
| 1.0 | 88.6 | 85.5 | 82.1 | 81.3 | 89.6 |
| 2.0 | 88.6 | 91.0 | 87.8 | 84.2 | 91.8 |
| 4.0 | 94.5 | 90.8 | 91.0 | 87.3 | 92.8 |

*SolaStay S1 - ethylhexyl methoxycrylene

Example 7: Synthesis of Compound II(d)(1)

A conjugated fused tricyclic molecule according to Formula II(d)(1) may be synthesized as follows:

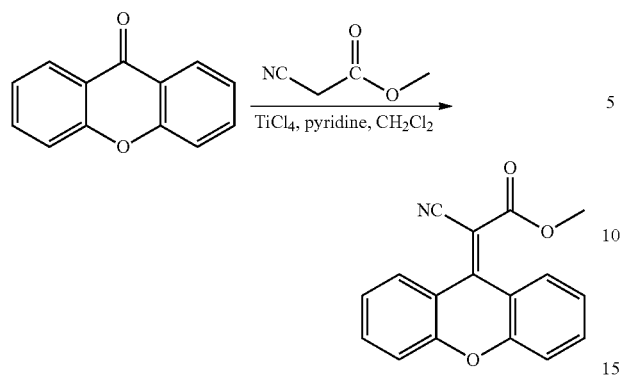

Xanthone (180 g, 0.9 mol) and methyl cyanoacetate (81 g, 1.0 equiv.) were dissolved in $CH_2Cl_2$ (2500 mL). $TiCl_4$ (180 mL) was first added dropwise to the mixture while stirring, after the dripping, pyridine (120 mL) and $CH_2Cl_2$ (130 mL) were added dropwise slowly over a period of 30 minutes with a gentle reflux, then the mixture was heated and stirred under refluxing for 8 h. And then another 0.5 equiv. methyl cyanoacetate (54 g) was added to the mixture, another $TiCl_4$ (120 mL) and pyridine (100 mL) were added in turn, then the mixture was stirred under refluxing (Monitored by TLC).

Then the mixture was treated with hydrochloric acid (10%, 1200 mL) and stirred sufficiently to transparent liquid. And then separated the oil phase, extracted the aqueous phase with $CH_2Cl_2$ (200 mL*3), combined organic phase.

The pure product was precipitated in 1500 mL methanol. The yield of the final product was 85%.

Example 8: Synthesis of Compound II(e)(1)

A conjugated fused tricyclic molecule according to Formula II(e)(1) may be synthesized as follows:

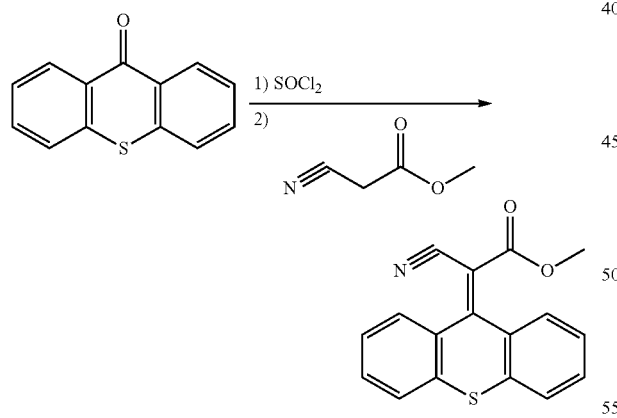

Thioxanthen-9-one (53 g) was refluxed with $SOCl_2$ (250 mL), and then the excess $SOCl_2$ was distilled. Excess methyl cyanoacetate (75 mL) was added to the mixture. Then the mixture was stirred at 120° C. for 6 h. The crude product was purified by the column chromatography. The yield of the final product was 60%.

Example 9: Synthesis of Compound II(a)(1)

A conjugated fused tricyclic molecule according to Formula II(a)(1) may be synthesized as follows:

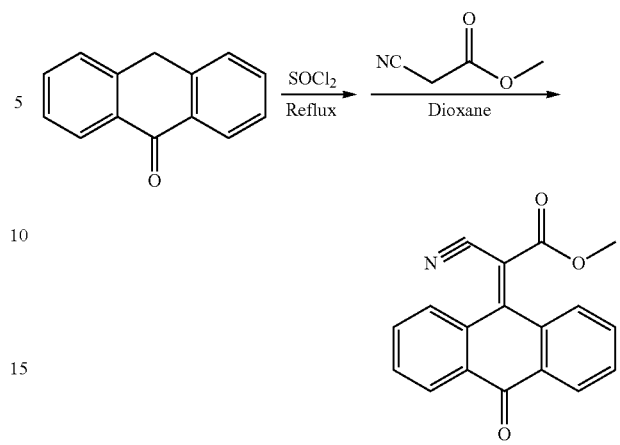

A mixture of 160 g (0.80 mol) anthrone and 500 mL of thionyl chloride was refluxed for 4 h, and then the excess $SOCl_2$ was distilled completely under reduced pressure. A solution of 180 g of methyl cyanoacetate in 100 mL of dioxane was added timely. The solution was refluxed for an additional 3 h and then cooled to 85° C., 800 mL of methanol was added to the solution and stirred to room temperature. The brown solid was filtered and washed with methanol (300 mL). The crude product was purified by active carbon decoloring in ethyl acetate. The yield of the final product was 61%.

Example 10: Synthesis of Compounds II(b)(1) and II(c)(1)

Conjugated fused tricyclic molecules according to Formula II(b)(1) and Formula II(c)(1) may be synthesized as follows:

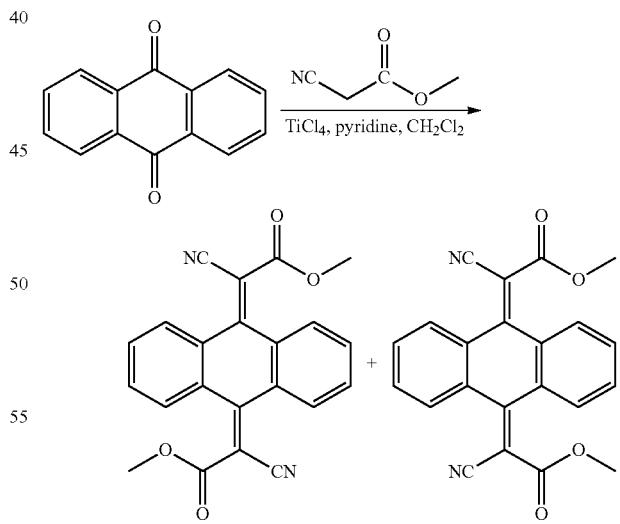

Anthraquinone (260.8 g, 1.256 mol) and methyl cyanoacetate (320 g, 3.232 mol, 2.57 equiv.) were dissolved in $CH_2Cl_2$ (3000 mL). $TiCl_4$ (400 mL) was first added at room temperature, then a solution of pyridine (240 mL) in $CH_2Cl_2$ (400 mL) were added slowly over a period of 1 h, the dropwise process without additional cooling measure and brought to a gentle reflux in the later stage. Then the mixture was heated and stirred at reflux for 2 h. Another 200 mL TiCl$_4$ and 120 mL pyridine were added to the mixture in turn. Then the mixture was stirred under refluxing (Monitored by TLC).

Then the mixture was treated with hydrochloric acid (10%, 2000 mL) and stirred sufficiently to transparent liquid. And then separated the oil phase, extracted the aqueous phase with CH$_2$Cl$_2$ (200 mL*3), combined organic phase.

The pure product was precipitated in 1500 mL methanol. The yield of the final product was 95%.

Example 11: Synthesis of Compounds II(bg)(1) and II(bj)(1)

Conjugated fused tricyclic molecules according to Formula II(bg)(1) and Formula II(bj)(1) may be synthesized as follows:

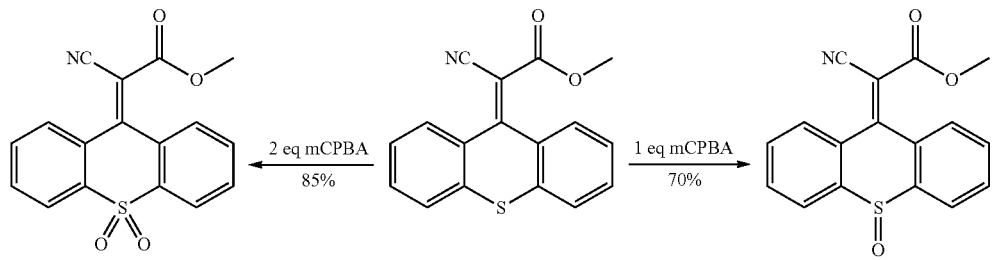 [SMILES: COC(=O)C(C#N)=C1c2ccccc2S(=O)(=O)c2ccccc21 ; COC(=O)C(C#N)=C1c2ccccc2Sc2ccccc21 ; COC(=O)C(C#N)=C1c2ccccc2S(=O)c2ccccc21]

Synthesis of Sulfoxide (II(bj)(1)

To a solution of Compound II(e)(1) in dichloromethane (0.7 M) at 0° C. was added meta-chloroperoxybenzoic acid (1.0 equivalent) and the mixture was stirred for 30 min. The reaction mixture was washed with a saturated aqueous solution of sodium bicarbonate and then extracted with dichloromethane. The organic layers were combined, dried over anhydrous magnesium sulfate, filtered, and concentrated under vacuum. Purification by column chromatography (Hexanes/Ethyl acetate) gave a white solid. Yield: 70%.

Synthesis of Sulfone (II(bg)(1)

To a solution of Formula II(e)(1) in dichloromethane (0.7 M) at 0° C. was added meta-chloroperoxybenzoic acid (2.0 equivalents). The solution was stirred at 0° C. for 30 min and then room temperature for 12 h. The reaction mixture was washed with a saturated aqueous solution of sodium bicarbonate and then extracted with dichloromethane. The organic layers were combined, dried over anhydrous magnesium sulfate, filtered, and concentrated under vacuum. Purification by recrystallization (dichloromethane) gave a white solid. Yield: 85%.

Example 12: Synthesis of Compounds I(b)(1)

A conjugated fused tricyclic molecule according to Formula I(b)(1) may be synthesized as follows:

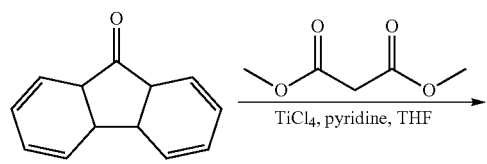

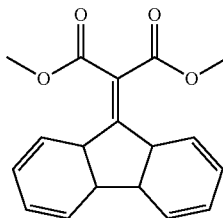

TiCl$_4$ (50 mL) in CCl$_4$ (100 mL) was added dropwise to the anhydrous THF (800 mL) in ice bath (<5° C.). The addition needed 0.5 h. Then fluorenone (36 g, 0.2 mol) and dimethyl malonate (40 g, 0.3 mol) was added to the reaction mixture quickly and then stirred for 1 h (<5° C.). Then pyridine (64 mL) in anhydrous THF (150 mL) was added slowly to the mixture for 1 h. The mixture was removed from the ice bath and refluxed for 6 h. The progress of the reaction was monitored by TLC. Then the mixture was treated with ice water (1 L) and extracted with EtOAc. The crude product was purified by recrystallization with ethanol (300 mL). The yield of the final product was 75%.

A conjugated fused tricyclic molecule according to Formula I(b)(2) may be synthesized as follows:

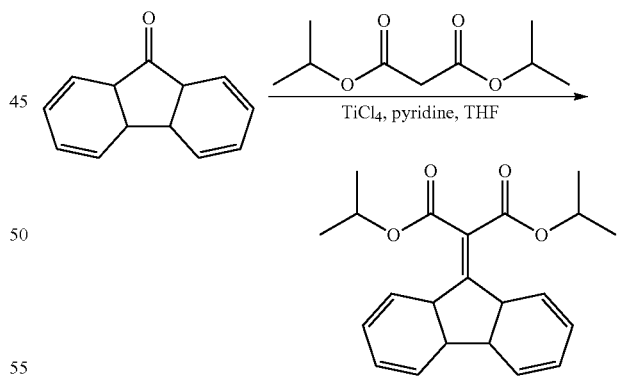

TiCl$_4$ (60 mL) in CCl$_4$ (100 mL) was added dropwise to the anhydrous THF (1.3 L) in ice bath (<5° C.). The addition needed 0.5 h. Then fluorenone (36 g, 0.2 mol) and diisopropyl malonate (56.4 g, 0.3 mol) was added to the reaction mixture quickly and then stirred for 1 h (<5° C.). Then pyridine (50 mL) in anhydrous THF (250 mL) was added slowly to the mixture for 1 h. The mixture was removed from the ice bath and refluxed for 6 h. The progress of the reaction was monitored by TLC. Then the mixture was treated with ice water (1 L) and extracted with EtOAc. The crude product was purified by recrystallization with ethanol (250 mL). The yield of the final product was 76%.

Example 13: Synthesis of Compound II(bl)(1)

A conjugated fused tricyclic molecule according to Formula II(bl)(1) may be synthesized as follows:

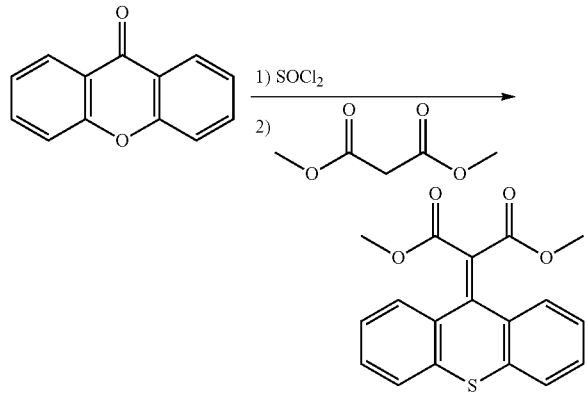

Xanthone (49 g, 0.25 mol) was refluxed with SOCl$_2$ (250 mL), and then the excess SOCl$_2$ was distilled. Excess dimethyl malonate (99 g, 0.75 mol) was added to the mixture. Then the mixture was stirred at 120° C. for 1 h. The reaction mixture was cooled and added to 1 M NaOH (600 mL) ice water. The red solid was filtered and washed with water. The crude product was purified by recrystallization with methanol (250 mL). The yield of the final product was 56%.

A conjugated fused tricyclic molecule according to Formula II(f)(2) may be synthesized as follows:

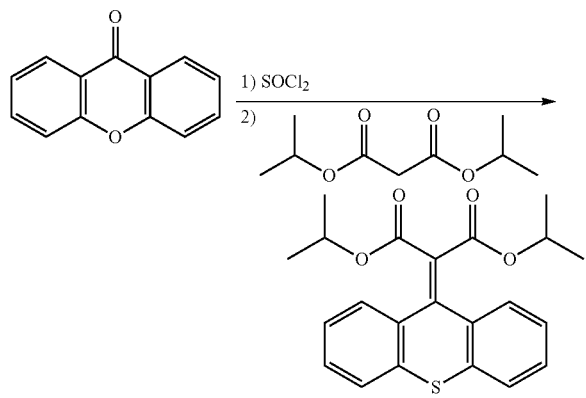

Xanthone (49 g, 0.25 mol) and DMF (1.5 mL) was refluxed with SOCl$_2$ (250 mL), and then the excess SOCl$_2$ was distilled. Excess diisopropyl malonate (70 mL, 0.37 mol) was added to the mixture. Then the mixture was stirred at 120° C. for 1 h. The reaction mixture was cooled and added to 1 M NaOH (200 mL) ice water. The red solid was filtered and washed with water. The crude product was purified by recrystallization with ethanol (200 mL). The yield of the final product was 70%.

Example 14: Performance Testing Compound II(a)(1)

Figure 21:
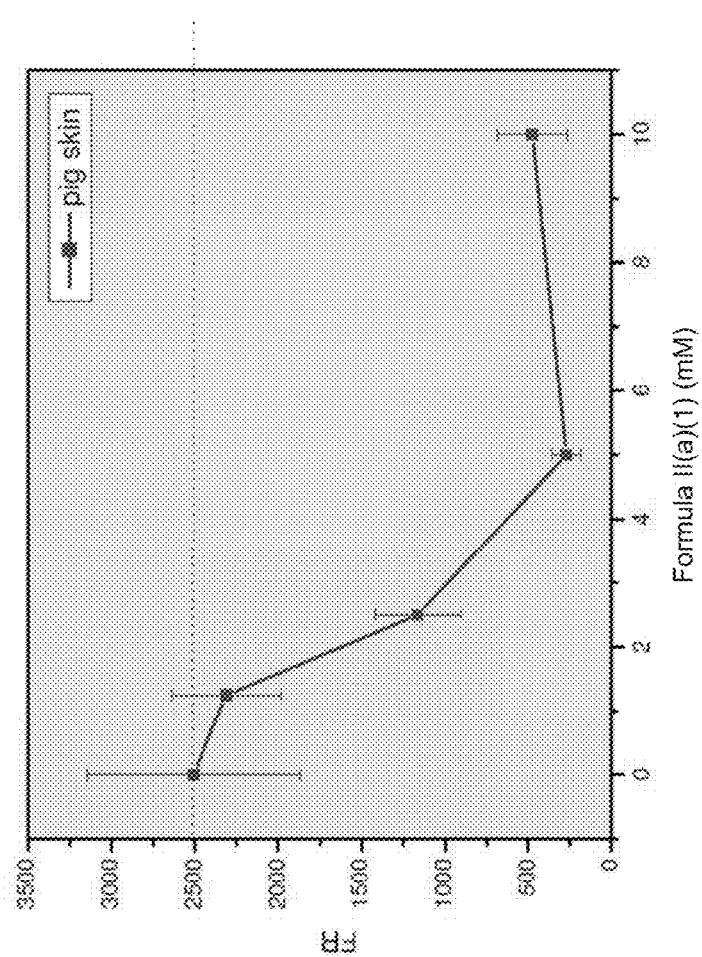
FIG. 21 illustrates a reduction in visible light-induced free radicals in pig skin mediated by a conjugated fused tricycle compound according to a specific example embodiment of the disclosure, as assessed by electron spin resonance.

A conjugated fused tricycle compound according to Formula II(a)(1) reduced visible light-induced free radicals in skin by up to 89% and did so in a dose-dependent manner (FIG. 21). The study was conducted using pig skin, which is recognized for its similarity to human skin. Topical application of aminolevulinic acid (ALA) induced the skin to over-produce the endogenous photosensitizer Protoporphyrin IX (PPIX). Solutions of Formula II(a)(1) at different concentrations were then topically applied to the ALA treated skin after which it was exposed to bright green light. The resulting free radical content of the skin was then measured by Electron Spin Resonance (ESR). Studies conducted in solution have shown that Formula II(a)(1) suppresses singlet oxygen production by PPIX. This was the first study demonstrating suppression of singlet oxygen in skin. Free radical reducing effects of the powerful antioxidant Tocopherol (Vitamin E) were also under the same conditions and found that Formula II(a)(1) is superior to Tocopherol in reducing visible light-induced free radicals in ALA-treated skin. The mechanisms of action of Formula II(a)(1) and Tocopherol are different: the former prevents free radicals from forming; the latter scavenges free radicals after they appear.

TABLE 3

Induced free radicals in pig skin treated with ALA and different concentrations of Formula II(a)(1)

| Concentration Formula II(a)(1) (mM) | Free Radicals (a.u.) | Free Radicals (%) |
|---|---|---|
| 0 | 2506 ± 638 | 100 |
| 1.25 | 2311 ± 331 | 92 |
| 2.5 | 1162 ± 225* | 46 |
| 5 | 270 ± 88* | 11 |
| 10 | 475 ± 212* | 19 |
| Reference: 1% Tocopherol | 1955 ± 366 | 78 |

*significant from the control (0 mM Formula II(a)(1) at $p < 0.05$).

Example 15: Performance Testing Compound II(c)(1)

Assays were performed to evaluate the extent to which test compounds suppress formation of reactive oxygen species (ROS) in cells.

A. Solubility in Cell Culture Media

All Conjugated fused polycyclic compounds tested (including Formulas II(a)(1), II(b)(1) and II(c)(1), and II(bk)) are highly soluble in DMSO, but poorly soluble in PBS buffer and cell culture medium. Formulas II(b)(1) and II(c)(1) can remain soluble in PBS buffer or cell culture medium if its concentration is less 0.2 mM. At concentrations higher than 0.2 mM, the solution begins to cloud and become emulsion like. This emulsion is able to remain stable for as long as 8 hours. Formula II(bk) is less soluble in PBS buffer and cell culture medium. It was only observed to dissolve in PBS at concentrations of 0.1 mM or less. Similar to Formulas II(b)(1) and II(c)(1), increasing Formula II(bk) concentration above 0.1 mM results in a cloudy emulsion like solution. But this cloudy solution is fairly stable and can be kept for more than 3 days. Formula II(a)(1) is especially difficult to dissolve in PBS buffer. Concentrations as low as 0.05 mM, but even at such a low concentration, the solution was not observed to be stable for long. One hour after adding Formula II(a)(1) to the PBS buffer or cell culture medium, almost all Formula II(a)(1) precipitatde to the bottom of tube or culture dish.

Conjugated fused polycyclic compounds may reduce the cellular ROS by quenching the excited states of PPIX. Accordingly, it may be desirable to deliver these molecules to and/or into cells where solubility may correlate with activity. Emulsification of conjugated fused polycyclic compounds may provide an effective delivery platform.

B. Toxicity

When HaCat cells, a human keratinocyte cell line, were treated with conjugated fused polycyclic compounds for short periods of time, there was no observed toxicity. HaCat cells have been treated with Formulas II(b)(1) and II(c)(1) at concentrations of 0.4 mM, 0.8 mM and 1.6 mM for up to 8 hours. Formulas II(b)(1) and II(c)(1) were then removed from the cell culture medium and the cells were cultured in new medium for another 24 hours. The treated cells were healthy, similar to the control cells (no Formulas II(b)(1) and II(c)(1)treatment).

Toxicity was observed in some experiments over longer intervals. However, conjugated fused polycyclic compounds may be applied topically ameliorating the potential for adverse impact. In addition, conjugated fused polycyclic compounds may delivered as an emulsion and/or with one or more additional molecules that lower observable toxicity.

C. Impact of Formulas II(b)(1) and II(c)(1) on Abundance of ROS

Conjugated fused polycyclic compounds may absorb UV light and, thereby, may screen, filter or block UV light (similar to sunscreen). The 5-aminolevulinic acid (ALA) experiment described here was performed to assess the relative impact of such filtering on suppression of induced cellular ROS. ALA is widely used in photodynamic therapy to kill tumor cells. It is a naturally occurring compound present in mammalian cells that can be metabolized to a porphyrin photosensitizer, protoporphyrin IX (PpIX). Applying ALA to the cells results in accumulation of PpIX in the treated cells. Irradiating with red light (or green light) will activate PpIX and lead to the production of cytotoxic reactive oxygen species (ROS).

HaCat cells were grown in 60 mm culture dishes to confluence. Confluent cells were treated with 8 mM ALA for 2 hour, then 2 mM of Formulas II(b)(1) and II(c)(1) was added (the control received an equal volume of DMSO buffer without Conjugated fused polycyclic compound). After 1 hour, the cells were irradiated for 3 minutes with red light beam (630 nm). The negative control (no irradiation) samples were kept in darkness. After washing with PBS buffer, the cells were stained with DFFDA for 30 minutes. The cells were washed with PBS 3 times again and then analyzed with fluorescent microscopy.

As seen in FIGS. 22A-22C, ALA treatment and red light irradiation significantly boost the abundance of cellular ROS (compared to the "no irradiation" control cells). Cells contacted with 2 mM Formulas II(b)(1) and II(c)(1), displayed a marked reduction in cellular ROS—levels similar to the "no irradiation" normal cell control. FIG. 22D shows the results of a quantitative analysis of the treated cells (n=4). ROS (based on relative fluorescence) for cells exposed to 8 mM ALA treatment and 3 minutes of red light irradiation was 84.6% higher than ALA treatment alone (no irradiation). On the other hand, cells incubated with 2 mM Formulas II(b)(1) and II(c)(1) for 1 hour, displayed a 15.85% increase in cellular ROS compared with the ALA treatment alone. That represents a more than 5 fold difference between the Formulas II(b)(1) and II(c)(1) treated and untreated cells. These data demonstrate that the Formulas II(b)(1) and II(c)(1) efficiently protect cells from irradiation-induced increase in ROS, possibly by a mechanism other than simple light filteration.

Figure 23:
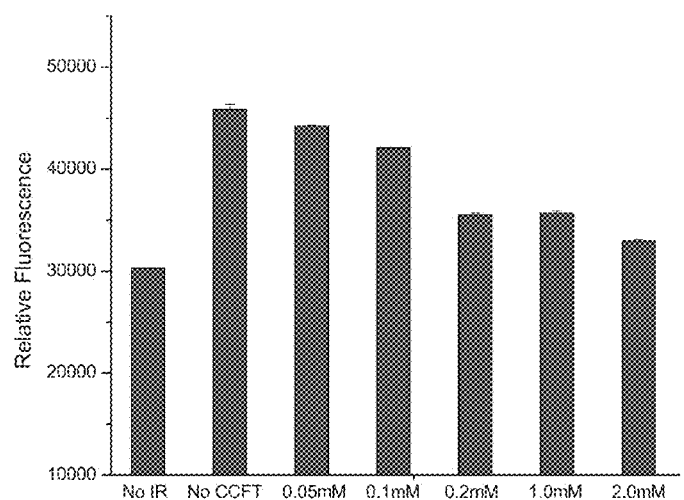
FIG. 23 illustrates the results of dosage response analyses of cultured human cells after exposure to visible light in the absence or presence of a conjugated fused tricycle compound according to a specific example embodiment of the disclosure.

The dosage range of Formulas II(b)(1) and II(c)(1) was also analyzed. As shown in FIG. 23, the cellular ROS (relative fluorescence) response is inversely correlated with to concentrations of Formulas II(b)(1) and II(c)(1) in the range of 0-0.2 mM (higher fluorescence at lower concentrations and lower fluorescence at higher concentrations). The effect of Formulas II(b)(1) and II(c)(1) on ROS appearance is saturated when the concentration exceeds 0.2 mM. Formulas II(b)(1) and II(c)(1) are soluble in PBS buffer or cell culture medium at concentrations of 0.2 mM and below, which may account for saturation of its effect on ROS—concentrations of Formulas II(b)(1) and II(c)(1) over 0.2 mM may not result in more molecules of Formulas II(b)(1) and II(c)(1) being available to cells.

Next, impact on ROA appearance was assessed as a function of exposure time. HaCat cells were seeded in the 60 mm cell culture dishes and grown to confluence. Confluent cells were treated with 8 mM ALA for 2 hours. Cells then received 1 mM of Formulas II(b)(1) and II(c)(1) and were incubated for various time periods from 1 minute to 60 minutes. At the end of the respective incubation periods, cells were irradiated for 3 minutes, washed with PBS buffer, and stained with DFFDA for 30 minutes. Cells were washed with PBS 3 times again and lysated by sonication. Cell lysates were analyzed with fluorescent plate reader to assess the cellular ROS. Experiments were done in triplicate.

Figure 24:
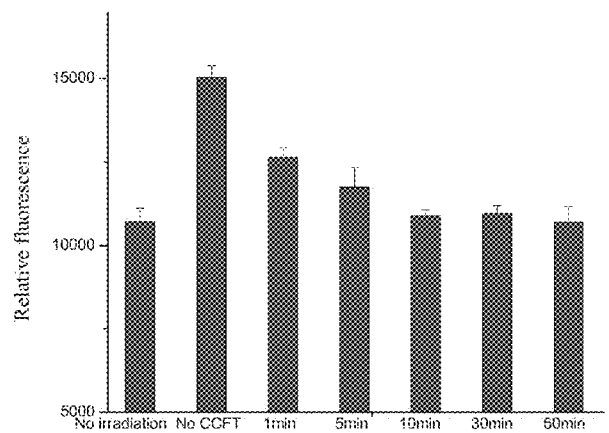
FIG. 24 illustrates the effect of incubation time on suppression of ROS accumulation in cultured human cells after exposure to visible light in the absence or presence of a conjugated fused tricycle compound according to a specific example embodiment of the disclosure.

As illustrated in FIG. 24, a significant reduction in ROS abundance was observed upon incubating cells with Formulas II(b)(1) and II(c)(1) for as little as 1 minute. The maximum effect (reduction of ROS) was observed after a 10 minute incubation with 1 mM of Formulas II(b)(1) and II(c)(1).

D. Impact on ROS: Comparison of Formulas II(a)(1), II(b)(1), II(c)(1), and II(Bk)

HaCat cells were seeded in 96-well plates and grown to confluence. Confluent cells were treated with 8 mM ALA for 2 hours. Cells then received 1 mM of Formula II(a)(1), II(b)(1)+II(c)(1), or II(bk). Following a one-hour incubation, cells were irradiated for 3 minutes, washed with PBS buffer, and stained with DFFDA for 30 minutes. Cells were then washed with PBS and the plate was directly analyzed with fluorescent plate reader. Experiments were done 4 times.

Figure 25:
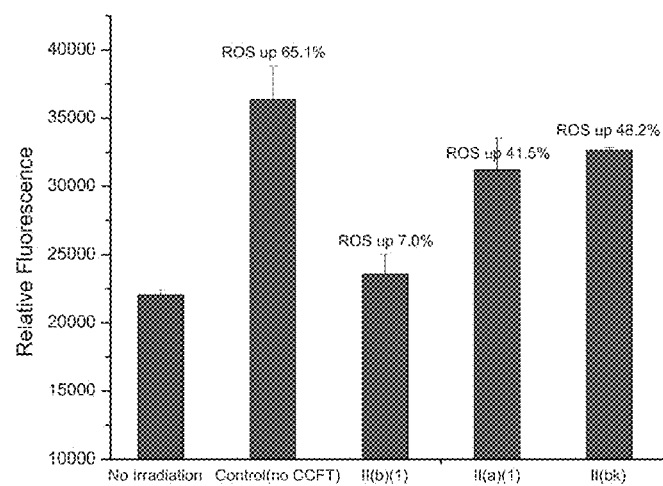
FIG. 25 illustrates the effect of various conjugated fused tricycle compounds on suppression of ROS accumulation in cultured human cells after exposure to visible light, according to specific example embodiments of the disclosure.

Results shown in FIG. 25 indicate that of the molecules tested, Formulas II(b)(1) and II(c)(1) was the most effective at suppressing the accumulation of cellular ROS after irradiation. As shown, with Formulas II(b)(1) and II(c)(1), the cellular ROS is close to baseline (no irradiation) after light irradiation. The ROS only increased by 7-12%. On the other hand, Formula II(a)(1) and Formula II(bk) are less efficient. They confer some protection, but far less than Formulas II(b)(1) and II(c)(1). With Formula II(a)(1) and Formula II(bk), the cellular ROS increased 40 to 50% comparing to no irradiation. These are better than no conjugated fused polycyclics controls, in which ROS increased by more than 60 to 70%, but not as good as Formulas II(b)(1) and II(c)(1).

E. Impact on Cell Viability: Comparison of Formulas II(a)(1), II(b)(1), II(c)(1), and II(Bk)

HaCat cells were seeded in 96-well plates and grown to confluence. Confluent cells were treated with 8 mM ALA for 2 hours. Cells then received 1 mM of Formula II(a)(1), II(b)(1)+II(c)(1), or II(bk). Following a one-hour incubation, cells were irradiated for 3 minutes and immediately washed with naïve cell culture media once. Additional cell culture media was added and the cells were cultured for 24 hours.

Figure 26:
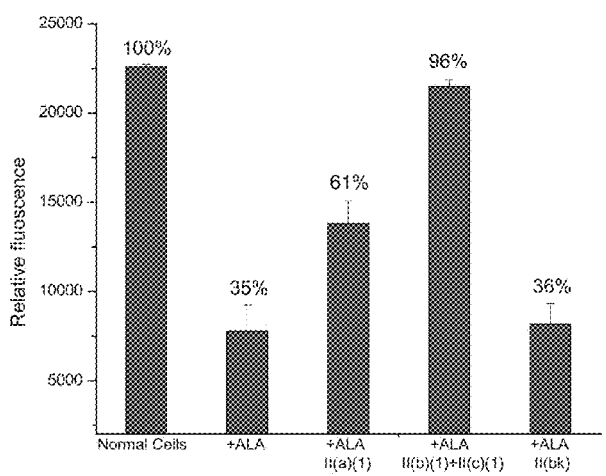
FIG. 26 illustrates survival of cultured human cells after exposure to visible light in the absence or presence of a conjugated fused tricycle compound according to a specific example embodiment of the disclosure.

A cell viabilty agent was added to each well and incubated for 2 hours. Cell viability was analyzed at the conclusion of this incubation by measuring the fluorescence intensity (excitation/emission 560/590) of each well. Results shown in FIG. 26 indicate that control cells (without conjugated fused polycyclic compound treatment) were almost completely killed by phototoxic ROS induced by ALA and light irradiation. Cell viability (cell metabolic activity) of light irradiated cells (without conjugated fused polycyclic) was only 35% of normal cell control (no treatment). Cells treated with Formulas II(b)(1) and II(c)(1) were so healthy that almost no difference was observed relative to normal controls. About 50% of Formula II(a)(1) treated cells survived, while cells without conjugated fused polycyclic compound exposure and cells treated with II(bk) were almost 100% dead. As seen in FIG. 26, cells treated with Formulas II(b)(1) and II(c)(1) have relative cell viability of 96% (no significant different from normal cell control). The Formula II(a)(1) was also observed to protect cells from light irradiation induced injury (relative cell viability 61%). On the other hand, II(bk) has no observed effect in protecting the cells (same as the samples without conjugated fused polycyclic treatment, relative cell viability 36%).

Figure 27:
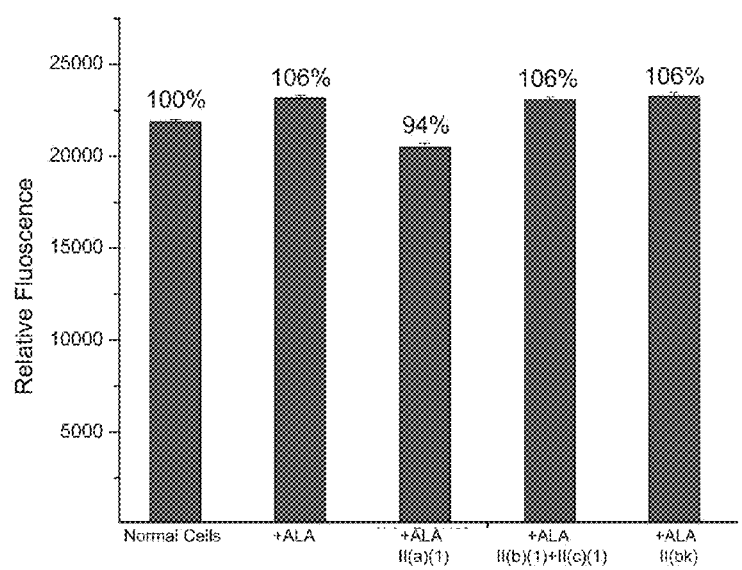
FIG. 27 illustrates survival of non-irradiated cultured human cells incubated with a conjugated fused tricycle compound according to a specific example embodiment of the disclosure.

To make sure that ALA and conjugated fused polycyclics treatments themselves are not influencing cell viability, (or cause cellular toxicity), dark toxicity analysis was performed. The experiment procedures were exactly same as above for cell viability analysis except that the red light irradiation step was omitted. As shown in FIG. 27, cells from all five treatments appeared healthy. No significant different between the 5 groups of cells was observed other than Formula II(a)(1) treatment showed a little toxicity.

Example 16: Performance Testing Formula II Compounds

The biomolecular quenching rate constants for singlet excited state ($k_q^S$) and triplet excited state ($k_q^T$) quenching of PPIX by stabilizers in acetonitrile solutions at room temperature is shown in Table 4, as well and the Stern-Volmer rate constants.

TABLE 4

Performance of Formula II Molecules

| Formula | Stern-Volmer Constant of $^1O_2$ Suppression ($M^{-1}$) | Singlet Quenching Rate Constant ($10^9$ $M^{-1}s^{-1}$) | Triplet Quenching Rate Constant ($10^9$ $M^{-1}s^{-1}$) |
|---|---|---|---|
| Formula II(a)(1) | 240 | 5.2 | 3.2 |
| Formula II(b)(1) + II(c)(1) | 31 | 4.5 | 0.25 |
| Formula I(a)(1) | 30 | 5.3 | 0.0061 |
| Formula II(d)(1) | 27 | 3.7 | 0.14 |
| Formula II(e)(1) | 1.2 | 0.65 | 0.0012 |
| Negative Control (alkoxy crylene) | 0.2 | None | None |

Stern-Volmer constants are in direct correlation with the singlet oxygen suppression efficiency. Table 4 (above) summarizes the Stern-Volmer constants and PPIX singlet and triplet state quenching rate constants. Three different ranges of Stern-Volmer constants were observed. For alkoxy crylene and compound II(e)(1), only negligible singlet oxygen suppression and low Stern-Volmer constants were observed, which is probably caused by the low PPIX singlet and triplet quenching rate constants of these stabilizers. For compounds I(a)(1), II(d)(1), and the mixture of II(b)(1) and II(c)(1), Stern-Volmer constants of about 30 $M^{-1}$ were observed. For these three stabilizers, high PPIX singlet quenching rate constants (about $5 \times 10^9$ $M^{-1}$ $s^{-1}$) but low triplet quenching rate constants ($<10^9$ $M^{-1}$ $s^{-1}$) were observed. Here, the singlet oxygen suppression is probably dominated by PPIX singlet excited state quenching by these stabilizers. The highest Stern-Volmer constant was observed for compound II(a)(1) (240 $M^{-1}$). Because of the very high PPIX triplet quenching rate constant by compound II(a)(1) ($3.2 \times 10^9$ $M^{-1}$ $s^{-1}$), the singlet oxygen suppression is probably dominated by triplet quenching. To prove this switch in mechanism and kinetic control of singlet oxygen suppression, additional kinetic parameters may be determined, which are easily accessible by laser flash photolysis and time correlated single photon counting. These kinetic parameters may include the MePPIX triplet and singlet lifetimes in air saturated and oxygen free $CDCl_3$ and the bimolecular quenching constant by oxygen.

What is claimed is:

1. A method for resolving at least one excited energy state of a photoactive molecule, the method comprising:
   positioning the photoactive molecule in electrical communication with a conjugated fused polycyclic molecule prior to, during, or following excitation of the photoactive molecule to the at least one excited energy state,
   wherein the conjugated fused polycyclic molecule has a structure according to Formula III:

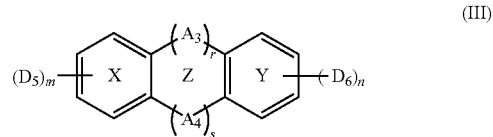

(III)

wherein
   m and n are each independently 0, 1, 2, 3, or 4,
   r and s each may be 0 or 1,
   $A_3$ and $A_4$ are each independently carbonyl, C=C($R_{27}$)$R_{28}$, O, S, S=O, S(O)=O, or C=S,
   $R_{27}$ is independently nitrile, C(O)O$R_{29}$, C(O)$R_{30}$, C(O)N($R_{31}$)$R_{32}$, C(O)—S—$R_{33}$, C(O)—O—S—$R_{34}$, C=CH$R_{35}$, N($R_{36}$)$_3^+$, F, Cl, Br, I, CF$_3$, CCl$_3$, NO$_2$, aryl, substituted aryl, or fused aryl,
   $R_{28}$ is independently nitrile, C(O)O$R_{37}$, C(O)$R_{38}$, C(O)N($R_{39}$)$R_{40}$, C(O)—S—$R_{41}$, C(O)—O—S—$R_{42}$, C=CH$R_{43}$, N($R_{44}$)$_3^+$, F, Cl, Br, I, CF$_3$, CCl$_3$, NO$_2$, aryl, substituted aryl, or fused aryl,
   $R_{29}$ and $R_{37}$ are each independently H, alkyl, branched alkyl, cycloalkyl, alkenyl, cycloalkenyl, alkynyl, aryl, substituted aryl, or fused aryl,
   $R_{30}$, $R_{31}$, $R_{32}$, $R_{33}$, $R_{34}$, $R_{35}$, $R_{38}$, $R_{39}$, $R_{40}$, $R_{41}$, $R_{42}$, and $R_{43}$ are each independently H, alkyl, cycloalkyl, alkenyl, cycloalkenyl, alkynyl, or aryl, substituted aryl, or fused aryl, alkyl, substituted alkyl, or branched alkyl,
   $R_{36}$ and $R_{44}$ are each independently H or $C_1$-$C_6$ alkyl, and
   $D_5$ and $D_6$ are each independently $R_{27}$, $R_{28}$, heteroaryl, hydroxyl, alkyl, or alkoxyl, provided that
   r+s≥1, and
   at least one of $A_3$ and $A_4$ is C=C($R_{27}$)$R_{28}$,
   wherein if r+s=1; then $R_{27}$ and $R_{28}$ are each independently ≠F, Cl, Br, I, aryl, substituted aryl, or fused aryl; $R_{29}$ and $R_{37}$ are each independently ≠alkyl, branched alkyl, cycloalkyl, aryl, substituted aryl, or fused aryl; and $D_5$ and $D_6$ are each independently ≠heteroaryl, hydroxyl, alkyl, or alkoxyl; and wherein if r+s=1, then only one of $R_{27}$ and $R_{28}$ is nitrile.

2. A method according to claim 1, wherein the at least one excited state of the photoactive molecule is resolved substantially without observable photochemical reaction or without observable photosensitization reactions.

3. A method according to claim 1, wherein the at least one excited state of the photoactive molecule is resolved substantially non-radiatively.

4. A method according to claim 1, wherein the at least one excited state of the photoactive molecule is resolved substantially non-radiatively, substantially without observable photochemical reaction, and substantially without observable photosensitization reactions.

* * * * *